United States Patent
Yamamoto et al.

(10) Patent No.: US 6,642,257 B2
(45) Date of Patent: Nov. 4, 2003

(54) AGENTS FOR TREATING NEUROPATHIC PAIN

(75) Inventors: Ichiro Yamamoto, Shinjuku-ku (JP); Manabu Itoh, Shinjuku-ku (JP); Fumiaki Yamasaki, Shinjuku-ku (JP); Yasushige Akada, Shinjuku-ku (JP); Yutaka Miyazaki, Shinjuku-ku (JP); Shinichi Ogawa, Shinjuku-ku (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/969,644

(22) Filed: Oct. 4, 2001

(65) Prior Publication Data

US 2002/0049229 A1 Apr. 25, 2002

Related U.S. Application Data

(63) Continuation-in-part of application No. PCT/JP00/02332, filed on Apr. 10, 2000.

(30) Foreign Application Priority Data

Apr. 9, 1999 (JP) ............................................. 11-103212
Jan. 31, 2000 (JP) ........................................ 2000-023116

(51) Int. Cl.$^7$ .............................................. A61K 31/44
(52) U.S. Cl. ........................................ 514/327; 546/216
(58) Field of Search ............................... 546/184, 192, 546/216; 514/315, 317, 327, 329

(56) References Cited

U.S. PATENT DOCUMENTS

| | | | |
|---|---|---|---|
| 3,600,395 A | | 8/1971 | Regnier et al. |
| 5,589,486 A | * | 12/1996 | Harsanyi et al. ............. 514/317 |
| 6,008,233 A | * | 12/1999 | Andino et al. ............... 514/327 |
| 6,017,933 A | * | 1/2000 | Dimmock et al. ............ 514/327 |
| 6,455,549 B1 | * | 9/2002 | Annoura et al. ............. 514/327 |
| 2001/0000038 A1 | * | 3/2001 | Krauss et al. ................ 546/210 |

FOREIGN PATENT DOCUMENTS

| | | |
|---|---|---|
| CH | 589 055 | 6/1977 |
| EP | 0 869 119 A1 | 10/1998 |
| WO | WO 93/14084 | 7/1993 |
| WO | WO 95/11231 | 4/1995 |
| WO | WO 98/24428 | 6/1998 |
| WO | WO99/48492 | 9/1999 |

OTHER PUBLICATIONS

Darrell L. Tanelian et al., "Neuropathic Pain Can Be Relieved by Drugs That Are Use–dependent Sodium Channel Blockers: Lidocaine, Carbamazepine, and Mexilietine," *Anesthesiology*, vol. 74, No. 5, pp. 949–951, 1991.

Darrell L. Tanelian et al., "Sodium Channel–blocking Agents: Their Use in Neuropathic Pain Conditions," *Pain Forum*, vol. 4, No. 2, pp. 75–80, 1995.

Huegi et al., "Synthesis and Pharmacological Studies of 4,4–Disubstituted Piperidines: A New Class of Compounds with Potent Analgesic Properties", *J. Med. Chem.*, 1983, vol. 26, No. 1, pp42–50.

* cited by examiner

Primary Examiner—Jean F. Vollano
(74) Attorney, Agent, or Firm—Oliff & Berridge, PLC

(57) ABSTRACT

The present invention relates to a compound represented by Formula (I) below:

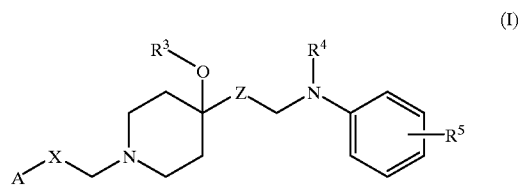

(I)

(wherein A represents, for example, phenyl group substituted by $R^1$ and $R^2$, or an unsubstituted furyl group or an unsubstitued thienyl group; $R^1$ represents, for example, hydrogen atom, fluorine atom, chlorine atom, trifluoromethyl group, nitro group, cyano group or methyl group while $R^2$ represents, for example, hydrogen atom; $R^3$ represents, for example, hydrogen atom or methyl group; $R^4$ represents, for example, hydrogen atom or methyl group; $R^5$ represents ethoxy group or isopropoxy group; X represents group: —CH(OH)— or methylene group; and Z represents, for example, a single bond or methylene group unsubstituted or substituted by hydroxyl group), and its salts, and medicinal compositions containing, as their active ingredient, the above compound or its salts. The compound of this invention, which is orally applicable, is highly effective for treating neuroapthic pain while presenting with fewer side-effects than do the conventional analgesics.

5 Claims, No Drawings

AGENTS FOR TREATING NEUROPATHIC PAIN

This is a continuation-in-part of international application No. PCT/JP00/02332 filed Apr. 10, 2000. The entire disclosure of the prior application is hereby incorporated by reference herein in its entirety.

BACKGROUND OF THE INVENTION

1. Field of the Invention

The present invention relates to novel 4-hydroxypiperidine derivatives, a method for their manufacture, and pharmaceutical compositions containing, as its active ingredient, at least one of the derivatives, particularly an orally applicable agent for treating neuropathic pain. The present invention further relates to an agent for treating neuropathic pain, characterized by its containing, as its active ingredient, a substance which selectively inhibits the persistent sodium current.

2. Description of Related Art

Neuropathic pain is caused by a primary damage or by a functional disorder of some part of the neuro transmission system connecting the periphery to the central nervous system (New Illustrated Anesthetic Science Series, No. 4, "Clinics of Pain Control," 1st Chapter, Written by Kenjiro Dan, 1998, Medical View). In contrast with the physiological pain (nociceptive pain) caused by a mechanical stimulus or a thermal stimulus, the neuropathic pain might be called as a pain felt even by a feeble stimulus which would cause no pain in the normal person, or a pain which is felt without stimulus.

The damage to nerves which becomes a cause to induce the neuropathic pain typically includes traumas and injuries inflicted to the peripheral nervous system, nerve plexus, and soft tissues surrounding the nerves, as well as injuries to the somatesthesia paths in the central nervous system (such as ascending somatesthesia paths found at the levels of spinal cord, brain stem, thalamus and cerebral cortex). For example, neuropathic pain may occur in association with nerve degenerative diseases, bone degenerative diseases, metabolic diseases, cancer, infection, inflammation, post-surgery state, trauma, radiation therapy and anti-cancer chemotherapy, etc. The pathophysiology of neuropathic pain, especially molecular mechanisms responsible for its elicitation are not fully clarified yet. However, it has been thought that over-excitation or abnormal spontaneous excitation prevails in a injured nerve, which is the cause for the neuropathic pain.

The abnormal reaction against sensation, which is characteristic with neuropathic pain, includes, e.g., allodynia. Allodynia refers to a state in which one feels a pain in the presence of a feeble stimulus which would cause no pain in a normal person. In allodynia, even a gentle tactile stimulus can elicit a pain. Basically this is thought to be accounted for by two factors, namely, a qualitative change in sensory responses and the abnormally lowered sensory threshold. Of the patients with neuralgia subsequent to herpes zoster (postherpetic neuralgia), which is a representative neuropathic disorder, 87% was confirmed to have been affected with allodynia. In addition, it has been said that the severity of pain felt in postherpetic neuralgia is proportional to the severity of allodynia. Allodynia, a pathologic state severely restricting the activity of the patient attracts attention as a target for the treatment of postherpetic neuralgia.

If a patient complains of chronic pain as a result of neuropathy, and is disturbed in his/her everyday activity on account of that pain, relieving him/her of that pain through medication will directly lead to the improvement of his/her quality of life. However, it has been shown that the centrally affecting analgesics represented by morphine, non-steroidal anti-inflammatory agents, or steroids are ineffective for the treatment of neuropathic pain. In the current drug therapy, antidepressants such as amitriptyline, sodium channel blockers such as carbamazepine, anti-epileptic agents such as phenytoin, anti-arrhythmic agents such as mexiletine, etc. are diverted from their respective proper fields to the prescription for the treatment of neuropathic pain. Among them, the sodium channel blockers are used to inhibit the hyper-excitability or abnormal spontaneous activity of injured nerves which is regarded as one of the causes for neuropathic pain, because the sodium channel blockers are known to inhibit the excitation and conduction in nerves. The above therapeutic agents, however, are known to bring about a number of side-effects: amitriptyline may cause thirst, drowsiness, sedation, constipation, dysuria, etc.; carbamazepine and phenytoin may cause gait disorder (staggering), eruption, dyspepsia, harmful effects on cardiac functions, etc.; and mexiletine may cause dizziness, dyspepsia, etc. Those agents which are not originally intended for the treatment of neuropathic pain are not satisfactory for many neuropathy cases because their therapeutic effects are inseparably linked with their side-effects. Accordingly, there is a need for an agent which is primarily intended for the treatment of neuropathic pain, presenting with few side-effects.

About the pain-relieving activity of the sodium channel blocker such as phenytoin, what follows is known.

A sodium current ordinarily observed in an excitable cell is a transient inward current (transient sodium current) which is activated rapidly in the presence of a stimulus (depolarization), and then inactivated. In certain states, however, the inactivation process is greatly retarded or hardly occurs, and the sodium current observed then is called a persistent sodium current. It is known, the occurrence of such a persistent sodium current may increase when the cell falls to certain pathological conditions.

Recently, it was reported that phenytoin inhibits the persistent sodium current in neurons, and that this is responsible for the anti-epileptic activity of that agent (Segal and Douglas, J. Neurophysiol., 77:3021, 1997). Recent studies indicate the persistent sodium current may be involved in the pathologic state of myocardium (for example, the development of arrythmia), in addition to epilepsy (Yue-Kun et al., Br. J. Pharmacol., 107:311–316, 1992). It has been also suggested, because phenytoin and carbamazepine inhibit the transient sodium current which plays an important role in the excitation and conduction in neurons, as well as the persistent sodium current (Willow et al., Mol. Pharmacol., 27:549, 1985), they will be able to inhibit not only the abnormal excitation responsible for neuropathic pain, but also the normal nerve activity, and the latter effect may be responsible for their adverse side-effects mentioned above.

With regard to 4-hydroxypiperidine derivatives, Huegi et al. (J. Med. Chem., 26:42, 1983) reported there are some among them that have a pain-relieving activity. However, the compounds cited by them are centrally affecting pain-relieving agents like morphines which have affinity to the opiate receptors in neurons, and are distinct from the compounds of the present invention which are primarily intended for the treatment of neuropathic pain.

The problem to be solved by this invention is to provide an agent for treating neuropathic pain which will exert its therapeutic effects by selectively inhibiting the persistent sodium current in comparison with the transient sodium current, and thus presenting with less side-effects but more therapeutic effects than do the conventional sodium channel blockers which have been diverted from other fields for the treatment of neuropathic pain, particularly to provide such an agent orally applicable.

SUMMARY OF THE INVENTION

The present inventors had intensively studied to solve the above problem, or to obtain a pain-relieving agent highly active and safe, and found that substances capable of selectively inhibiting the persistent sodium current in comparison with the transient sodium current, for example, 4-hydroxypiperidine derivatives as represented by Formula (I) and their salts are highly effective for the treatment of neuropathic pain, and particularly that those substances are effective for the treatment of neuropathic pain by selectively acting on injured sites. These findings led to this invention.

DETAILED DESCRIPTION OF THE INVENTION

Specifically, the inventors found that the compound as represented by Formula (I) has at least one of the following properties: (1) to inhibit the binding of batrachotoxin to receptors in the synaptosome; (2) to inhibit the contracture induced in isolated myocardial cells, or to inhibit the increased intracellular sodium concentration induced by vetratrine in neurons; (3) to moderate the painful response in the formalin test; (4) to selectively raise the threshold to a mechanical stimulus applied on the injured side in a model of neuropathy made by loosely constricting the sciatic nerve; (5) to selectively inhibit the persistent sodium current in neurons; and (6) to present with comparatively less side-effects, and be highly safe. Particularly, the compound represented by Formula (I) is highly effective for the treatment of neuropathic pain even when applied orally.

The first embodiment of this invention is compounds as represented by Formula (I) below:

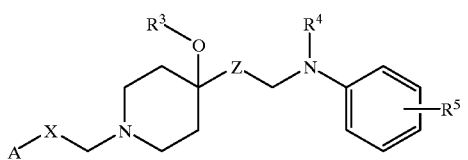

(I)

(wherein A represents phenyl group or monocycic aromatic heterocylic ring each substituted by $R^1$ and $R^2$; $R^1$ and $R^2$ represent, independently of each other, a group arbitrarily selected from the group of hydrogen atom, halogen atom, trifluoromethyl group, trifluoromethoxy group, nitro group, cyano group, lower alkoxycarbonyl group, amino group unsubstituted or mono- or di-substituted by lower alkyl groups, carbamoyl group unsubstituted or mono- or di-substituted by lower alkyl groups, sulfamoyl group unsubstituted or mono- or di-substituted by lower alkyl groups, unprotected or protected hydroxyl group, unprotected or protected carboxyl group, lower alkoxy group, lower alkyl group, lower alkylthio group, lower alkylsulfinyl group, lower alkylsulfonyl group and lower alkanoyl group; $R^3$ represents hydrogen atom or lower alkyl group; $R^4$ represents hydrogen atom or lower alkyl group; $R^5$ represents ethoxy group or isopropoxy group; X represents a group: —CH(OH)— or methylene group; and Z represents a single bond or methylene group unsubstituted or substituted by unprotected or protected hydroxyl group), and its pharmaceutically acceptable salts.

For the compounds represented by Formula (I), preferred substitutents and their preferred combinations will be introduced below, but this invention should not be limited to those examples.

Preferably A represents phenyl, furyl or thienyl group each substituted by $R^1$ and $R^2$, more preferably phenyl group substituted by $R^1$ and $R^2$, unsubstituted furyl group or unsubstituted thienyl group, most preferably phenyl group substituted by $R^1$ and $R^2$.

$R^1$ preferably represents hydrogen atom, halogen atom, trifluoromethyl group, trifluoromethoxy group, nitro group, cyano group, lower alkoxycarbonyl group, lower alkoxy group, lower alkyl group, lower alkylthio group or lower alkanoyl group, more preferably hydrogen atom, halogen atom, trifluoromethyl group, nitro group, cyano group or lower alkyl group, most preferably hydrogen atom, halogen atom or cyano group.

$R^2$ preferably represents hydrogen atom or halogen atom, more preferably hydrogen atom.

For combination of $R^1$ and $R^2$, $R^1$ preferably represents hydrogen atom, halogen atom, trifluoromethyl group, trifluoromethoxy group, nitro group, cyano group, lower alkoxycarbonyl group, lower alkoxy group, lower alkyl group, lower alkylthio group or lower alkanoyl group while $R^2$ represents hydrogen atom; more preferably $R^1$ represents hydrogen atom, halogen atom, trifluoromethyl group, nitro group, cyano group or lower alkyl group while $R^2$ represents hydrogen atom; most preferably $R^1$ represents hydrogen atom, halogen atom or cyano group while $R^2$ represents hydrogen atom.

$R^3$ preferably represents hydrogen atom.
$R^4$ preferably represents lower alkyl group.
$R^5$ preferably represents isopropoxy group.
$R^5$ is preferably substituted at the para position (4th position) with respect to —$NR^4$—.
X preferably represents methylene group.
Z preferably represents methylene group.

For preferred combination of substituents, A represents phenyl group, furyl group or thienyl group each substituted by $R^1$ and $R^2$, $R^1$ represents hydrogen atom, halogen atom, trifluoromethyl group, trifluoromethoxy group, nitro group, cyano group, lower alkoxycarbonyl group, lower alkoxy group, lower alkyl group, lower alkylthio group or lower alkanoyl group while $R^2$ represents hydrogen atom; more preferably A represents phenyl group substituted by $R^1$ and $R^2$, unsubstituted furyl group or unsubstituted thienyl group, $R^1$ represents hydrogen atom, halogen atom, trifluoromethyl group, nitro group, cyano group or lower alkyl group while $R^2$ represents hydrogen atom, and $R^5$ is substituted at the para position (4th position) with respect to —$NR^4$—.

The second embodiment of this invention is a pharmaceutical composition containing, as its active ingredient, a compound represented by Formula (I), or a pharmaceutically acceptable salt thereof.

The third embodiment of this invention is an agent useful for the treatment of neuropathic pain which contains, as its active ingredient, a compound represented by Formula (I), or a pharmaceutically acceptable salt thereof, or an orally applicable such an agent useful for the treatment of neuropathic pain.

The fourth embodiment of this invention is an allodynia treating agent which contains, as its active ingredient, a compound represented by Formula (I), or a pharmaceutically acceptable salt thereof, or an orally applicable such agent useful for the treatment of allodynia.

The fifth embodiment of this invention is an agent useful for the treatment of neuropathic pain which contains, as its active ingredient, a substance that selectively inhibits the persistent sodium current, or more preferably an orally applicable such agent useful for the treatment of neuropathic pain.

The sixth embodiment of this invention is an allodynia treating agent which contains, as its active ingredient, a substance that selectively inhibits the persistent sodium current, or more preferably an orally applicable such agent useful for the treatment of allodynia.

The seventh embodiment of this invention is an agent useful for the treatment of neuropathic pain which contains, as its active ingredient, a substance that interferes with the persistent sodium current, and selectively acts on the injured side of sciatic nerves in the Bennett's model.

The eighth embodiment of this invention is an agent useful for the treatment of neuropathic pain which contains a substance that selectively inhibits the persistent current in comparison with the transient current of sodium in neurons observed by the voltage-clamp method.

The ninth embodiment of this invention is an agent useful for the treatment of neuropathic pain or allodynia as described in the fifth to the eighth embodiments, which contains, as its active ingredient, a substance whose selective inhibition against the persistent sodium current is two-fold or more, preferably five-fold or more, more preferably ten-fold or more with respect to its inhibition against the transient current.

Here, the selective inhibition against the persistent sodium current of an agent with respect to its inhibition of the transient sodium current can be expressed by the ratio of inhibition of the transient sodium current by the agent against inhibition of the persistent sodium by the same agent (inhibition ratio=the concentration (for example, in vitro $IC_{50}$ or in vivo dose) of the agent required for inhibiting the transient sodium current against the corresponding concentration (in vitro $IC_{50}$ or in vivo dose) of the same agent against the persistent sodium current).

More preferably, the ninth embodiment contains a substance that satisfies at least one of what are described under (A) and (B) below:

(A) The inhibition ratio is 4 or more, preferably 7 or more, more preferably 10 or more, and most preferably 20, when determined on neurons by the voltage-clamp method (for example Experiment 6).

(B) The inhibition ratio is 2 or more, preferably 5 or more, more preferably 10 or more, when determined in the Bennett's model (for example Experiment Example 5).

It will be possible to evaluate whether a given agent has a sufficient selectivity or not, by checking whether it does not affect the action potential of myocardial cells, or whether it is free from the side-effects accompanying the conventional agents used for the treatment of neuropathic pain.

In addition to the selectivity and independently thereof, the agent preferably has at least one of the properties mentioned in (1) to (3) below.

(1) When the test agent is tested for its inhibitory effect on the binding of batrachotoxin to receptors in the rat brain as in Experiment Example 1 described below, the $IC_{50}$=500 μmol/L or less, preferably 50 μmol/L or less, more preferably 10 μmol/L or less, most preferably 1 μmol/L or less.

(2) When the test agent is tested for its inhibitory effect on the persistent sodium current as in Experiment Example 2 or 3 described below, the $IC_{50}$=50 μmol/L or less, preferably 10 μmol/L or less, more preferably 2 μmol/L or less.

(3) When the test agent is tested for its inhibitory effect on the persistent sodium current on a Benett's model based on a sciatic nerve-muscle contracture preparation as in Experiment Example 4 below, the dose of the test agent effective for raising the response threshold when applied to a site distal to the pressure application is 100 mg/kg or less, preferably 50 mg/kg or less, more preferably 10 mg/kg or less, particularly preferably 5 mg/kg or less, most preferably 2.5 mg/kg or less.

The tenth embodiment of this invention is an agent as described in the third to ninth embodiments useful for the treatment of neuropathic pain or allodynia which is orally applicable to mammals. The mammal preferably includes, in addition to humans, household pets such as dogs, cats, etc. Particularly, it is effective when applied to humans.

The third to tenth embodiments include, in addition to the therapeutic method for the treatment of neuropathic pain or allodynia based on the use of the agent, the method how to prepare a medicine useful for the treatment of neuropathic pain or allodynia from the agent. Particularly, the agent is preferably prepared into an orally applicable medicine, and the therapy is based on the oral administration of such a medicine.

The therapeutic agent described above is preferably effective for the treatment of pain accompanying central neuropathy (for example, neuropathy resulting from spinal cord injury), peripheral neuropathy (for example, reflex sympathetic dystrophy (RSD)), herpes zoster during its acute phase, neuralgia subsequent to herpes zoster (post-herpetic neuralgia), diabetic neuropathy, trigeminal neuralgia, post-surgery condition, cancer, low back pain-related neuropathy, inflammatory shoulder joint and its surrounds, state subsequent to spinal cord injury, affected thalamus, affected lower limb, causalgia, reflex sympathetic nerve atrophy, chronic headache, affected tooth, osteoarthritis, arthritis, rheumatism, etc. Or, the therapeutic agent is effective for prevention or inhibition against aggravation of symptoms in the development of chronic painful disease. Or, the therapeutic agent is effective not only for the treatment of neuralgia, headache, etc., but also for the treatment of convulsion, epilepsy, dementia (cerebrovascular and senile dementia), cerebral infarction during its acute phase, cerebral hemorrhage, transient cerebral ischemia, subarachnoidal hemorrhage, head trauma, after-effects subsequent to brain surgery, cerebral vascular disorders subsequent to cerebral arterial sclerosis, atopic dermatitis, itching occurring during hemodialysis to compensate for renal failure, hypersensitive enteral syndrome, urinary incontinence, etc. The concept underlying the therapy of this invention includes so-called prevention of disease development, and prevention of relapse.

Particularly, the therapeutic agent is effective for the treatment of pain accompanying neuralgia subsequent to herpes zoster, diabetic neuropathy, trigeminal neuralgia, state subsequent to surgery, etc., which is followed by the treatment of pain accompanying herpes zoster during its acute phase, cancer, and chronic rheumatoid arthritis, and by the treatment of urge incontinence, hypersensitive enteral syndrome, etc.

The eleventh embodiment of this invention is a method for selecting by screening a substance which is effective for selectively blocking the persistent sodium current in neurons. The screening method preferably comprises at least one chosen from the group including Processes 1 to 5 as described below. The screening method more preferably comprises at least either Processes 2 and 4, or Process 5.

The twelfth embodiment of this invention is a method for selecting by screening an agent effective for the treatment of neuropathic pain or allodynia, comprising at least a process of checking whether the test agent selectively inhibits the persistent sodium current by the voltage-clamp method.

The thirteenth embodiment of this invention is a substance selected by screening in the eleventh or twelfth embodiment.

The fourteenth embodiment of this invention is a method for producing a compound represented by Formula (I)-a below, or Formula (I) wherein Z is Z':

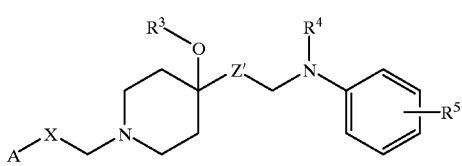
(I)-a (wherein A, R³, R⁴, R⁵ and X have the same meanings as defined above, while Z' represents methylene groug unsubstituted or substituted by unprotected or protected hydroxyl group), and its salts, based on process (a) or (b) below.

Process (a)

A process characterized by adding a compound represented by the following formula (XI):

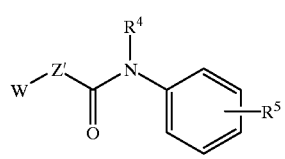
(XI)

(wherein R⁴, R⁵ and Z' have the same meanings as defined above, while W represents hydrogen atom or halogen atom) to another compound represented by the following formula (XII):

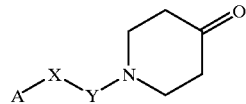
(XII)

(wherein A and X have the same meanings as defined above, while Y represents a methylene group or carbonyl group) and alkylating the newly formed hydroxyl group as needed to produce a compound as represented by the formula (VI') below:

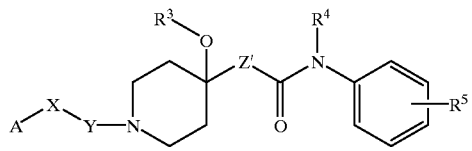
(VI')

(wherein A, R³, R⁴, R⁵, X, Y and Z' have the same meanings as defined above), and then reacting the resulting compound under a reducing condition.

Process (b)

A process characterized by adding a compound represented by the following formula (XI):

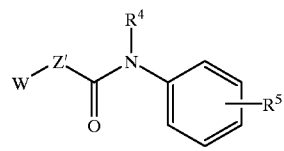
(XI)

(wherein R⁴, R⁵, W and Z' have the same meanings as defined above) to another compound represented by the following formula (XIII):

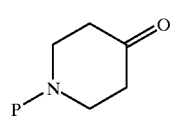
(XIII)

(wherein P represents a protective group for protecting the amino group) and alkylating the newly formed hydroxyl group as needed to produce a compound as represented by the formula (VII') below:

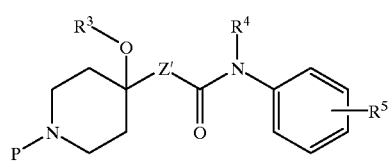
(VII')

(wherein R³, R⁴, R⁵, Z' and P have the same meanings as defined above), and deprotecting and reducing the resulting compound to produce a compound as represented by the formula (X') below:

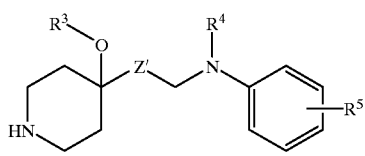
(X')

(wherein R³, R⁴, R⁵ and Z' have the same as defined above), and reacting the resulting compound with another compound as represented by the formula (IX) below:

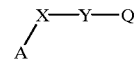
(IX)

(wherein A, X and Y have the same meanings as defined above, and Q represents hydrogen atom, hydroxyl group or halogen atom) in the presence or absence of a base, if —Y and Q together represent halogenated alkyl group; under a reducing condition in the presence or absence of an acidic catalyst, if —Y and Q together represent aldehyde; or in the presence of a condensing agent and then under a reducing condition, if —Y and Q together represent carboxylic acid.

This invention will be described in detail below.

The agent of this invention for selectively blocking the persistent sodium current can be detected, for example, through the experiments as described below, and is a protein or a low molecular weight compound naturally occurring or artificially prepared based on genetic engineering, having a molecular weight of preferably about 1500 or less, more preferably 1000 or less, more preferably 700–300, or its salts. The representative one is the compound represented by Formula (I) which will be detailed later, and its pharmaceutically acceptable salts.

With regard to the agent of this invention for selectively blocking the persistent sodium current, "selectively" means, in terms of the inhibition ratio as defined above in relation to the eighth embodiment, 4 or more, preferably 7 or more, more preferably 10 or more, most preferably 20 or more, when the ratio is based on $IC_{50}$ values obtained from an in vitro experiment. In the in vivo experiment, the dose required for treating the pain in a normal nerve against the corresponding dose for a neuropathy-affected nerve is 2-fold or more, preferably 5-fold or more, more preferably 10-fold or more.

To find whether a given compound sufficiently selectively blocks the persistent sodium current to be qualified for an agent of this invention, various methods can be employed, and a few examples of them will be described for illustration.

(1) Firstly, a persistent sodium current itself or a phenomenon coupled with the development of the current is monitored, to check whether a given test compound has any inhibitory action against the persistent sodium current. [1] It is possible to detect a persistent sodium current by the voltage-clamp method (Baker and Bostock, J. Neurophysiol., 77:1503, 1997; Segal and Douglas, J. Neurophysiol., 77:3021, 1997; Taverna et al., J. Pharmacol. Exp. Ther., 288:960, 1999, and Verdonck et al., Eur. J. Pharmacol., 203:371, 1991). [2] It is possible to elicit the altered configuration of cells coupled with the development of persistent sodium current, by applying a toxin such as veratrine or veratridine to the cell or by depolarizing the membrane potential of the cell (Experiment Example 2 described below). [3] It is also possible to achieve the same purpose by following the effect of a test compound on the sodium concentration within the cell (Mittmann et al., J. Neurophysiol., 78:1188, 1997; Russ et al., Pflugers Archiv. Eur. J. Physiol., 433:26, 1996) or in the synpatosome (Deffois et al., Neuroscience Letter, 220:117, 1996), because when the persistent sodium current develops, the intracellular sodium concentration will increase in association.

(2) Next, the selective action of a test compound towards the persistent sodium current relative to the transient sodium current can be determined as follows: [1] to check the action of the compound against the transient sodium current using the voltage-clamp method, and then to compare the result with the corresponding result obtained in Observation (1) above (Suma et al., Eur. J. Pharmacol., 336:283, 1997). It is also possible to check whether a test compound has any inhibitory action against the transient sodium current, [2] by following its effect on the maximum upsroke velocity of the action potential (Campbell, J. Cardiovasc. Pharmacol., 5:291, 1983), or [3] by measuring its effect on the conduction velocity of the cardiac muscle or of a nerve fiber in the in vivo experiment, or more simply [4] by determining its effect on the PQ interval or QRS width in the electrocardiogram. Moreover, it is also possible to study the selective action of a test compound in a single experiment, [5] by taking a neuropathy animal model (for example, see Example 4 described below), determining its effects on a normal nerve and on an injured nerve, and comparing the results.

Alternatively, observation (1) or (2) may be carried out through the method proposed by Verdonck et al. (Eur. J. Pharmacol., 203:371, 1991). According to this method, myocardial cells or nerve cells isolated from mammals such as rats, guinea pigs, rabbits, etc., or cells from a cell strain derived from neuroblastoma may be used. Isolated cells are strewn over a recording chamber filled with perfusion fluid; the membrane currents are recorded in a whole cell configuration by the voltage-clamp method based on the use of a glass microcapillary. Current components due to ions other than sodium ion, including, for example, the potassium current component must be eliminated in advance by adding known specific channel blockers to the perfusion fluid. Measurement of the transient sodium current of the cells is achieved by applying depolarizing pulses at appropriate intervals to the cells clamped at holding potential, and by observing a transient inward current elicited therewith. The test compound of this invention is added to the perfusion fluid; its effect on the peak value of the inward current is followed; and then for example its $IC_{50}$ is determined. Observation of the persistent sodium current is achieved by adding veratridine to the perfusion fluid to 10–30 $\mu$mol/L, and shifting the holding potential towards depolarization, which will cause a persistent inward current to develop in the cells. Then, the test compound of this invention is added to the same perfusion fluid containing veratridine; its effect on the persistent inward current is followed; and its $IC_{50}$ is determined. The ratio (inhibition ratio) of the $IC_{50}$ of the test compound based on the transient sodium current against the corresponding $IC_{50}$ based on the persistent sodium current will serve as an indicator of the selectivity of the agent. The compound, to be useful for the purpose of this invention, should have an inhibition ratio of at least 4 or more, more preferably 7 or more, still more preferably 10 or more, most preferably 20 or more.

In order to efficiently select potent compounds for selectively blocking the persistent sodium current to be useful in this invention, it is possible to combine the above method as appropriate with other pharmacological tests. For example, such combination may be properly selected referring to the following examples.

Process 1: the test compound is tested for its inhibitory effect on the binding of batrachotoxin to receptors in the synaptosome, for example, as in Experiment Example 1 of this invention described below.

Process 2: the test compound is tested for its inhibitory effect on the vetratridine-induced contracture of an isolated myocardial cell and its $IC_{50}$ is determined as in Example 2, and/or, for its inhibitory effect on the veratridine-induced rise in intracellular sodium concentration of a nerve cell and its $IC_{50}$ is determined as in Experiment Example 3.

Process 3: the test compound is tested for its inhibitory effect on the nociceptive response in the formalin test in an experimental animal model, for example, as in Experiment Example 4.

Process 4: the test compound is determined of its amount necessary for selectively raising (without affecting the threshold of the normal nerve) the threshold to a mechanical stimulus applied to an injured sciatic nerve which has been loosely constricted and whose threshold to stimuli has been lowered on account of the injury, according to the Bennett's method as in Experiment Example 5.

Process 5: the test compound is determined how selectively it inhibits the persistent sodium current of a nerve cell, using the voltage-clamp method, for example, as in Experiment 6.

Processes 4 and 5 may be reversed in their order.

As those who are skilled in the art readily understand, if compounds are screened based on the results obtained from these Experiments, it will be possible to obtain the potent compounds which will present with a desired profile.

It will be also possible for those who are skilled in the art to add, as far as permitted to their skill, other in vitro or in vivo pharmacological tests as appropriate to the screening methods described above, or to replace parts of the latter with the former, without departing from the scope of this invention.

The compound of this invention represented by Formula (I) will be described below.

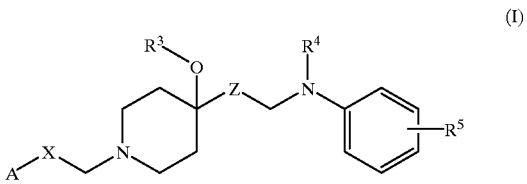

(I)

(wherein A represents phenyl group or monocyclic aromatic heterocylic ring each substituted by $R^1$ and $R^2$; $R^1$ and $R^2$ represent, independently of each other, a group arbitrarily selected from the group of hydrogen atom, halogen atom, trifluoromethyl group, trifluoromethoxy group, nitro group, cyano group, lower alkoxycarbonyl group, amino group unsubstituted or mono- or di-substituted by lower alkyl groups, carbamoyl group unsubstituted or mono- or di-substituted by lower alkyl groups, sulfamoyl group unsubstituted or mono- or di-substituted by lower alkyl groups, unprotected or protected hydroxyl group, unprotected or protected carboxyl group, lower alkoxy group, lower alkyl group, lower alkylthio group, lower alkylsulfinyl group, lower alkylsulfonyl group and lower alkanoyl group; $R^3$ represents hydrogen atom or a lower alkyl group; $R^4$ represents hydrogen atom or a lower alkyl group; $R^5$ represents ethoxy group or isopropoxy group; X represents a group: —CH(OH)— or methylene group; and Z represents a single bond or methylene group unsubstituted or substituted by unprotected or protected hydroxyl group).

The groups described in the formula in this invention are defined as follows.

The "monocyclic aromatic heterocyclic ring" means 5-membered or 6-membered aromatic rings comprising one to two hetero atoms, and includes, for example, pyrrolyl group, furyl group, thienyl group, imidazolyl group, oxazolyl group, thiazolyl group, pyridyl group, pyrimidinyl group, etc.

The "halogen atom" includes fluorine atom, chlorine atom, bromine atom, and iodine atom.

The "lower" means a straight, branched or cyclic carbon chain containing one to three carbons unless otherwise stated. Accordingly, the "lower alkyl group" includes a methyl group, ethyl group, propyl group, isopropyl group, and cyclopropyl group.

The "lower alkoxy group" includes methoxy group, ethoxy group, propoxy group, isopropoxy group, and cyclopropyloxy group.

The "lower alkylthio group" includes methylthio group, ethylthio group, propylthio group, isopropylthio group, and cyclopropylthio group.

The "lower alkylsulfinyl group" includes methylsulfinyl group, ethylsulfinyl group, propylsulfinyl group, isopropylsulfinyl group, and cyclopropylsulfinyl group.

The "lower alkylsulfonyl group" includes methylsulfonyl group, ethylsulfonyl group, propylsulfonyl group, isopropylsulfonyl group, and cyclopropylsulfonyl group.

The "lower alkoxycarbonyl group" includes methoxycarbonyl group, ethoxycarbonyl group, propoxycarbonyl group, isopropoxycarbonyl group and cyclopropyloxycarbonyl group.

The "amino group unsubstituted or mono- or di-substituted by lower alkyl groups" means an amino group of which one or two hydrogen atoms may be substituted by the aforementioned "lower alkyl group." Specifically, it includes amino group, methylamino group, ethylamino group, propylamino group, isopropylamino group, cyclopropylamino group, dimethylamino group, diethylamino group, dipropylamino group, diisopropylamino group, ethylmethylamino group, methylpropylamino group, ethylpropylamino group, etc.

The "carbamoyl group unsubstituted or mono- or di-substituted by lower alkyl groups" means a carbamoyl group of which one or two hydrogen atoms bound on nitrogen atom may be substituted by the aforementioned "lower alkyl group." Specifically, it includes carbamoyl group, methylcarbamoyl group, ethylcarbamoyl group, propylcarbamoyl group, isopropylcarbamoyl group, cyclopropylcarbamoyl group, dimethylcarbamoyl group, diethylcarbamoyl group, ethylmethylcarbamoyl group, methylpropylcarbamoyl group, etc.

The "sulfamoyl group unsubstituted or mono- or di-substituted by lower alkyl groups" means sulfamoyl group of which one or two hydrogen atoms bound on nitrogen atom of the sulfamoyl group may be substituted by the aforementioned "lower alkyl group." Specifically, it includes a sulfamoyl group, methysulfamoyl group, ethylsulfamoyl group, propylsulfamoyl group, isopropylsulfamoyl group, cyclopropylsulfamoyl group, dimethylsulfamoyl group, diethysulfamoyl group, ethylmethylsufamoyl group, methylpropylsulfamoyl group, etc.

The "lower alkanoyl group" includes a formyl group, acetyl group, propionyl group, etc.

The protective group used in "unprotected or protected hydroxyl group" as described in this specification includes alkyl protective groups such as a methyl group, tert-butyl group, benzyl group, trityl group, methoxymethyl group, etc.; silyl protective groups such as a trimethylsilyl group, tert-butyldimethylsilyl group, etc.; acyl protective groups such as a formyl group, acetyl group, benzoyl group, etc.; and carbonate protective groups such as methoxycarbonyl group, benzyloxycarbonyl group, etc.

The protective group used in "unprotected or protected carboxyl group" as described in this specification includes alkyl ester protective groups such as a methyl group, ethyl group, tert-butyl group, benzyl group, diphenylmethyl group, trityl group, etc.; and silyl ester protective groups such as a trimethylsilyl group, tert-butyldimethylsilyl group, etc.

The preferred substituents for the compound of this invention are as follows.

A is preferably phenyl group, furyl group, thienyl group or pyridyl group, more preferably a phenyl group, furyl group or thienyl group, still more preferably a phenyl group.

$R^1$ is preferably hydrogen atom, fluorine atom, chlorine atom, bromine atom, trifluoromethyl group, trifluoromethoxy group, nitro group, cyano group, methoxycarbonyl group, ethoxycarbonyl group, dimethylamino group, carbamoyl group, dimethylcarbamoyl group, sulfamoyl group, hydroxyl group, carboxyl group, methoxy group, methyl group, methylthio group, methylsulfinyl group, methylsulfonyl group, or acetyl group, more preferably hydrogen atom, fluorine atom, chlorine atom, trifluoromethyl group, trifluoromethoxy group, nitro group, cyano group, methoxycarbonyl group, methoxy group, methyl group, methylthio group, or acetyl group, still more preferably hydrogen atom, fluorine atom, chlorine atom, trifluoromethyl group, nitro group, cyano group, or methyl group. Particularly, hydrogen atom, fluorine atom, chlorine atom, or cyano group is preferred.

$R^2$ is preferably hydrogen atom, fluorine atom or chlorine atom, more preferably hydrogen atom.

The combination of $R^1$ and $R^2$ preferably occurs between hydrogen atom, fluorine atom, chlorine atom, trifluoromethyl group, trifluoromethoxy group, nitro group, cyano group, methoxycarbonyl group, methoxy group, methyl group, methylthio group or acetyl group as $R^1$, and hydrogen atom as $R^2$, more preferably between hydrogen atom, fluorine atom, chlorine atom, trifluoromethyl group, nitro group, cyano group or methyl group as $R^1$, and hydrogen atom as $R^2$.

$R^3$ is preferably hydrogen atom or methyl group, more preferably hydrogen atom.

$R^4$ is preferably hydrogen atom or methyl group, more preferably methyl group.

$R^5$ is preferably isopropoxy group.

$R^5$ preferably has its substitution position at a para position (4th position) with respect to —$NR^4$—.

X is preferably methylene group.

Z is preferably methylene group.

The preferred combinations of the substituents in the compound are as follows. A represents phenyl group, furyl group or thienyl group each substituted by $R^1$ and $R^2$, wherein $R^1$ is hydrogen atom, fluorine atom, chlorine atom, trifluoromethyl group, trifluoromethoxy group, nitro group, cyano group, methoxycarbonyl group, methoxy group, methyl group, methylthio group, or acetyl group while $R^2$ is hydrogen atom; $R^3$ represents hydrogen atom or methyl group; $R^4$ represents hydrogen atom or methyl group; $R^5$ represents ethoxy group or isopropoxy group; X represents a group: —CH(OH)— or methylene group; and Z represents a single bond or methylene group unsubstituted or substituted by hydoxyl group. More preferably, A is a phenyl group substituted by $R^1$ and $R^2$, or unsubstituted furyl group or unsubstituted thienyl group, wherein $R^1$ is hydrogen atom, fluorine atom, chlorine atom, trifluoromethyl group, nitro group, cyano group, or methyl group, while $R^2$ is hydrogen atom; $R^3$ represents hydrogen atom or methyl group; $R^4$ represents hydrogen atom or methyl group; $R^5$ represents ethoxy group or isopropoxy group which has its binding site at a para position (4th position) with respect to —$NR^4$—; X represents a group: —CH(OH)— or methylene group; and Z represents a single bond or methylene group unsubstituted or substituted by hydoxyl group.

The preferred compound includes followings.

4-[2-[N-methyl-N-(4-isopropoxyphenyl)amino]ethyl]-1-(2-phenylethyl)piperidin-4-ol 1-[2-(4-cyanophenyl)ethyl]-4-[2-[N-methyl-N-(4-isopropoxyphenyl)amino]ethyl]piperidin-4-ol 1-[2-(4-fluorophenyl)ethyl]-4-[2-[N-methyl-N-(4-isopropoxyphenyl)amino]ethyl]piperidin-4-ol 4-[2-[N-methyl-N-(4-isopropoxyphenyl)amino]ethyl]-1-[2-(4-nitrophenyl)ethyl]piperidin-4-ol 1-[2-(3-cyanophenyl)ethyl]-4-[2-[N-methyl-N-(4-isopropoxyphenyl)amino]ethyl]piperidin-4-ol 1-[2-(3-fluorophenyl)ethyl]-4-[2-[N-methyl-N-(4-isopropoxyphenyl)amino]ethyl]piperidin-4-ol 1-[2-(2-fluorophenyl)ethyl]-4- [2-[N-methyl-N-(4-isopropoxyphenyl)amino]ethyl]piperidin-4-ol 1-[2-(4-chlorophenyl)ethyl]-4-[2-[N-methyl-N-(4-isopropoxyphenyl)amino]ethyl]piperidin-4-ol 1-[2-(3-chlorophenyl)ethyl]-4-[2-[N-methyl-N-(4-isopropoxyphenyl)amino]ethyl]piperidin-4-ol 1-[2-(2-chlorophenyl)ethyl]-4-[2-(N-methyl-N-(4-isopropoxyphenyl)amino]ethyl]piperidin-4-ol 4-[2-[N-methyl-N-(4-isopropoxyphenyl)amino]ethyl]-1-[2-[4-(trifluoromethyl)phenyl]ethyl]piperidin-4-ol 4-[2-[N-methyl-N-(4-isopropoxyphenyl)amino]ethyl]-1-[2-[3-(trifluoromethyl)phenyl]ethyl]piperidin-4-ol 4-[2-[N-methyl-N-(4-isopropoxyphenyl)amino]ethyl]-1-[2-[2-(trifluoromethyl)phenyl]ethyl]piperidin-4-ol 4-[2-[N-methyl-N-(4-isopropoxyphenyl)amino]ethyl]-1-[2-(4-methylphenyl)ethyl]piperidin-4-ol 4-[2-[N-methyl-N-(4-isopropoxyphenyl)amino]ethyl]-1-[2-(2-methylphenyl)ethyl]piperidin-4-ol 1-[2-(4-fluorophenyl)-2-hydroxyethyl]-4-[2-[N-methyl-N-(4-isopropoxyphenyl)amino]ethyl]piperidin-4-ol 1-[2-(3-furyl)ethyl]-4-[2-[N-methyl-N-(4-isopropoxyphenyl)amino]ethyl]piperidin-4-ol 4-[2-[N-methyl-N-(4-isopropoxyphenyl)amino]ethyl]-1-[2-(2-thienyl)ethyl]piperidin-4-ol 1-[2-(4-cyanophenyl)ethyl]-4-[2-[N-(4-ethoxyphenyl)-N-methylamino]ethyl]piperidin-4-ol 1-[2-(4-cyanophenyl)ethyl]-4-[2-[N-(4-isopropoxyphenyl)amino]ethyl]piperidin-4-ol 1-[2-(4-cyanophenyl)ethyl]-4-[2-[N-methyl-N-(4-isopropoxyphenyl)amino]-1-hydroxyethyl]piperidin-4-ol 1-[2-(4-cyanophenyl)ethyl]-4-methoxy-4-[2-[N-methyl-N-(4-isopropoxyphenyl)amino]ethyl]piperidine 1-[2-(4-cyanophenyl)ethyl]-4-[N-methyl-N-(4-isopropoxyphenyl)aminomethyl]piperidin-4-ol These compounds can form the salts described below.

The compound of this invention may contain asymmetric carbon atoms in its structure, and thus its various isomers optically active or inactive including stereoisomers (enanthiomers and diastereoisomers, etc.), geometrical isomers and tautomeric isomers, etc., and their mixtures and isolated single compounds are also included in this invention. Separation of such a stereoisomer from other isomers, and its purification can be achieved by any person that has an ordinary skill in the art using such techniques as differential crystallization, or optical resolution by column chromatography or asymmetric synthesis.

The compound (I) of this invention may form acid-bound salts, or may form salts with bases, depending on the nature of its substituents. The salts are not limited to any specific ones, as long as they are pharmaceutically acceptable. Specifically, they include acid-bound salts, the acid being a mineral acid such as hydrochloric acid, hydrobromic acid, hydroiodic acid, sulfuric acid, nitric acid, phosphoric acid, etc.; an organic carboxylic acid such as acetic acid, propionic acid, oxalic acid, malonic acid, succinic acid, fumalic acid, maleic acid, lactic acid, formic acid, malic acid, tartaric acid, citric acid, mandelic acid, etc.; an organic sulfonic acid such as methanesulfonic acid, ethanesulfonic acid, benzenesulfonic acid, p-toluenesulfonic acid, 2-hydroxyethanesulfonic acid, etc.; or an acidic amino acid such as aspartic acid, glutamic acid, etc. The compound may form salts with bases, the base being alkali metal or alkaline earth metal such as sodium, potassium, magnesium, calcium, or aluminum; organic bases such as methylamine, ethylamine, ethanolamine, pyridine, lysine, arginine, ornithine, etc.; or ammonium salts.

The above salt can be prepared according to convention: for example, a solution of a compound of this invention and a solution of a desired acid or base at equivalent amounts are mixed and the resulting salt is collected by filtration, or through the evaporation of the solvent. Further, the compound of this invention or its salts can form a solvate in the presence of a solvent such as water, ethanol, glycerol, etc.

The salts of the compounds of the present invention may contain mono- or di-salts. The compounds of the present invention may simultaneously form both acid addition salt and salt with a base depending on the substituent on the side chains of the compounds.

Moreover, this invention includes the hydrates, various pharmaceutically acceptable solvate and polymorphic crystals of compound (I). Naturally, this invention is not limited to the compounds mentioned in the Examples below, but include all the compounds represented by Formula (I), and their pharmaceutically acceptable salts.

Next, the method for manufacturing the compound of this invention will be disclosed and the processes involved therein will be described. The definitions of A, $R^3$, $R^4$, $R^5$, W, P, Q, X, Y, Z and Z' in Formulas (I), (I)-a, (VI'), (VII'), (IX), (X'), (XI), (XII) and (XIII) cited in the Reaction Schemes and the description of Manufacturing Methods 1 to 4 are the same meanings as above, unless otherwise stated.

The compound of this invention represented by Formula (I), or its salts can be prepared according to Manufacturing Methods 1 to 4 described below or to their modifications from compounds as represented by Formula (III) (wherein $R^4$ and $R^5$ have the same meanings as defined above), Formula (IV) (wherein A, $R^3$, X, Y and Z have the same meanings as defined above), Formula (V) (wherein $R^3$, P and Z have the same meanings as defined above), Formulas (XI) to (XIII), Formula (XIV) (wherein A, $R^3$, X, Y and Z have the same meanings as defined above), Formula (XV) (wherein $R^3$, P and Z have the same meanings as defined above), Formula (XVII) (wherein A, X and Y have the same meanings as defined above), or Formula (XVIII) (wherein P has the same meanings as defined above), which may be synthesized starting from the compounds known in the art or from commercially available compounds. As the starting material, intermediate material and product of each process, the salt of a relevant compound may be used as needed.

Next, the manufacturing processes will be described in detail.

Manufacturing Method 1

It is possible to prepare a compound represented by Formula (I) or its salt, from a compound represented by Formula (III), and another compound represented by Formula (IV) or Formula (V), by employing appropriate processes cited in Reaction Scheme 1.

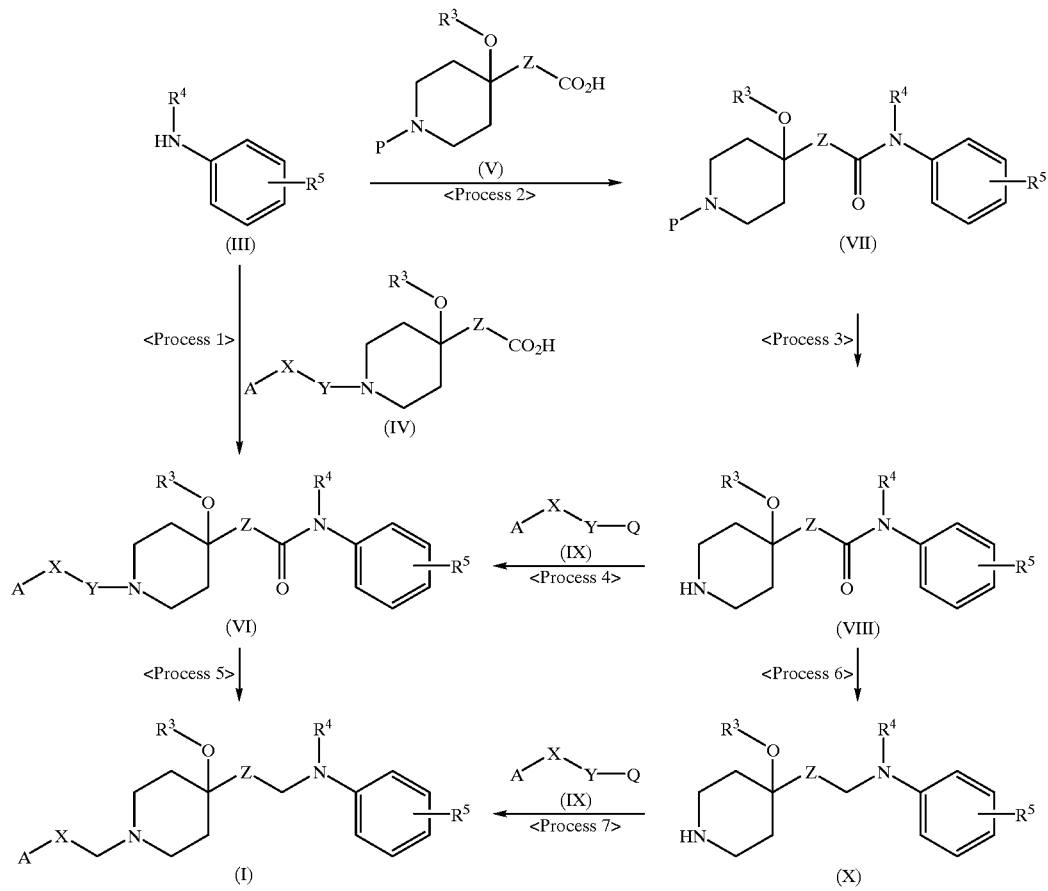

Reaction Scheme 1

Process 1

It is possible to obtain a compound represented by Formula (VI) (wherein $R^3$, $R^4$, $R^5$, A, X, Y and Z have the same meanings as defined above), by allowing a compound represented by Formula (III) to react with another compound represented by Formula (IV) in a solvent not interfering with the reaction, for example, chosen from the group comprising halogenated hydrocarbon solvents such as methylene chloride, chloroform, etc., ether solvents such as diethyl ether, tetrahydrofuran, etc., hydrocarbon solvents such as benzene, hexane, etc., and polar solvents such as dimethylformamide, dimethyl sulfoxide, etc., in the presence of a condensing agent such as 1-ethyl-3-(3-dimethylaminopropyl)carbodiimide hydrochloride (water soluble carbodiimide hydrochloride, WSC.HCl) or dicyclohexylcarbodiimide (DCC), at a temperature between 0° C. and the temperature at which the reaction mixture will reflux.

Alternatively, it will be possible to elicit the above reaction by allowing the two compounds to react in a solvent not interfering with the reaction, for example, chosen from the group comprising halogenated hydrocarbon solvents such as methylene chloride, chloroform, etc., ether solvents such as diethyl ether, tetrahydrofuran, etc., and hydrocarbon solvents such as benzene, hexane, etc., in the presence of a dehydrating agent such as phosphorus oxychloride and of a base such as pyridine, triethylamine, etc., at a temperature between −20° C. and the temperature at which the reaction mixture will reflux.

It is also possible to obtain a compound represented by Formula (VI), by converting a compound represented by Formula (IV) into an acyl chloride using thionyl chloride or the like, and then by allowing the acyl chloride to react with a compound represented by Formula (III) in a solvent chosen from the group comprising halogenated hydrocarbon solvents such as methylene chloride, chloroform, etc., ether solvents such as diethyl ether, tetrahydrofuran, etc., hydrocarbon solvents such as benzene, hexane, etc., and basic solvents such as pyridine, triethylamine, etc., in the presence of an organic base such as triethylamine, pyridine, etc. or of an inorganic base such as potassium carbonate or the like, at a temperature between −20° C. and the temperature at which the reaction mixture will reflux.

It is also possible to obtain a compound represented by Formula (VI) according to Processes 2, 3 and 4 described below.

Process 2

It is possible to prepare a compound represented by Formula (VII) (wherein $R^3$, $R^4$, $R^5$, P and Z have the same meanings as defined above) from a compound represented by Formula (III) and another compound represented by Formula (V) according to Process 1. The protective group P includes alkyl protective groups such as benzyl group, trityl group, methoxymethyl group, etc., and carbamate protective groups such as tert-butoxycarbonyl group, benzyloxycarbonyl group, etc., as described in T. W. Green and P. G. M. Wuts (eds.), "Protective Groups in Organic Synthesis," 3rd Ed., John Wiley and Sons, 1999.

Process 3

It is possible to obtain a compound represented by Formula (VIII) (wherein $R^3$, $R^4$, $R^5$ and Z have the same meanings as defined above) by removing the protective group at the 1st position of piperidine from a compound represented by Formula (VII).

Removal of the protective group at the 1st position of piperidine from a compound represented by Formula (VII) may be achieved by a method introduced in the above review, i.e., "Protective Groups in Organic Synthesis," 3rd Ed., 1999. For example, if the protective group is a benzyl group, benzyloxycarbonyl group or the like, removal of the protective group will be achieved by placing the compound in an alcoholic solvent such as methanol, ethanol, etc., or ethyl acetate, acetic acid or water under hydrogen atmosphere, or in the presence of ammonium formate in the presence of a catalyst such as palladium on carbon, platinum oxide, etc., at a temperature between 0° C. and the temperature at which the reaction mixture will reflux. Then, a compound represented by Formula (VIII) will be obtained. If the protective group is a tert-butoxycarbonyl group or the like, removal of the protective group will be achieved by placing the compound in acid such as trifluoroacetic acid, hydrochloric acid, etc., in the presence or absence of anisole at a temperature between 0° C. and the temperature at which the reaction mixture will reflux. Then, a compound represented by Formula (VIII) will be obtained.

Process 4

It is possible to allow a compound represented by Formula (VIII) to react with another compound represented by Formula (IX) according to the method described below appropriately chosen depending on the nature of —Y—Q.

Method A

If —Y and Q together represent halogenated alkyl group, compounds represented by Formulas (VIII) and (IX) are placed in a solvent not interfering with the reaction, for example, chosen from the group comprising halogenated hydrocarbon solvents such as methylene chloride, chloroform, etc., ether solvents such as diethyl ether, tetrahydrofuran, etc., hydrocarbon solvents such as benzene, hexane, etc., and polar solvents such as dimethylformamide, dimethyl sulfoxide, etc., in the presence or absence of an organic base such as triethylamine, pyridine, etc., or of an inorganic base such as potassium carbonate, etc., at a temperature between 0° C. and the temperature at which the reaction mixture will reflux. Then, a compound represented by Formula (VI) will be obtained. For this reaction, sodium iodide may be used as a catalyst.

Method B

If —Y and Q together represent aldehyde, compounds represented by Formulas (VIII) and (IX) are placed in a solvent, for example, chosen from the group comprising aromatic hydrocarbon solvents such as toluene, benzene, etc., halogenated hydrocarbon solvents such as methylene chloride, chloroform, etc., and alcoholic solvents such as methanol, ethanol, etc., in the presence or absence of an acidic catalyst such as acetic acid, etc., in combination with an appropriate reducing agent. Then, a compound represented by Formula (VI) will be obtained. Generally speaking, for this reaction, any reducing agent that can reduce an imino group into an amino group is applicable, but the preferred reducing agent includes sodium triacetoxyborohydride, sodium borohydride, lithium borohydride, diisobutylaluminum hydride, sodium cyanoborohydride, etc. The reducing reaction may proceed at a temperature between −78° C. and room temperature, preferably at room temperature, for a period which will allow, a sufficient amount of the reaction product to form, specifically, a period between 3 and 12 hours.

Method C

If —Y and Q together represent carboxylic acid, it is possible to prepare a compound represented by Formula (VI) according to Process 1.

Process 5

It is possible to obtain a compound represented by Formula (I) or its salts, by allowing a compound represented by Formula (VI) to react with a reducing agent such as lithium aluminum hydride or diisobutylaluminum hydride, or a borane complex represented by borane-methyl sulfide or borane-tetrahydrofuran, in a solvent not interfering with the reaction, for example, chosen from the group comprising ether solvents such as diethyl ether, tetrahydrofuran, etc., and aromatic hydrocarbon solvents such as toluene, benzene, etc., at a temperature between 0° C. and the temperature at which the reaction mixture will reflux. If a compound represented by Formula (VI) has a carbonyl group as Y, the carbonyl group will be also reduced through the same reducing reaction into a methylene group.

It is possible to obtain a compound represented by Formula (I) or its salts by processing a compound represented by Formula (VIII) according to Processes 6 and 7 described below.

Process 6

It is possible to prepare a compound represented by Formula (X) (wherein $R^3$, $R^4$, $R^5$ and Z have the same meanings as defined above), by processing a compound represented by Formula (VIII) according to Process 5.

It is also possible to prepare a compound represented by Formula (X), by reducing a compound represented by Formula (VII) according to Process 5, and then by removing the protective group inserted at the 1st position of piperidine from the resulting compound according to Process 3.

Process 7

It is possible to prepare a compound represented by Formula (I) from compounds represented by Formulas (X) and (IX). If, of a compound represented by Formula (IX), —Y and Q together represent halogenated alkyl group, preparation of the compound in question will be achieved by Method A of Process 4. If —Y and Q together represents aldehyde, the desired preparation will be achieved by Method B of Process 4. If —Y and Q together represent carboxylic acid, it is possible to obtain a compound represented by Formula (I) by processing the above starting compounds by Method C of Process 4, and then by reducing the amide bond formed in the resulting compound by Process 5.

Manufacturing Method 2

The manufacture of a compound represented by Formula (I)-a which is the same with Formula (I) except for Z' replacing Z, will be described below.

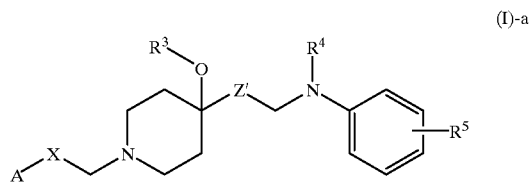

(I)-a

It is possible to prepare a compound represented by Formula (I)-a or its salts from a compound represented by Formula (XI), and another compound represented by Formula (XII) or Formula (XIII), by employing appropriate processes cited in Reaction Scheme 2.

Reaction Scheme 2

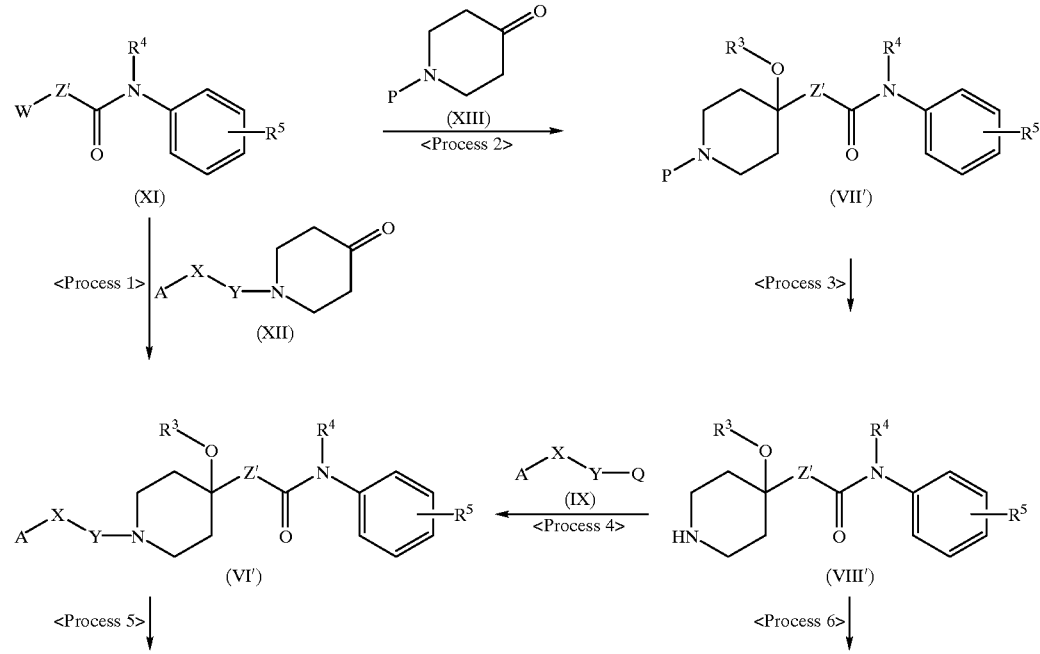

-continued

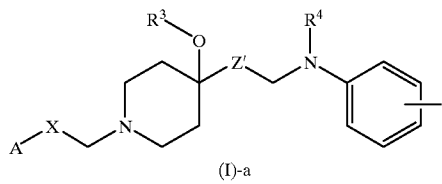

(I)-a

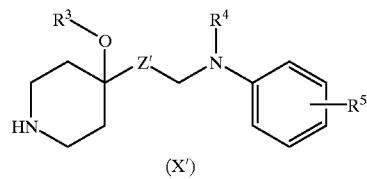

(X')

Process 1

It is possible to obtain a compound represented by Formula (VI') by binding a compound represented by Formula (XI) to another compound represented by Formula (XII), and then by alkylating the hydroxyl group of the resulting compound as needed. If in a compound represented by Formula (XI), W represents hydrogen atom, it is possible to achieve the addition reaction by allowing a compound represented by Formula (XI) to react with a metal amide reagent such as lithium diisopropylamide, lithium hexamethyldisilazide, potassium hexamethyldisilazide, etc., or of an organic metal reagent represented by tin (II) triflate or the like in a solvent not interfering with the reaction, for example, chosen from the group comprising ether solvents such as diethyl ether, tetrahydrofuran, etc., and hydrocarbon solvents such as benzene, hexane, etc., at a temperature between −100° C. and room temperature, to turn the compound into a metal enolate, and then by allowing the enolate to react with a compound represented by Formula (XII) at a temperature between −100° C. and room temperature.

If in a compound represented by Formula (XI) W represents halogen atom, or more preferably a bromine atom, elicitation of the addition reaction will be achieved by allowing a compound represented by Formula (XI) to react with zinc powder in a solvent not interfering with the reaction, for example, chosen from the group comprising ether solvents such as diethyl ether, tetrahydrofuran, etc., and hydrocarbon solvents such as benzene, hexane, etc., to turn the compound into a zinc compound, and then by allowing the zinc compound to react with a compound represented by Formula (XII).

Alkylation of the tertiary hydroxyl group of the compound resulting from the above addition reaction may be achieved by placing the compound in a solvent not interfering with the reaction such as dimethylformamide or dimethylimidazolidone, in the presence of a base such as sodium hydride, etc., in combination with an alkylating agent such as alkyl halide, for example, methyl iodide, or alkyl sulfate, for example, dimethyl sulfate, at a temperature between −20° C. and the temperature at which the reaction mixture will reflux, or more preferably at a temperature between ice-cooled temperature and room temperature.

It is also possible to obtain a compound represented by Formula (VI') according to Processes 2, 3 and 4 described below.

Process 2

It is possible to prepare a compound represented by Formula (VII') from compounds represented by Formulas (XI) and (XIII) according to Process 1.

Process 3

It is possible to prepare a compound represented by Formula (VIII') (wherein $R^3$, $R^4$, $R^5$ and Z' have the same meanings as defined above) from a compound represented by Formula (VII') according to Process 3 of Manufacturing Method 1.

Process 4

It is possible to prepare a compound represented by Formula (VI') from compounds represented by Formulas (VIII') and (IX) according to Process 4 of Manufacturing Method 1.

Process 5

It is possible to prepare a compound represented by Formula (I)-a or its salts from a compound represented by Formula (VI') according to Process 5 of Manufacturing Method 1.

Alternatively, it is possible to prepare a compound represented by Formula (I)-a or its salts from a compound represented by Formula (VIII') according to Processes 6 and 7.

Process 6

It is possible to prepare a compound represented by Formula (X') from a compound represented by Formula (VIII') according to Process 5.

Alternatively, it is possible to obtain a compound represented by Formula (X') by reducing a compound represented by Formula (VII') according to Process 5, and then by removing the protective group inserted at the 1st position of piperidine from the resulting compound according to Process 3.

Process 7

It is possible to prepare a compound represented by Formula (I)-a or its salts from compounds represented by Formulas (X') and (IX) according to Process 7 of Manufacturing Method 1.

Manufacturing Method 3

It is possible to prepare a compound represented by Formula (I) or its salts from a compound represented by Formula (III), and another compound represented by Formula (XIV) or Formula (XV), by employing appropriate processes cited in Reaction Scheme 3.

Reaction Scheme 3

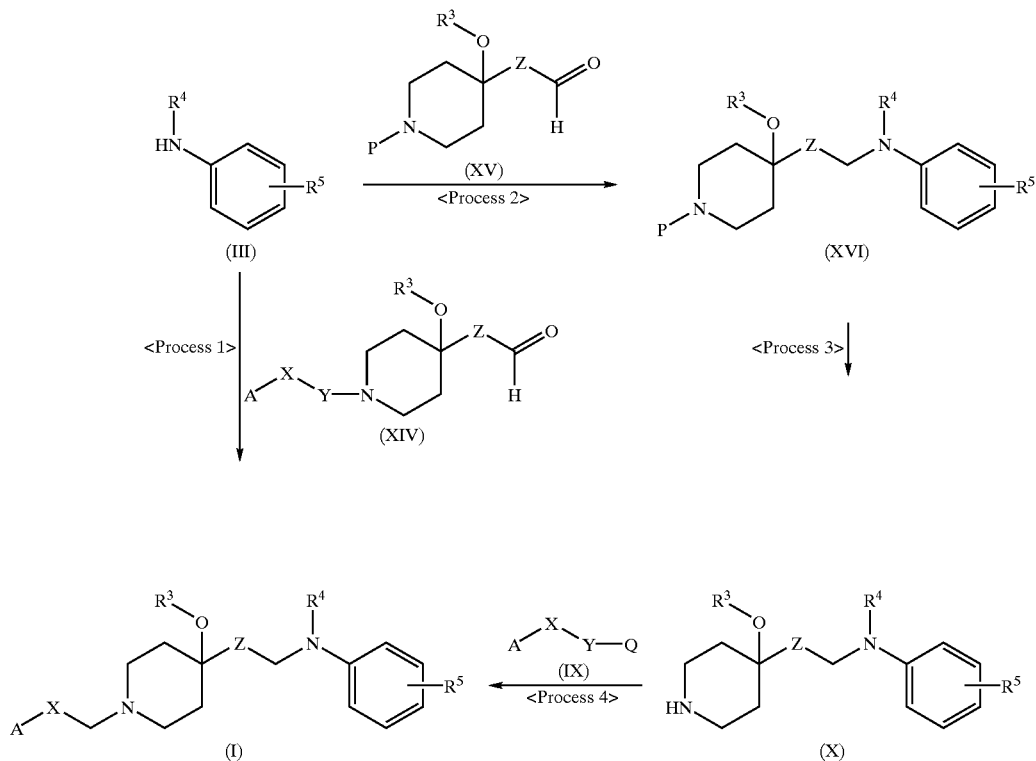

Process 1

It is possible to prepare a compound represented by Formula (I) or its salts from compounds represented by Formulas (III) and (XIV) according to Process 4 of Manufacturing Method 1.

If Y represents a carbonyl group, the resulting compound should be immediately submitted to Process 5 of Manufacturing Method 1 so that its amide group may be reduced. Then, a compound represented by Formula (I) is obtained.

Alternatively, it is possible to obtain a compound represented by Formula (I) or its salts by employing Processes 2, 3 and 4 described below.

Process 2

It is possible to prepare a compound represented by Formula (XVI) (wherein $R^3$, $R^4$, $R^5$, P and Z have the same meanings as defined above) from compounds represented by Formulas (III) and (XV) according to Process 1.

Process 3

It is possible to prepare a compound represented by Formula (X) from a compound represented by Formula (XVI) according to Process 3 of Manufacturing Method 1.

Process 4

It is possible to prepare a compound represented by Formula (I) or its salts from compounds represented by Formulas (X) and (IX) according to Process 7 of Manufacturing Method 1.

Manufacturing Method 4

The manufacture of a compound represented by Formula (I)-b which is the same with Formula (I) except for Z representing a single bond, will be described below.

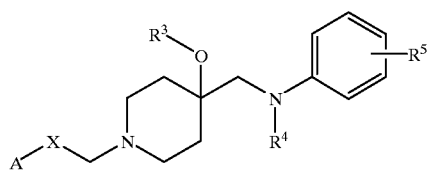

(I)-b

It is possible to prepare a compound represented by Formula (I)-b (wherein A, $R^3$, $R^4$, $R^5$ and X have the same meanings as defined above) or its salts from a compound represented by Formula (III), and another compound represented by Formula (XVII) or Formula (XVIII), by employing appropriate processes cited in Reaction Scheme 4.

Reaction Scheme 4

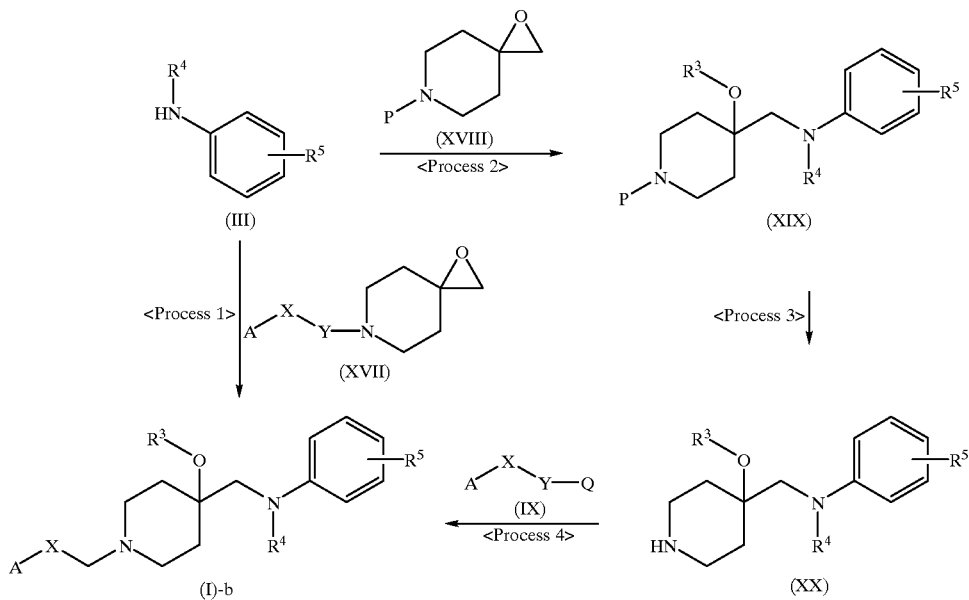

Process 1

It is possible to obtain a compound represented by Formula (I)-b or its salts by allowing a compound represented by Formula (III) to react with another compound represented by Formula (XVII) in a solvent not interfering with the reaction, for example, chosen from the group comprising halogenated hydrocarbon solvents such as methylene chloride, chloroform, etc., ether solvents such as diethyl ether, tetrahydrofuran, etc., hydrocarbon solvents such as benzene, hexane, etc., and polar solvents such as dimethylformamide, dimethyl sulfoxide, etc., in the presence of an acidic or basic catalyst, at a temperature between 0° C. and the temperature at which the reaction mixture will reflux. Alternatively, it is possible to obtain the same compound by allowing the same starting materials to react in diethyl ether in the presence of a neutral alumina at room temperature, according to the method described in Gary H. Posner et al., Journal of the American Chemical Society, 99:8208–8214, 1977.

If Y represents a carbonyl group, the resulting compound should be immediately submitted to Process 5 of Manufacturing Method 1 so that its amide group may be reduced. Then, a compound represented by Formula (I)-b will be obtained.

Alternatively, it is possible to obtain a compound represented by Formula (I)-b or its salts by employing Processes 2, 3 and 4.

Process 2

It is possible to prepare a compound represented by Formula (XIX) (wherein $R^3$, $R^4$, $R^5$ and P have the same meanings as defined above) from compounds represented by Formulas (III) and (XVIII) according to Process 1.

Process 3

It is possible to prepare a compound represented by Formula (XX) (wherein $R^3$, $R^4$, and $R^5$ have the same meanings as defined above) from a compound represented by Formula (XIX) according to Process 3 of Manufacturing Method 1.

Process 4

It is possible to prepare a compound represented by Formula (I)-b or its salts from compounds represented by Formulas (XX) and (IX), according to Process 7 of Manufacturing Method 1.

If the compounds prepared by the above processes have the structures represented by Formulas (I), (I)-a, (I)-b, (XVI), and (XIX) wherein $R^4$ represents hydrogen atom, it is possible to convert them to compounds represented by the corresponding formulas wherein $R^4$ represents a lower alkyl group, by subjecting the compound to alkylation using an alkylating agent such as alkyl halide, for example, methyl iodide, or alkyl sulfate, for example, dimethyl sulfate, in a solvent not interfering with the reaction, for example, chosen from the group comprising halogenated hydrocarbon solvents such as methylene chloride, chloroform, etc., ether solvents such as diethyl ether, tetrahydrofuran, etc., hydrocarbon solvents such as benzene, hexane, etc., and polar solvents such as dimethylformamide, dimethyl sulfoxide, etc., in the presence or absence of an inorganic base such as potassium hydroxide, sodium hydride, potassium carbonate, etc., or of an organic base such as triethylamine, pyridine, etc., at a temperature between 0° C. and the temperature at which the reaction mixture will reflux. Alternatively, it is possible to prepare the compound in which $R^4$ represents lower alkyl group by using aldehydes or ketones according to Method B in Process 4 of Manufacturing Method 1. Alternatively, it is possible to prepare the compound in which $R^4$ represents lower alkyl group, by acylating with carboxylic acid derivative according to Process 1 of Manufacturing Method 1, and then by reducing the resulting compound according to Process 5 of Manufacturing Method 1.

If the compound prepared as above has the structure represented by Formula (VI), (VII), (VI') or (VII') wherein R⁴ represents hydrogen atom, it is possible to convert it to a compound represented by the corresponding formula wherein R⁴ represents lower alkyl group, by subjecting the compound to alkylation using an alkylating agent such as alkyl halide, for example, methyl iodide, or alkyl sulfate, for example, dimethyl sulfate, in a solvent not interfering with the reaction, for example, chosen from the group comprising halogenated hydrocarbon solvents such as methylene chloride, chloroform, etc., ether solvents such as diethyl ether, tetrahydrofuran, etc., hydrocarbon solvents such as benzene, hexane, etc., and polar solvents such as dimethylformamide, dimethyl sulfoxide, etc., in the presence of a base such as potassium hydroxide, sodium hydride, etc., at a temperature between 0° C. and the temperature at which the reaction mixture will reflux.

If the compound prepared as above has the structure represented by Formula (I), (I)-a, (I)-b, (VI), (VII), (VI'), (VII'), (XVI) or (XIX) which has an alkoxy group as a substituent on its benzene ring, it is possible to obtain another alkoxy group-substituted derivative from the compound, by dealkylation using boron tribromide, hydrogen bromide in acetic acid or the like, and then by subjecting the resulting compound to alkylation using one of the aforementioned alkylating agents in a solvent not interfering with the reaction such as dimethylformamide, dimethylimidazolidone or the like, in the presence of a base such as sodium hydride, at a temperature between −20° C. and the temperature at which the reaction mixture will reflux, or more preferably at a temperature between ice-cooled temperature and room temperature.

The compounds prepared as above by the aforementioned processes may be converted to another during process, according to the methods described below.

If the compound has a structure represented by one of the above formulas wherein X represents a carbonyl group, it is possible to convert, as needed, the compound to another compound wherein X is group: —CH(OH)—, by allowing the compound to react with a reducing agent such as sodium borohydride in a solvent, for example, chosen from alcoholic solvents such as methanol, ethanol, etc., at a temperature between 0° C. and the temperature at which the reaction mixture will reflux.

If the compound has lower alkoxycarbonyl group as a substituent, it is possible to replace the alkoxycarbonyl group with carboxyl group, by a known method, for example, by hydrolyzing the compound in a solvent chosen from alcoholic solvents such as methanol, ethanol, etc., in the presence of alkaline aqueous solution of lithium hydroxide, sodium hydroxide or the like, at a temperature between room temperature and the temperature at which the reaction mixture will reflux. Further, it is possible to replace the resulting carboxyl group with a carbamoyl group unsubstituted or mono- or di-substituted by lower alkyl groups, by subjecting the compound to the condensing reaction as described in Method C above.

Further, if the compound prepared as above has a halogen atom, or preferably a bromine atom as a substituent on its aromatic ring, it is possible to convert the bromine atom to a cyano group, by a known method, for example, by placing the compound in a solvent not interfering with the reaction, for example, chosen from polar, aprotic solvents such as dimethylformamide, dimethyl sulfoxide, dimethylimidazolidone, etc., by using copper cyanide (I), potassium cyanide, etc., at a temperature between room temperature and the temperature at which the reaction mixture will reflux. This reaction may proceed in the presence of a catalyst chosen from transition metal complexes comprising palladium complexes, for example, palladium acetate, and nickel complexes, for example, tetrakistriphenylphosphine nickel. It is possible to further convert the cyano group to lower alkanoyl group, by allowing the above compound to react with an organic metal compound represented by alkylmagnesium bromide, alkyl lithium, etc., in a solvent not interfering with the reaction, for example, chosen from ether solvents such as diethyl ether, tetrahydrofuran, etc., at a temperature between −100° C. and room temperature.

If the compound prepared as above has, as a substituent, a reactive group such as a hydroxyl group, amino group, carboxyl group, etc., it is possible to protect the group with a protective group appropriately chosen at one process, and then to remove the protective group at another as needed. Introduction and removal of such a protective group may be achieved by any method appropriately chosen depending on the natures of the group to be protected and protective group, for example, by the methods as described in the aforementioned review, "Protective Groups in Organic Synthesis," 3rd Ed., 1999.

Out of the reaction intermediates used in the above processes, it is possible to prepare a compound represented by Formula (XII) by a known method, for example, by allowing a compound represented by Formula (IX) to react with 4-piperidone or its equivalent according to Process 4 of Manufacturing Method 1. Or, it is possible to obtain a compound represented by Formula (XII) wherein Y represents a methylene group, by allowing a compound represented by Formula (XXI):

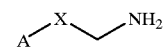

(XXI)

(wherein A and X have the same meanings as defined above) to undergo a reaction by the method as disclosed in Huegi et al., J. Med. Chem., 26:42, 1983.

It is further possible to obtain compounds represented by Formulas (IV) and (V), by allowing compounds represented by Formulas (XII) and (XIII) to react with unprotected or protected acetic acid carrying a desired substituent according to the method as described in Manufacturing Method 2.

Experimental Example

The present invention will be illustrated below with reference to Experimental Examples, but it should be understood that the present invention is not limited in any way to these examples.

Experimental Example 1

Inhibitory Effect on the Binding of Batrachotoxin to Receptors in the Synaptosome from the Rat Brain The experiment was undertaken according to the method disclosed by Catterall et al., J. Biol. Chem. 256(17):8922, 1981. Specifically, to the Hepes/Tris-HCl buffer (pH 7.4) containing a synaptosome membrane fraction prepared from the rat brain, were added the buffer containing 1.5 nM batrachotoxin A20-alfa-benzoate labeled with tritium, 100 μM veratridine and a test compound (concentration is expressed as final one), and the mixture was incubated at 37° C. for 30 minutes. Then, to the mixture was added ice-cooled, cleaning buffer, and the resulting mixture was passed through a GF-C filter (Watman) for filtration. After the filter has been washed three times with cleaning solution, it was assayed with a scintillation counter for the radioactivity of substances attached thereto. The concentration of the test compound necessary for interfering with the specific binding of the radioactive ligand by 50% was determined by the probit method, and it was taken as the $IC_{50}$ value ($\mu$mol/L) of the test compound. The results are shown in Table I. In this experiment, the $IC_{50}$. values of comparative agents were 300 $\mu$mol/L and over for carbamazepine, 17 $\mu$mol/L for mexiletine, and 51 $\mu$mol/L for phenytoin

TABLE 1

Inhibitory effect of test compound on the binding of batrachotoxin with receptors in synaptosome

| Test compound | $IC_{50}$ value ($\mu$mol/L) |
|---|---|
| 50 | 0.30 |
| 51 | 0.61 |
| 55 | 0.28 |

The test compounds of this invention exerted a far higher inhibitory effect on the binding of batrachotoxin than do the conventional medicines used for the treatment of neuropathy pain. From this, it was suggested that the test compounds have a high affinity to the sodium channel.

Experimental Example 2

Inhibitory Effect on the Veratrine-induced Contracture of Isolated Myocardial Cells The experiment was undertaken by the method disclosed by Donck et al., Life Sci., 38:765, 1986. Specifically, the heart removed from the rat according to the Langendorff's method was treated with an enzyme, and isolated myocardial cells were obtained. The myocardial cells were inoculated on a 48 multi-well plate (3548 Coster) previously coated with poly-L-lysine at a rate of $1\times10^4$ cells/well. The plate was kept at 37° C. for 1 hour while being exposed to a flow of gas comprising 95% $O_2$ and 5% $CO_2$, to allow the cells to adhere to the bottom of each well. Then, the test compound was added to each well, and allowed to be there for 30 minutes, and vetratrine was added to each well to 100 $\mu$g/mL. Five minutes later, the cells of each well was checked for their morphological changes, and the changes were photographed. If the cells' shape changed from a rod-like one into a ball-like one in the presence of veratrine, the cells were regarded as falling to contracture as a result of the exposure to veratrine. The inhibitory effect of the test compound on the contracture was determined by the probit method, and was expressed in terms of $IC_{50}$. The results are shown in Table 2.

TABLE 2

Inhibitory effect of test compound on the vetratrine-induced contracture of isolated myocardial cells

| Test compound | $IC_{50}$ value ($\mu$mol/L) |
|---|---|
| 50 | 1.51 |
| 51 | 1.56 |
| 55 | 1.34 |
| 86 | 1.65 |

Veratrine is a mixture of belladonna alkaloids. If veratrine is applied to isolated myocardial cells, the cells which take a rod-like shape in a normal state will fall to contracture, taking a ball-like shape. Veratrine, when applied to isolated myocardial cells, is thought to cause a persistent sodium current in the cells, by suppressing the inactivation of the sodium channel in the cells, which leads to the contracture of the cells (Donck et al., ibid). It was suggested that the compound of this invention will inhibit the persistent sodium current because it was found to inhibit the veratrine-induced contracture of isolated myocardial cells.

Experimental Example 3

Measurement of Intracellular Sodium Concentration

The method disclosed in Experiment Example 2 may be substituted for the method of this experiment. The experiment was undertaken by the method disclosed by Russ et al., Pflugers Archiv. Eur. J. Physiol., 433:26, 1996. For this experiment, myocardial cells or nerve cells isolated from mammals such as rats, guinea pigs, or rabbits, or a cell strain derived from neuroblastoma are usable. In this experiment, a cell strain derived from neuroblastoma was used. Measurement of the intracellular sodium concentration of cultured cells was achieved by determining the intensity of fluorescence emitted by an SBFI dye using a fluorescent microscopic system connected to a photomultiplier, or a video image analysis system. Specifically, the cells were kept in preserving solution containing SBFI acetoxymethy-lester and pluronic acid, so that they were intracellularly loaded with SBFI. After loading, the cells were transferred to a bath on the microscope stage filled with measurement buffer; the cells were exposed to excitation beams having wavelengths of 340 and 380 nm; and fluorescent light having a wavelength between 500 and 530 nm was recorded. The intensities of fluorescence resulting from the two excitation beams were determined, and their ratio was calculated to give the intracellular sodium concentration. Then, veratridine was added to the buffer solution in the bath at a final concentration of 30 $\mu$mol/L, to induce a persistent sodium current in the cells, and the increased intracellular sodium concentration associated therewith was followed. If the test compound of this invention was added to the buffer solution to 0.1 to 100 $\mu$mol/L 10 minutes before the addition of veratridine, it clearly inhibited, in a dose dependent manner, the veratridine-induced increase of the intracellular sodium concentration.

Experimental Example 4

Inhibitory Effect on the Formalin-induced Nociceptive Response in Rats

The experiment was undertaken by the method disclosed by Doak et al., Eur. J. Pharmacol. 281:311, 1995. Specifically, 25 $\mu$L of 0.5% formalin solution was subcutaneously injected into the left foot pad of the rat, and then each behavior of the rat consisting of the licking or biting of the pad immediately following the injection was checked with a stopwatch for its duration, and its cumulative duration was recorded at five minute intervals. The nociceptive response observed in 10 minutes after the injection was termed a first-phase response while the response observed between 10 minutes and 45 minutes after the injection was termed a second-phase response. The test compound was orally applied to the rat 30 minutes before the subcutaneous injected of formalin. Then, the inhibitory effect of the test compound on the nociceptive response induced by the formalin injection was calculated according to the following formula. The resulted thus obtained are shown in Table 3

(n=2-6). To mention, for illustration, the inhibitory effect of carbamazepine, an agent to serve as a comparative example, if it is orally applied at 50 mg/kg, it inhibits the first-phase response by 52%, while it inhibits the second-phase response by 59%.

Percent inhibition (%) -[(PRcontrol-PRtest)/PRcontrol]×100 wherein PRtest is the response time (sec) of the test group which received formalin and the test compound, while PRcontol is the response time of the control group which received formalin alone.

TABLE 3

Inhibitory effect of test compound on the formalin-induced nociceptive response in rats

| Test compound | Dose (mg/kg) | Response inhibition (%) 1st phase | Response inhibition (%) 2nd phase |
|---|---|---|---|
| 50 | 10 | 44 | 64 |
| 51 | 10 | 46 | 67 |
| 55 | 10 | 30 | 55 |
| 56 | 10 | 40 | 70 |
| 58 | 10 | 29 | 56 |
| 60 | 10 | 61 | 92 |
| 65 | 10 | 93 | 96 |
| 84 | 10 | 23 | 49 |
| 86 | 10 | 19 | 62 |
| 90 | 10 | 55 | 65 |
| 96 | 10 | 74 | 69 |

As is obvious from above, the compound of this invention was demonstrated to have an inhibitory effect on the formalin-induced nociceptive response in rats.

Experimental Example 5

Efficacy in the Rat Model Made by Loosely Constring the Sciatic Nerve

Preparation of the rat pain model based on the constriction of the sciatic nerve was performed by the method introduced by Bennett et al. ("Pain," 33:87, 1988). Specifically, the rat was anesthetized with i.p. injection of pentobarbital sodium at 40 mg/kg; the overlying skin was cut open; and the left biceps femoris muscle was bluntly separated. The sciatic nerve was isolated from surrounding tissues; it was gently constricted at four sites about 1 mm apart from each other by the use of surgical gut sutures (4-0); the operated part was closed; and the rat was returned to its cage for further feeding. For the rat belonging to the sham-surgery group, the same operation was performed except that the sciatic nerve was left untouched. Two weeks after the surgery, the response threshold to a mechanical stimulus consisting of touch with a von Frey filament was determined. The test proceeded as follows: the test compound dissolved or suspended in a solvent (0.5% aqueous solution of hydroxypropylmethyl cellulose) was orally applied to the rat having the sciatic nerve constricted; one hour later, von Frey hairs were applied against the foot pad (spots ranging from heel to the mid-point of foot) one after another in an ascending order of their stiffness; if the rat raises its foot when a certain von Frey hair was applied, the stimulus intensity of that hair was taken as the response threshold (maximum stimulus intensity being 28.84g). The results are shown in Table 4 (n=8).

TABLE 4

Efficacy in the rat model made by loosely constring the sciatic nerve

| Operation | Test Compound | Dose (mg/kg) | Mean threshold (g) Test foot (left) | Mean threshold (g) Normal foot (right) |
|---|---|---|---|---|
| Sham-operation | — | — | 16.43 | 16.43 |
| Constriction Press | Solvent | — | 6.77# | 16.43 |
| Constriction Press | Example 51 | 2.5 | 8.33 | 16.43 |
| Constriction Press | Example 51 | 5 | 12.63* | 16.43 |
| Constriction Press | Example 51 | 10 | 15.58** | 16.85 |
| Constriction Press | Carbamazepine | 50 | 8.97 | 19.85 |
| Constriction Press | Carbamazepine | 100 | 19.43** | 27.13 | the difference in the mean between the sham-operation group and the solvent group was found significant at P < 0.05 (T-test).
*the difference in the mean between the solvent group and the test group was found significant at P < 0.05(*) or at P < 0.01(**) (Dunnett's method).

In this test, a marked fall in the threshold to a mechanical stimulus was observed only on the injured side, that is, the side at which the sciatic nerve was constricted, suggesting the presence of allodynia. The compound of this invention significantly increased the threshold of the constricted sciatic nerve to a mechanical stimulus, while it scarcely affected the response threshold of the normal sciatic nerve on the opposite side. In contrast, carbamazepine significantly raised the threshold of the sciatic nerve to a mechanical stimulus not only on the injured side but on the normal side. From above, it was found that the compound of the present invention selectively controls the nociceptive response from the injured nerve.

Experimental Example 6

Effect of Test Compound on the Transient and Persistent Sodium Current (Assayed by the Voltage-clamp Method)

This experiment was undertaken by the method disclosed by Verdonck et al., Eur. J. Pharmacol., 203:371, 1991. Neuroblastoma cells were used. Isolated cells were strewn over a recording chamber filled with perfusion fluid; the membrane currents are recorded in a whole cell configuration by the voltage-clamp method based on the use of a glass microcapillary. Current components due to ions other than sodium ion were eliminated as follows. The potassium current was removed by cesium ion introduced in the capillary, and the calcium current was removed by cobalt ion added to the perfusion fluid. Measurement of the transient sodium current of the cells was achieved by applying depolarizing pulses at appropriate intervals to the cells clamped at holding potential, and by observing a transient inward current elicited therewith. The compound of Example 51 of this invention was added to the perfusion fluid; and its effect on the peak value of the inward current was followed. It was found as a result that the compound decreased the peak by 18% at 53 $\mu$M. Observation of the persistent sodium current was achieved by adding veratridine to the perfusion fluid to 100 $\mu$mol/L, and shifting the holding potential towards depolarization, which caused a persistent inward current to develop in the cells. Then, the test compound of this invention was added to the same perfusion fluid containing veratridine; and its inhibitory effect on the persistent inward current was followed. From results, concentration of the compound of this invention represented in Example 51 to inhibit the persistent sodium current by 18% is calculated at 7.2 $\mu$M. Accordingly, the selective inhibition by the compound of Example 51 against the persistent sodium current in comparison with the transient sodium current, or the ratio of the concentration of the compound of Example 51 necessary for inhibiting the transient sodium current by 18% against the corresponding concentration of the same compound for inhibiting the persistent sodium current by the same amount was 7.4.

Experimental Example 7

Toxicological Study

The compound represented by Example 51 was orally given by gavage to 6 week old Crj:CD(SD) IGS female rats at 5 or 10 mg/kg/day once daily for 14 days. All the rats survived during treatment period, and there was no loss in the weight and no notable abnormalities in general conditions. In histopathologial examining, no abnormal findings were obtained.

From above results it was demonstrated, the compound of the present invention has a high affinity to the sodium channel, and competes, for the binding to sodium channels, with veratrine which has been known as a toxin working on the sodium channel. If orally applied, the compound in question markedly inhibits the formalin-induced nociceptive response in the rat, and, if applied to the rat neuropathic pain model in which the sciatic nerve was constricted, it selectively controls the pain on the injured side. When its effect being observed on isolated cells by the voltage-clamp method, the compound in question selectively inhibits the persistent sodium current. Further, it induces no abnormal response in the toxicological study, suggesting its low toxicity.

Moreover, even if the effective dose of the compound of this invention is administered, and changes in ECG followed, no notable change was observed in the PQ interval nor in the QRS width, which suggests the compound does not have practically any harmful effect on the cardiac function.

Hence, it is expected that the compound of this invention, because of its being highly successful in the animal pain model, and in the animal neuropathic pain model in which the compound did not affect the threshold of nociceptive response in the normal nerve, will give an agent specifically adapted for the treatment of neuropathic pain with few side-effects involving the central nervous system and the digestive tract, in contrast with the corresponding conventional analgesics. Particularly, because of its oral applicability, it gives a high prospect as an agent specifically adapted for the treatment of neuropathic pain.

The known lipid-soluble toxin acting on the sodium channel includes batrachotoxin, veratridine, veratrine (mixture containing veratridine and its analogs), aconitine, etc. These toxins induce the persistent sodium current by supressing the inactivation of the sodium channel in excitable cells such as nerve fibers or cardiac muscle cells. The experiment based on the voltage-clamp method demonstrated that the compound of this invention antagonizes veratrine, by showing it inhibits the persistent sodium current. The compound of this invention, in the experiment on the animal neuropathy model, was found to ameliorate allodynia to a stimulus in the limb affected with neuropathy, but not to affect the response threshold to a stimulus in the normal limb. On the other hand, the known sodium-channel blocker such as carbamazepine or mexiletine which has been widely used for the treatment of pain has a low selectivity against the persistent sodium current in comparison with the transient sodium current, and thus when used at a dose sufficiently concentrated for ameliorating allodynia in the affected limb, it also raises the response threshold in the normal limb. These findings clearly indicate that the compound we found is a selective blocking agent against the persistent sodium current, whereas the conventional sodium channel blocker widely used for the treatment of pain does not so selectively act on the persistent sodium current as does the present compound. The compound of this invention may exert its effect for the treatment of pain, particularly of neuropathic pain, by selectively inhibiting the persistent sodium current, thereby suppressing the over-excitation or abnormal spontaneous excitation of injured nerve cells, because the persistent sodium current is likely to be most deeply involved in the development of abnormal excitability in the membrane of excitable cells.

As discussed above, we found an agent which selectively inhibits the persistent sodium current, and obtained results indicating that the conventional sodium channel blocker does not so selectively inhibit the persistent sodium current as does the present compound. In other words, we found for the first time an agent for selectively inhibiting the persistent sodium current, and confirmed that the agent is effective for treating the pain in the neuropathic pain model, and that the agent does not affect on the normal nerve but on the affected nerve. Because of these features, the compound of this invention will be very advantageous if it is used in the treatment of neuropathic pain. The conventional sodium channel blocker interferes with the normal nerve activity by inhibiting the transient sodium current, which may account for the side-effects involving the central nervous system and the digestive tract, and sometimes the heart. Generally speaking, the compound exerting a selective inhibition against the persistent sodium current is capable of selectively inhibiting the over-excitation or abnormal spontaneous excitation of the injured nerve cell, thereby presenting the prospect of becoming an agent which will be safely used in the treatment of neuropathic pain, being relieved of side-effects.

The selective inhibitor of the persistent sodium current containing the compound of this invention will be effective for the treatment of pain accompanying painful diseases such as hyperalgesia, allodynia, spontaneous painful sensation, for example, for the treatment and prevention of pain accompanying central neuropathy (for example, neuropathy resulting from spinal cord injury), peripheral neuropathy (for example, reflex sympathetic dystrophy (RSD)), herpes zoster during its acute phase, neuralgia subsequent to herpes zoster, diabetic neuropathy, trigeminal neuralgia, post-surgery condition, cancer, low back pain-related neuropathy, inflammatory shoulder joint and its surrounds, state subsequent to spinal cord injury, affected thalamus, affected lower limb, causalgia, reflex sympathetic nerve atrophy, chronic headache, affected tooth, osteoarthritis, arthritis, rheumatism, etc., but its effective use is not limited to the above. Or, the inhibitor may be used for preventing or retarding the aggravation of symptoms accompanying those chronic diseases which otherwise may appear in the course of time.

The selective inhibitor of the persistent sodium current containing the compound of this invention, because of its having a high affinity to the sodium channel and effectively inhibiting the persistent sodium current, will be effective not only for the treatment of neuralgia, headache, etc., but also for the treatment of convulsion, epilepsy, dementia (cerebrovascular and senile dementia), cerebral infarction during its acute phase, cerebral hemorrhage, transient cerebral ischemia, subarachnoidal hemorrhage, head trauma, after-effects subsequent to brain surgery, cerebral vascular disorders subsequent to cerebral arterial sclerosis, atopic dermatitis, itching occurring during hemodialysis to compensate for renal failure, hypersensitive enteral syndrome, urinary incontinence, etc., but its use should not be limited to those diseases.

The medicinal preparation of this invention will be used as a medicinal component.

The medicinal component of this invention may contain at least one of the agents of this invention which selectively inhibit the persistent sodium current, for example, at least one or more of the compounds represented by Formula (I) of this invention, and may be prepared into a medicine in combination with pharmaceutically acceptable additives. Specifically, the preferred additive includes an excipient (for example, lactose, sucrose, mannite, crystalline cellulose, silica), binder (for example, crystalline cellulose, sugars (mannitol, sucrose, sorbitol, erythritol, xylitol), dextrin, hydroxypropylcellulose (HPC), hydroxypropylmethylcellulose (HPMC), polyvinylpyrrolidone (PVP), macrogol), lubricants (for example, magnesium stearate, calcium stearate, carboxymethylcellulose), antiseptic agent (benzarconium chloride, paraoxybenzoate ester), isotonicity (for example, glycerin, sodium chloride, potassium chloride, mannitol, glucose), pH adjuster (sodium hydroxide, potassium hydroxide, sodium carbonate, hydrochloric acid, sulfuric acid, buffer such as phosphate-buffer), stabilizer (for example, sugar, sugar alcohol, xanthan gum), dispersant, anti-oxidant (for example, ascorbic acid, butylhydroxyanisol (BHA), propyl gallate, dl-α-tocophenol), buffering agent, preserver (for example, paraben, benzyl alcohol, benzalconium chloride), flavoring agent (for example, vanillin, 1-mentol, rose oil), solubilizing agent (for example, polyoxyethylene-hydrogenated castor oil, polysorbate 80, polyethyleneglycol, phopholipid cholesterol, triethanolamine), absorption enhancer (for example, sodium glycolate, sodium edetate, sodium caproate, acylcarnitines, limonene), gelatinizer, suspension enhancer, detergent or emulsifier, etc., and these additives and any other appropriate additives and solvents generally used may be combined as appropriate with the compound of this invention, and the mixture may be prepared into any appropriate dosage forms.

The preferred dosage form includes tablets, capsules, granules, powder, pills, suppositories, injectables, sublingual troches, orally applicable liquid, powder or suspension agents, nasally applicable agents, and sustained releasable agents. The agent of this invention may be applied to the patient, in addition to the oral route, subcutaneously, intramuscularly, intravenously, intraarterially, through the tissues surrounding a nerve, extradurally, intrathecally, intraventricularly, intrarectally, nasally, etc. The agent of this invention may be applied as an externally applicable medicine such as ointment, creme, jelly, gel, paint, topically applied drug (tape, patch, pap), external liquid agents, external suspension agents, spray, etc. Further, the agent of this invention may be modified in such a way as to allow the patient, whenever he feels pain, to apply the agent to the affected site through an infuser dedicated for the purpose (patient-treated analgesia), or through a handy type of such infuser.

The agent of this invention should be applied to the adult at 0.1 mg to 1.0 g/day, preferably 0.5 mg to 0.5 g/day, but the dose may be changed as appropriate depending on the severity of the symptom, or on the administration route.

A total dose for a day may be applied at once, or it may be divided into 2 to 6 fractions, and each divided fraction may be applied one after another orally or parenterally, or the dose may be applied dropwise or continuously through a tube inserted into a vein.

EXAMPLES

Next, this invention will be described below more in detail by means of Examples, but it should be understood that this invention is not limited in any way to those examples.

The nuclear magnetic resonance (NMR) spectrum of the test compound was obtained with machines provided by JEOL Ltd.(JEOL JNM-EX270 FT-NMR (data obtained with this machine were marked with *) or JEOL JNM-LA300 FT-NMR). The infra-red absorption spectrum of the test compound was obtained with machines provided by Horiba Seisakusho (FT-200 or FT-720). The melting point of the test compound was measured with instruments provided by Mettler (FP80 or FP90).

Example 1

Synthesis of 4-[2-[N-methyl-N-(4-isopropoxyphenyl)-amino]ethyl]-1-(2-phenylethyl)piperidin-4-ol
<Step 1> Synthesis of 4'-isopropoxyacetanilide To a solution of 4-isopropoxyaniline (151.6 g) and triethylamine (153.7 mL) in methylene chloride (1 L) was dropwise added, a solution of acetyl chloride (78.4 mL) in methylene chloride (200 mL) under ice-water cooling so that the internal temperature was kept at 10–15° C. The reaction mixture was stirred for 30 minutes while being cooled with ice-water, and then at room temperature for 60 minutes. The reaction mixture was poured into water, and then extracted with methylene chloride. The organic layer was washed with 1N hydrochloric acid and water in this order, and dried with anhydrous sodium sulfate, and the solvent was evaporated under a reduced pressure. Ether was added to the residue for crystallization to give the designated compound (191.5 g).
<Step 2> Synthesis of N-methyl-4'-isopropoxyacetanilide Potassium hydroxide (71.7 g) was suspended in dimethyl sulfoxide (160 mL), to which was added a solution in dimethyl sulfoxide (320 mL) of the compound (161.5 g) obtained through Step 1, and the mixture was stirred at room temperature for 20 minutes, and then at 50° C. for 30 minutes under nitrogen atmosphere. To the mixture was dropwise added under ice-water cooling methyl iodide (62.2 mL), and the mixture was stirred at the same temperature for 10 minutes, at room temperature for 3 hours and at 35–40° C. for 1.5 hours. This reaction mixture was poured into ice-water, and extracted with ethyl acetate. The organic layer was washed with water and saturated aqueous solution of salt in this order, and was dried with anhydrous sodium sulfate. The solvent was evaporated under a reduced pressure, to give the designated compound (166.1 g).
<Step 3> Synthesis of N-methyl-N-(4-isopropoxyphenyl)-2-(1-benzyl-4-hydroxypiperidin-4-yl)acetamide To a solution in anhydrous tetrahydrofuran (300 mL) of lithium diisopropylamide which had been prepared from diisopropylamine (44.3 mL) and n-butyllithium (1.6M solution in hexane, 196 mL), was added a solution in anhydrous tetrahydrofuran (100 mL) of the compound (62.0 g) obtained through Step 2 at −25 to −20° C., and the mixture was stirred at −25° C. for 30 minutes. Then, to the mixture was added a solution of 1-benzylpiperidin-4-one (56.6 g) in anhydrous tetrahydrofuran (100 mL) at −25 to −20° C., and the reaction mixture was stirred at −25° C. for 10 minutes. The reaction vessel was slowly warmed to room temperature, and the reaction mixture was poured into saturated aqueous solution of salt, and extracted with ethyl acetate. The organic layer was washed with saturated aqueous solution of salt, and dried with anhydrous sodium sulfate, and the solvent was evaporated under a reduced pressure. To the residue thus obtained was added ether for crystallization, to give the designated compound (83.8 g).

<Step 4> Synthesis of 1-benzyl-4-[2-[N-methyl-N-(4-isopropoxyphenyl)amino]ethyl]piperidin-4-ol A solution in anhydrous tetrahydrofuran (300 mL) of the compound (76.6 g) obtained through Step 3 was cooled with ice-water under nitrogen atmosphere, to which was added little by little a solution of borane-tetrahydrofuran complex in tetrahydrofuran (1M, 800 mL), and the reaction mixture was stirred at the same temperature for 30 minutes and then at room temperature for 3 hours. To the mixture while being ice-water cooled, was added methanol (120 mL) little by little, which was followed by the addition of 10% hydrogen chloride-methanol solution (160 mL) to adjust the pH to 1 or less. Then, the mixture was heated under reflux for 2 hours. After cooling, the solvent was evaporated under a reduced pressure, and ether was added to the residue for crystallization. The crystals thus obtained were dissolved in 1N hydrochloric acid, and washed with ether. To the aqueous layer was added potassium carbonate to adjust the pH to 9 or more, and extraction was performed by the addition of ethyl acetate. The organic layer was washed with saturated aqueous solution of salt, and dried with anhydrous sodium sulfate, and the solvent was evaporated under a reduced pressure, to give the designated compound (71.3 g).

<Step 5> Synthesis of 4-[2-[N-methyl-N-(4-isopropoxyphenyl)amino]ethyl]piperidin-4-ol To a solution in methanol (335 mL) of the compound (67.0 g) obtained through Step 4 were added formic acid (39.6 mL) and 10% palladium on carbon (3.35 g), and the mixture was heated under reflux under nitrogen atmosphere for 3 hours. Then, formic acid (19.8 mL) and 10% palladium on carbon (3.35 g) were added anew, and the mixture was heated under reflux for further 2 hours. The catalyst was filtered off by the passage through celite, and to the filtrate were added formic acid (19.8 mL) and 10% palladium on carbon (3.35 g), and the mixture was heated under reflux for 2 hours. After cooling, the catalyst was removed by filtration, and to the filtrate was added under ice-water cooling 5N aqueous solution of sodium hydroxide (315 mL) which was followed by the addition of saturated aqueous solution of sodium hydrogen carbonate to adjust the pH to 9 or more. The mixture was condensed to dryness under a reduced pressure. To the residue was added methylene chloride, and the mixture was stirred overnight. To the mixture was added anhydrous sodium sulfate, and the mixture was stirred, and then removed of insoluble salt by filtration, and the filtrate was condensed to dryness under a reduced pressure. The residue thus obtained was submitted to silica gel column chromatography (Chromatorex NH™) (eluent; hexane ethyl acetate=1:2 to ethyl acetate:methanol= 8:2) for purification, to give the designated compound (33.4 g).

<Step 6> Synthesis of 4-[2-[N-methyl-N-(4-isopropoxyphenyl)-amino]ethyl]-1- (2-phenylethyl)piperidin-4-ol To a solution in anhydrous methylene chloride (130 mL) of the compound (3.7 g) obtained through Step 5 were added under ice-water cooling a solution of 50% phenylacetaldehyde in 2-propanol (6.1 g), acetic acid (2.6 mL) and sodium triacetoxyborohydride (10.7 g), and the mixture was stirred under argon atmosphere for 1 hour. After being stirred at room temperature for further 2 hours, the reaction mixture received the addition of saturated aqueous solution of sodium hydrogen carbonate until it became basic, and extraction was performed through the addition of methylene chloride. The organic layer was washed with water, and extracted with dil. hydrochloric acid. Then, the aqueous layer was washed with ethyl acetate, and received the addition of 1N aqueous solution of sodium hydroxide until it became basic, and extraction was performed through the addition of ethyl acetate. The organic layer was washed with saturated aqueous solution of salt, and dried with anhydrous sodium sulfate, and the solvent was evaporated under a reduced pressure. The residue thus obtained was submitted to silica gel column chromatography (Chromatorex NH™) (eluent; ethyl acetate: hexane=1:4) for purification, to give the designated compound (4.5 g).

The following compounds were synthesized as in Step 6 of Example 1, using the compound obtained through Step 5 of Example Example 2

1-[2-(4-cyanophenyl)ethyl]-4-[2-[N-methyl-N-(4-isopropoxyphenyl)amino]ethyl]piperidin-4-ol Example 3

1-[2-[4-(methoxycarbonyl)phenyl]ethyl]-4-[2-[N-methyl-N-(4-isopropoxyphenyl)amino]ethyl]piperidin-4-ol Example 4

1-[2-[4-(ethoxycarbonyl)phenyl]ethyl]-4-[2-[N-methyl-N-(4-isopropoxyphenyl)amino]ethyl]piperidin-4-ol Example 5

4-[2-[N-methyl-N-(4-isopropoxyphenyl)amino]ethyl]-1-[2-(4-methylsulfinylphenyl)ethyl]piperidin-4-ol Example 6

Synthesis of 1-[2-(4-fluorophenyl)ethyl]-4-[2-[N-methyl-N-(4-isopropoxyphenyl)amino]ethyl]piperidin-4-ol To a solution in anhydrous dimethylformamide (5 mL) of the compound obtained through Step 5 of Example 1 (0.29 g) were added 4-fluorophenethyl chloride (0.24 g), potassium carbonate (0.21 g) and sodium iodide (0.04 g), and the mixture was stirred at 70 to 80° C. for 2 hours. The reaction mixture was poured into ice-water, to which was added a saturated aqueous solution of sodium hydrogen carbonate, and the mixture was extracted with ethyl acetate. The organic layer was washed with water and saturated aqueous solution of salt, and dried with anhydrous sodium sulfate, and the solvent was evaporated under a reduced pressure. The residue thus obtained was submitted to silica gel column chromatography (Chromatorex NH™) (eluent; ethyl acetate hexane=1:4 to 1:3) for purification, to give the designated compound (0.27 g)

The following compounds were synthesized by the same steps as in Example 6.

Example 7

4-[2-[N-methyl-N-(4-isopropoxyphenyl)amino]ethyl]-1-[2-(4-nitrophenyl)ethyl]piperidin-4-ol

Example 8

1-[2-(3-cyanophenyl)ethyl]-4-[2-[N-methyl-N-(4-isopropoxyphenyl)amino]ethyl]piperidin-4-ol

Example 9

Synthesis of 1-[2-(3-fluorophenyl)ethyl]-4-[2-[N-methyl-N-(4-isopropoxyphenyl)amino]ethyl]piperidin-4-ol
<Step 1>
Synthesis of 1-(3-fluorophenyl)acetyl-4-[2-[N-methyl-N-(4-isopropoxyphenyl)amino]ethyl]piperidin-4-ol To a solution in anhydrous methylene chloride (5 mL) of the compound (0.50 g) obtained through Step 5 of Example 1 and 3-fluorophenylacetic acid (0.29 g) was added 1-ethyl-3-(3-dimethylaminopropyl)carbodiimide hydrochloride (0.36 g), and the mixture was stirred at room temperature overnight. The reaction mixture received the addition of water and was extracted with methylene chloride. The organic layer was washed with saturated aqueous solution of sodium hydrogen carbonate, and dried with anhydrous sodium sulfate, and the solvent was evaporated under a reduced pressure. The residue thus obtained was submitted to silica gel column chromatography (Chromatorex NH™) (eluent; ethyl acetate: hexane=1:4 to ethyl acetate) for purification, to give the designated compound (0.52 g).
<Step 2> Synthesis of 1-[2-(3-fluorophenyl)ethyl]-4-[2-[N-methyl-N-(4-isopropoxyphenyl)amino]ethyl]piperidin-4-ol To a solution in anhydrous tetrahydrofuran (9 mL) of the compound (0.51 g) obtained through Step 1 was added borane-methyl sulfide complex (10M, 0.7 mL), and the mixture was heated under reflux for 2 hours. Then, methanol (3 mL) and 10% hydrogen chloride-methanol solution (5 mL) was added, and the mixture was heated under reflux for 3 hours. After cooling, the solvent was evaporated under a reduced pressure, to which was added saturated aqueous solution of sodium hydrogen carbonate to make basic, and the mixture was extracted with ethyl acetate. The organic layer was washed with saturated aqueous solution of salt, and dried with anhydrous sodium sulfate, and the solvent was evaporated under a reduced pressure. The residue thus obtained was submitted to silica gel column chromatography (Chromatorex NH™) (eluent; ethyl acetate:hexane=1:3 to ethyl acetate) for purification, to give the designated compound (0.44 g).

The following compounds were synthesized by the same steps as in Step 1 and Step 2 of Example 9 above.

Example 10

1-[2-(2-fluorophenyl)ethyl]-4-[2-[N-methyl-N-(4-isopropoxyphenyl)amino]ethyl]piperidin-4-ol
<Step 1> 1-(2-fluorophenyl)acetyl-4-[2-[N-methyl-N-(4-isopropoxyphenyl)amino]ethyl]piperidin-4-ol
<Step 2> 1-[2-(2-fluorophenyl)ethyl]-4-[2-[N-methyl-N-(4-isopropoxyphenyl)amino]ethyl]piperidin-4-ol

Example 11

1-[2-(4-chlorophenyl)ethyl]-4-[2-[N-methyl-N-(4-isopropoxyphenyl)amino]ethyl]piperidin-4-ol
<Step 1> 1-(4-chlorophenyl)acetyl-4-[2-[N-methyl-N-(4-isopropoxyphenyl)amino]ethyl]piperidin-4-ol
<Step 2> 1-[2-(4-chlorophenyl)ethyl]-4-[2-[N-methyl-N-(4-isopropoxyphenyl)amino]ethyl]piperidin-4-ol

Example 12

1-[2-(3-chlorophenyl)ethyl]-4-[2-[N-methyl-N-(4-isopropoxyphenyl)amino]ethyl]piperidin-4-ol
<Step 1> 1-(3-chlorophenyl)acetyl-4-[2-[N-methyl-N-(4-isopropoxyphenyl)amino]ethyl]piperidin-4-ol
<Step 2> 1-[2-(3-chlorophenyl)ethyl]-4-[2-[N-methyl-N-(4-isopropoxyphenyl)amino]ethyl]piperidin-4-ol

Example 13

1-[2-(2-chlorophenyl)ethyl]-4-[2-[N-methyl-N-(4-isopropoxyphenyl)amino]ethyl]piperidin-4-ol
<Step 1> 1-(2-chlorophenyl)acetyl-4-[2-[N-methyl-N-(4-isopropoxyphenyl)amino]ethyl]piperidin-4-ol
<Step 2> 1-[2-(2-chlorophenyl)ethyl]-4-[2-[N-methyl-N-(4-isopropoxyphenyl)amino]ethyl]piperidin-4-ol

Example 14

4-[2-[N-methyl-N-(4-isopropoxyphenyl)amino]ethyl]-1-[2-[4-(trifluoromethyl)phenyl]ethyl]piperidin-4-ol
<Step 1> 4-[2-[N-methyl-N-(4-isopropoxyphenyl)amino]ethyl]-1-[[4-(trifluoromethyl)phenyl]acetyl]piperidin-4-ol
<Step 2> 4-[2-[N-methyl-N-(4-isopropoxyphenyl)amino]ethyl]-1-[2-[4-(trifluoromethyl)phenyl]ethyl]piperidin-4-ol

Example 15

4-[2-[N-methyl-N-(4-isopropoxyphenyl)amino]ethyl]-1-[2-[3-(trifluoromethyl)phenyl]ethyl]piperidin-4-ol
<Step 1> 4-[2-[N-methyl-N-(4-isopropoxyphenyl)amino]ethyl]-1-[[3-(trifluoromethyl)phenyl]acetyl]piperidin-4-ol
<Step 2> 4-[2-[N-methyl-N-(4-isopropoxyphenyl)amino]ethyl]-1-[2-[3-(trifluoromethyl)phenyl]ethyl]piperidin-4-ol

Example 16

4-[2-[N-methyl-N-(4-isopropoxyphenyl)amino]ethyl]-1-[2-[2-(trifluoromethyl)phenyl]ethyl]piperidin-4-ol
<Step 1> 4-[2-[N-methyl-N-(4-isopropoxyphenyl)amino]ethyl]-1-[[2-(trifluoromethyl)phenyl]acetyl]piperidin-4-ol
<Step 2> 4-[2-[N-methyl-N-(4-isopropoxyphenyl)amino]ethyl]-1-[2-[2-(trifluoromethyl)phenyl]ethyl]piperidin-4-ol

Example 17

4-[2-[N-methyl-N-(4-isopropoxyphenyl)amino]ethyl]-1-[2-(3-nitrophenyl)ethyl]piperidin-4-ol
<Step 1> 4-[2-[N-methyl-N-(4-isopropoxyphenyl)amino]ethyl]-1-[(3-nitrophenyl)acetyl]piperidin-4-ol
<Step 2> 4-[2-[N-methyl-N-(4-isopropoxyphenyl)amino]ethyl]-1-[2-(3-nitrophenyl)ethyl]piperidin-4-ol

Example 18

4-[2-[N-methyl-N-(4-isopropoxyphenyl)amino]ethyl]-1-[2-(2-nitrophenyl)ethyl]piperidin-4-ol
<Step 1> 4-[2-[N-methyl-N-(4-isopropoxyphenyl)amino]ethyl]-1-[(2-nitrophenyl)acetyl]piperidin-4-ol
<Step 2> 4-[2-[N-methyl-N-(4-isopropoxyphenyl)amino]ethyl]-1-[2-(2-nitrophenyl)ethyl]piperidin-4-ol

Example 19

4-[2-[N-methyl-N-(4-isopropoxyphenyl)amino]ethyl]-1-[2-(4-methylphenyl)ethyl]piperidin-4-ol
<Step 1> 4-[2-[N-methyl-N-(4-isopropoxyphenyl)amino]ethyl]-1-[(4-methylphenyl)acetyl]piperidin-4-ol
<Step 2> 4-[2-[N-methyl-N-(4-isopropoxyphenyl)amino]ethyl]-1-[2-(4-methylphenyl)ethyl]piperidin-4-ol

Example 20

4-[2-[N-methyl-N-(4-isopropoxyphenyl)amino]ethyl]-1-[2-[3-(methylphenyl)ethyl]piperidin-4-ol
<Step 1> 4-[2-[N-methyl-N-(4-isopropoxyphenyl)amino]ethyl]-1-[(3-methylphenyl)acetyl]piperidin-4-ol
<Step 2> 4-[2-[N-methyl-N-(4-isopropoxyphenyl)amino]ethyl]-1-[2-(3-methylphenyl)ethyl]piperidin-4-ol

Example 21

4-[2-[N-methyl-N-(4-isopropoxyphenyl)amino]ethyl]-1-[2-(2-methylphenyl)ethyl]piperidin-4-ol
<Step 1> 4-[2-[N-methyl-N-(4-isopropoxyphenyl)amino]ethyl]-1-[(2-methylphenyl)acetyl]piperidin-4-ol
<Step 2> 4-[2-[N-methyl-N-(4-isopropoxyphenyl)amino]ethyl]-1-[2-(2-methylphenyl)ethyl]piperidin-4-ol

Example 22

1-[2-(4-bromophenyl)ethyl]-4-[2-[N-methyl-N-(4-isopropoxyphenyl)amino]ethyl]piperidin-4-ol
<Step 1> 1-(4-bromophenyl)acetyl-4-[2-[N-methyl-N-(4-isopropoxyphenyl)amino]ethyl]piperidin-4-ol
<Step 2> 1-(2-(4-bromophenyl)ethyl]-4-[2-[N-methyl-N-(4-isopropoxyphenyl)amino]ethyl]piperidin-4-ol

Example 23

1-[2-(3-bromophenyl)ethyl]-4-[2-[N-methyl-N-(4-isopropoxyphenyl)amino]ethyl]piperidin-4-ol
<Step 1> 1-(3-bromophenyl)acetyl-4-[2-[N-methyl-N-(4-isopropoxyphenyl)amino]ethyl]piperidin-4-ol
<Step 2> 1-[2-(3-bromophenyl)ethyl]-4-[2-[N-methyl-N-(4-isopropoxyphenyl)amino]ethyl]piperidin-4-ol

Example 24

1-[2-(2-bromophenyl)ethyl]-4-[2-[N-methyl-N-(4-isopropoxyphenyl)amino]ethyl]piperidin-4-ol
<Step 1> 1-(2-bromophenyl)acetyl-4-[2-[N-methyl-N-(4-isopropoxyphenyl)amino]ethyl]piperidin-4-ol
<Step 2> 1-[2-(2-bromophenyl)ethyl]-4-[2-[N-methyl-N-(4-isopropoxyphenyl)amino]ethyl]piperidin-4-ol

Example 25

4-[2-[N-methyl-N-(4-isopropoxyphenyl)amino]ethyl]-1-[2-(4-trifluoromethoxyphenyl)ethyl]piperidin-4-ol
<Step 1> 4-[2-[N-methyl-N-(4-isopropoxyphenyl)amino]ethyl]-1-[(4-trifluoromethoxyphenyl)acetyl]piperidin-4-ol
<Step 2> 4-[2-[N-methyl-N-(4-isopropoxyphenyl)amino]ethyl]-1-[2-(4-trifluoromethoxyphenyl)ethyl]piperidin-4-ol

Example 26

4-[2-[N-methyl-N-(4-isopropoxyphenyl)amino]ethyl]-1-[2-[4-(methylthio)phenyl]ethyl]piperidin-4-ol
<Step 1> 4-[2-[N-methyl-N-(4-isopropoxyphenyl)amino]ethyl]-1-[[4-(methylthio)phenyl]acetyl]piperidin-4-ol
<Step 2> 4-[2-[N-methyl-N-(4-isopropoxyphenyl)amino]ethyl]-1-[2-[4-(methylthio)phenyl]ethyl]piperidin-4-ol

Example 27

4-[2-[N-methyl-N-(4-isopropoxyphenyl)amino]ethyl]-1-[2-(4-methylsulfonylphenyl)ethyl]piperidin-4-ol
<Step 1> 4-[2-[N-methyl-N-(4-isopropoxyphenyl)amino]ethyl]-1-[(4-methylsulfonylphenyl)acetyl]piperidin-4-ol
<Step 2> 4-[2-[N-methyl-N-(4-isopropoxyphenyl)amino]ethyl]-1-[2-(4-methylsulfonylphenyl)ethyl]piperidin-4-ol

Example 28

4-[2-[N-methyl-N-(4-isopropoxyphenyl)amino]ethyl]-1-[2-(4-sulfamoylphenyl)ethyl]piperidin-4-ol
<Step 1> 4-[2-[N-methyl-N-(4-isopropoxyphenyl)amino]ethyl]-1-[(4-sulfamoylphenyl)acetyl]piperidin-4-ol
<Step 2> 4-[2-[N-methyl-N-(4-isopropoxyphenyl)amino]ethyl]-1-[2-(4-sulfamoylphenyl)ethyl]piperidin-4-ol

Example 29

Synthesis of 1-[2-(4-cyanophenyl)ethyl]-4-[2-[N-methyl-N-4-isopropoxyphenyl)amino]ethyl]piperidin-4-ol To a solution in anhydrous dimethylformamide (50 mL) of the compound (9.8 g) obtained through Step 2 of Example 22 was added copper cyanide (I) (2.46 g), and the mixture was heated under reflux for 9 hours under nitrogen atmosphere. The reaction mixture was cooled to room temperature, to which was added 28% aqueous solution of ammonia (300 mL), and the mixture was extracted with ethyl acetate. The organic layer was stirred at room temperature for 30 minutes and then washed with 28% aqueous solution of ammonia, water and saturated aqueous solution of salt in this order, and dried with anhydrous sodium sulfate, and the solvent was evaporated under a reduced pressure. The residue thus obtained was submitted to silica gel column chromatography (Chromatorex NH™) (eluent; ethyl acetate:hexane=1:3 to 1:2) for purification, to give the designated compound (4.2 g).

The following compounds were synthesized as in Example 29.

Example 30

1-[2-(2-cyanophenyl)ethyl]-4-[2-[N-methyl-N-(4-isopropoxyphenyl)amino]ethyl]piperidin-4-ol

Example 31

Synthesis of 1-[2-(4-carboxyphenyl)ethyl]-4-[2-[N-methyl-N-(4-isopropoxyphenyl)amino]ethyl]piperidin-4-ol To a solution in methanol (20 mL) of the compound (1.5 g) obtained through Example 3 was added an aqueous solution (3 mL) of sodium hydroxide (0.26 g), and the mixture was heated under reflux for 1 hour. The reaction mixture was cooled to room temperature, and condensed to dryness. The residue thus obtained was dissolved in water (10 mL). The solution had its pH adjusted to pH5 with conc. hydrochloric acid, and was extracted with methylene chloride. The organic layer was washed with saturated aqueous solution of salt, dried with anhydrous sodium sulfate, and had its solvent eliminated through evaporation under a reduced pressure to give the designated compound (1.45 g).

Example 32

Synthesis of 1-[2-(4-carbamoylphenyl)ethyl]-4-[2-[N-methy]-N-(4-isopropoxyphenyl)amino]ethyl]piperidin-4-ol The compound (0.77 g) obtained in Example 31 and 1-hydroxybenzotriazole (0.28 g) were dissolved in dimethylformamide (5.4 mL), to which was added under ice-water cooling 1-ethyl-3-(3-dimethylaminopropyl)carbodiimide hydrochloride (0.5 g), and the mixture was stirred for 2 hours at room temperature. Then, to the mixture was added under ice-water cooling 28% aqueous solution of ammonia (1.06 g), and the mixture was stirred for 1.5 hours at room temperature. The mixture received the addition of saturated aqueous solution of sodium hydrogencarbonate while being cooled with ice-water, and extracted with ethyl acetate. The organic layer was washed with water and saturated aqueous solution of salt, dried with anhydrous sodium sulfate, and had its solvent eliminated through evaporation under a reduced pressure. The residue thus obtained received the addition of ether for crystallization, to give the designated compound (0.45 g).

The following compound was synthesized as in Example 32.

Example 33

1-[2-(4-dimethylcarbamoylphenyl)ethyl]-4-[2-[N-methyl-N-(4-isopropoxyphenyl)amino]ethyl]piperidin-4-ol Example 34

Synthesis of 1-[2-(4-acetylphenyl)ethyl]-4-[2-[N-methyl-N-(4-isopropoxyphenyl)amino]ethyl]piperidin-4-ol To a solution in ether (1M, 10.7 mL) of methyl lithium was added dropwise under ice-water cooling a solution in anhydrous tetrahydrofuran (9 mL) of the compound (0.9 g) obtained in Example 2, and the mixture was stirred for 55 minutes under ice-water cooling. Then, the reaction mixture received the addition of sulfuric acid (3M, 4.3 mL) while being cooled with ice water, and was stirred at room temperature for 20 minutes. The reaction mixture was made alkaline through the addition of saturated aqueous solution of sodium hydrogencarbonate, and extracted with ethyl acetate. The organic layer was washed with saturated aqueous solution of salt, and dried with anhydrous sodium sulfate, and the solvent was evaporated under a reduced pressure. The residue thus obtained was submitted to silica gel column chromatography (eluent; methylene chloride:methanol=95:5) for purification, to give the designated compound (0.6 g).

Example 35

Synthesis of 1-[2-(4-fluorophenyl)-2-hydroxyethyl]-4-[2-[N-methyl-N-(4-isopropoxyphenyl)amino]ethyl]piperidin-4-ol
<Step 1> Synthesis of 1-(4-fluorobenzoylmethyl)-4-[2-[N-methyl-N-(4-isopropoxyphenyl)amino]ethyl]piperidin-4-ol The compound (0.8 g) obtained through Step 5 of Example 1 and 2-bromo-4'-fluoroacetophenone (0.64 g) were dissolved in anhydrous tetrahydrofuran (10 mL), to which was added triethylamine (0.29 g) while being cooled with ice water, and the mixture was stirred for 1 hour. The mixture was then stirred at room temperature for 5 hours. Then, the mixture received the addition of saturated aqueous solution of sodium hydrogencarbonate, and was extracted with ethyl acetate. The organic layer was washed with saturated aqueous solution of salt, dried with anhydrous sodium sulfate, and had its solvent eliminated through evaporation under a reduced pressure. The residue thus obtained was submitted to silica gel column chromatography (Chromatorex NH™) (eluent; ethyl acetate:hexane=1:2 to 1:1) for purification, to give the designated compound (0.26 g).
<Step 2> Synthesis of 1-[2-(4-fluorophenyl)-2-hydroxyethyl]-4-[2-[N-methyl-N-(4-isopropoxyphenyl)amino]ethyl]-piperidin-4-ol To a solution in methanol (2 mL) of the compound (0.24 g) obtained through Step 1 above was added under ice-water cooling sodium borohydride (21 mg), and the mixture was stirred for 3 hours. Then, the mixture received the addition of water, and was extracted with ethyl acetate. The organic layer was washed with saturated aqueous solution of salt, dried with anhydrous sodium sulfate, and had its solvent eliminated through evaporation under a reduced pressure. The residue thus obtained was submitted to silica gel column chromatography (eluent; ethyl acetate:hexane=1:2 to 2:3) for purification, to give the designated compound (0.16 g).

The following compounds were synthesized by processing the compound obtained through Step 5 of Example 1 as in Step 6 of Example 1.

Example 36

1-[2-(3-furyl)ethyl]-4-[2-[N-methyl-N-(4-isopropoxyphenyl)amino]ethyl]piperidin-4-ol Example 37

Synthesis of 1-[2-(2-furyl)ethyl]-4-[2-[N-methyl-N-(4-isopropoxyphenyl)amino]ethyl]piperidin-4-ol
<Step 1> Synthesis of 1-(2-furyl)acetyl-4-[2-[N-methyl-N-(4-isopropoxyphenyl)amino]ethyl]piperidin-4-ol Processing the compound (1.35 g) obtained through Step 5 of Example 1 and 2-furylacetic acid (0.64 g) as in Step 1 of Example 9 gave the designated compound (1.06 g).
<Step 2> Synthesis of 1-[2-(2-furyl)ethyl]-4-[2-[N-methyl-N-(4-isopropoxyphenyl)amino]ethyl]piperidin-4-ol Processing the compound (0.98 g) obtained through Step 1, as in Step 4 of Example 1 gave the designated compound (0.43 g).

Synthesis of the following compounds was achieved by employing processes similar to Steps 1 and 2 of Example 37.

Example 38

4-[2-[N-methyl-N-(4-isopropoxyphenyl)amino]ethyl]-1-[2-(2-thienyl)ethyl]piperidin-4-ol
<Step 1> 4-[2-[N-methyl-N-(4-isopropoxyphenyl)amino]ethyl]-1-[(2-thienyl)acetyl]piperidin-4-ol
<Step 2> 4-[2-[N-methyl-N-(4-isopropoxyphenyl)amino]ethyl]-1-[2-(2-thienyl)ethyl]piperidin-4-ol Example 39

4-[2-[N-methyl-N-(4-isopropoxyphenyl)amino]ethyl]-1-[2-(3-thienyl)ethyl]piperidin-4-ol
<Step 1> 4-[2-[N-methyl-N-(4-isopropoxyphenyl)amino]ethyl]-1-[(3-thienyl)acetyl]piperidin-4-ol
<Step 2> 4-[2-[N-methyl-N-(4-isopropoxyphenyl)amino]ethyl]-1-[2-(3-thienyl)ethyl]piperidin-4-ol Example 40

1-[2-(4-methoxyphenyl)ethyl]-4-[2-[N-methyl-N-(4-isopropoxyphenyl)amino]ethyl]piperidin-4-ol
<Step 1> 1-(4-methoxyphenyl)acetyl-4-[2-[N-methyl-N-(4-isopropoxyphenyl)amino]ethyl]piperidin-4-ol
<Step 2> 1-[2-(4-methoxyphenyl)ethyl]-4-[2-[N-methyl-N-(4-isopropoxyphenyl)amino]ethyl]piperidin-4-ol Example 41

1-[2-[4-(dimethylamino)phenyl]ethyl]-4-[2-[N-methyl-N-(4-isopropoxyphenyl)amino]ethyl]piperidin-4-ol
<Step 1> 1-[4-(dimethylamino)phenyl]acetyl-4-[2-[N-methyl-N-(4-isopropoxyphenyl)amino]ethyl]piperidin-4-ol
<Step 2> 1-[$^2$-[4-(dimethylamino)phenyl]ethyl]-4-[2-[N-methyl-N-(4-isopropoxyphenyl)amino]ethyl]piperidin-4-ol Example 42

Synthesis of 1-[2-(4-cyanophenyl)ethyl]-4-[2-[N-(4-ethoxyphenyl)-N-methylamino]ethyl]piperidin-4-ol
<Step 1> Synthesis of N-(4-ethoxyphenyl)-N-methyl-2-(1-benzyl-4-hydroxypiperidin-4-yl)acetamide A solution in anhydrous tetrahydrofuran (30 mL) of 4'-ethoxy-N-methylacetanilide (0.97 g) which had been obtained by the method similar to Steps 1 and 2 of Example 1, was cooled to −78° C. under argon atmosphere, to which was added lithium hexamethyldisilazide (1M solution in tetrahydrofuran, 6 mL) at −65° C. or less, and the mixture was stirred at −78° C. for 15 minutes. Next, the mixture received the addition of 1-benzylpiperidin-4-one (1.1 g) at −650° C. or less, and was stirred at −78° C. for 10 minutes. The mixture was warmed to room temperature, to which was added water, and the mixture was extracted with ethyl acetate. The organic layer was washed with water and saturated aqueous solution of salt, dried with anhydrous sodium sulfate, and had its solvent eliminated through evaporation under a reduced pressure. The residue thus obtained was recrystallized from hexane to give the designated compound (1.08 g).

<Step 2> Synthesis of 1-benzyl-4-[2-[N-(4-ethoxyphenyl)-N-methylamino]ethyl]piperidin-4-ol Processing the compound (6.0 g) obtained through Step 1 above, as in Step 4 of Example 1 gave the designated compound (5.58 g).

<Step 3> Synthesis of 4-[2-[N-(4-ethoxyphenyl)-N-methylamino]ethyl]piperidin-4-ol To a solution in methanol (270 mL) of the compound (5.48 g) obtained by Step 2 above was added 10% palladium on carbon (0.55 g), and the mixture was stirred at room temperature all day under hydrogen atmosphere. The catalyst was filtered off and the filtrate was condensed to dryness under a reduced pressure to give the designated compound (4.10 g).

<Step 4> Synthesis of 1-[2-(4-cyanophenyl)ethyl]-4-[2-[N-(4-ethoxyphenyl)-N-methylamino]ethyl]piperidin-4-ol Processing the compound (0.50 g) obtained through Step 3 above and 4-cyanophenylacetaldehyde (0.52 g), as in Step 6 of Example 1 gave the designated compound (0.54 g).

Example 43

Synthesis of 1-[2-(4-cyanophenyl)ethyl]-4-[2-[N-methyl-N-(3-isopropoxyphenyl)amino]ethyl]piperidin-4-ol <Step 1> N-methyl-N-(3-isopropoxyphenyl)-2-(1-benzyl-4-hydroxypiperidin-4-yl)acetamide To a solution in anhydrous tetrahydrofuran (25 mL) of lithium diisopropylamide which had been prepared from diisopropylamine (2.96 g) and n-butyllithium (1.6M solution in hexane, 18.3 mL), was added another solution in anhydrous tetrahydrofuran (15 mL) of 3'-isopropoxy-N-methylacetanilide (5.50 g) which had been obtained by the method similar to Steps 1 and 2 of Example 1, at −55° C. or less, and the mixture was stirred at −78° C. for 25 minutes. At this moment, to the mixture was added a solution in anhydrous tetrahydrofuran (15 mL) of 1-benzylpiperidin-4-one (5.29 g) at −60° C. or less, and the mixture was stirred at −78° C. for 35 minutes. The mixture was warmed to room temperature, to which was added water, and was extracted with ethyl acetate. The organic layer was washed with water and saturated aqueous solution of salt, dried with anhydrous sodium sulfate, and had its solvent removed through evaporation under reduced pressure. The residue was recrystallized from ether-hexane to give the designated compound (7.39 g).

<Step 2> Synthesis of 1-benzyl-4-[2-[N-methyl-N-(3-isopropoxyphenyl)amino]ethyl]piperidin-4-ol Processing the compound (7.0 g) obtained through Step 1 above, as in Step 4 of Example 1 gave the designated compound (6.52 g).

<Step 3> Synthesis of 4-[2-[N-methyl-N-(3-isopropoxyphenyl)-amino]ethyl]piperidin-4-ol Processing the compound (6.0 g) obtained through Step 2 above, as in Step 3 of Example 42 gave the designated compound (4.63 g).

<Step 4> Synthesis of 1-[2-(4-cyanophenyl)ethyl]-4-[2-[N-methyl-N-(3-isopropoxyphenyl)amino]ethyl]piperidin-4-ol Processing the compound (0.50 g) obtained through Step 3 above and 4-cyanophenylacetaldehyde (0.50 g), as in Step 6 of Example 1 gave the designated compound (0.57 g).

Synthesis of the following compounds were achieved by employing steps similar to Steps 1 to 4 of Example 43.

Example 44

1-[2-(4-cyanophenyl)ethyl]-4-[2-[N-methyl-N-(2-isopropoxyphenyl)amino]ethyl]piperidin-4-ol <Step 1> N-methyl-N-(2-isopropoxyphenyl)-2-(1-benzyl-4-hydroxypiperidin-4-yl)acetamide <Step 2> 1-benzyl-4-[2-[N-methyl-N-(2-isopropoxyphenyl)-amino]ethyl]piperidin-4-ol <Step 3> 4-[2-[N-methyl-N-(2-isopropoxyphenyl)amino]-ethyl]piperidin-4-ol <Step 4> 1-[2-(4-cyanophenyl)ethyl]-4-[2-[N-methyl-N-(2-isopropoxyphenyl)amino]ethyl]piperidin-4-ol Example 45

Synthesis of 1-[2-(4-cyanophenyl)ethyl]-4-[2-[N-(4-isopropoxyphenyl)amino]ethyl]piperidin-4-ol <Step 1> N-(4-isopropoxyphenyl)-2-(1-benzyl-4-hydroxypiperidin-4-yl)acetamide To a solution in anhydrous tetrahydrofuran (80 mL) of the compound obtained through Step 1 of Example 1 (8.0 g) was added under ice-water cooling sodium hydride (60% dispersion in an oil, 1.99 g) under nitrogen atomosphere, and the mixture was stirred for 1 hour at the same temperature. To the reaction mixture cooled to −50° C. was added a solution in anhydrous tetrahydrofuran (80 mL) of lithium diisopropylamide which had been prepared from diisopropylamine (11.6 mL) and n-butyllithium (1.6M solution in hexane, 51.8 mL), and the mixture was stirred at −50 to −30° C. for 1 hour. At this moment, a solution in anhydrous tetrahydrofuran (40 mL) of 1-benzylpiperidin-4-one (7.83 g) was added at −30° C., and the mixture was stirred at −30° C. for 30 minutes, and for 2 hours under ice-water cooling. The mixture was poured into ice-water, and was extracted with ethyl acetate. The organic layer was washed with water and saturated aqueous solution of salt in this order, dried with anhydrous sodium sulfate, and had its solvent eliminated through evaporation under a reduced pressure. The residue thus obtained was submitted to silica gel column chromatography (eluent; methylene chloride:methanol=90:10 to 75:25) for purification, to give the designated compound (10.3 g).

<Step 2> Synthesis of 1-benzyl-4-[2-[N-(4-isopropoxyphenyl)-amino]ethyl]piperidin-4-ol Processing the compound (9.9 g) obtained through Step 1 above, as in Step 4 of Example 1 gave the designated compound (4.4 g).

<Step 3> Synthesis of 4-[2-[N-(4-isopropoxyphenyl)amino]-ethyl]piperidin-4-ol

Processing the compound (4.3 g) obtained through Step 2 above, as in Step 3 of Example 42 gave the designated compound (3.2 g).

<Step 4> Synthesis of 1-[2-(4-cyanophenyl)ethyl]-4-[2-[N-(4-isopropoxyphenyl)amino]ethyl]piperidin-4-ol Processing the compound (0.50 g) obtained through Step 3 above and 4-cyanophenylacetaldehyde (0.31 g), as in Step 6 of Example 1 gave the designated compound (0.17 g).

Example 46

Synthesis of 1-[2-(4-cyanophenyl)ethyl]-4-[2-[N-methyl-N-(4-isopropoxyphenyl)amino]-1-hydroxyethyl]piperidin-4-ol <Step 1> Synthesis of N-methyl-N-(4-isopropoxyphenyl)-2-(1-benzyl-4-hydroxypiperidin-4-yl)-2-benzyloxyacetamide Processing 2-benzyloxy-4'-isopropoxy-N-methylacetanilide (5.20 g) as in Step 1 of Example 43 gave the designated compound (7.35 g)

<Step 2> Synthesis of N-methyl-N-(4-isopropoxyphenyl)-2-hydroxy-2-(4-hydroxypiperidin-4-yl)acetamide To a solution in methanol (100 mL) of the compound (7.35 g) obtained through Step 1 above were added ammonium formate (17.2 g) and 10% palladium on carbon (1.04 g), and the mixture was heated under reflux for 6.5 hours. After cooling, the catalyst was filtered off, and the filtrate was condensed to dryness under a reduced pressure. The residue thus obtained was submitted to silica gel column chromatography (Chromatorex NH™) (eluent; methylene chloride:methanol=99:1 to 95:5) for purification, to give the designated compound (2.80 g).

<Step 3> Synthesis of 4-[2-[N-methyl-N-(4-isopropoxyphenyl)-amino]-1-hydroxyethyl]piperidin-4-ol Processing the compound (0.7 g) obtained through Step 2 above, as in Step 4 of Example 1 gave the designated compound (0.5 g).

<Step 4> Synthesis of 1-[2-(4-cyanophenyl)ethyl]-4-[2-[N-methyl-N-(4-isopropoxyphenyl)amino]-1-hydroxyethyl]piperidin-4-ol Processing the compound (0.40 g) obtained through Step 3 above and 4-cyanophenylacetaldehyde (0.38 g), as in Step 6 of Example 1 gave the designated compound (0.45 g).

Example 47

Synthesis of 1-[2-(4-cyanophenyl)ethyl]-4-methoxy-4-[2-[N-methyl-N-(4-isopropoxyphenyl)amino]ethyl]piperidine <Step 1> Synthesis of N-methyl-N-(4-isopropoxyphenyl)-2-(1-tert-butoxycarbonyl-4-hydroxypiperidin-4-yl)acetamide Processing 1-tert-butoxycarbonylpiperidin-4-one (6.7 g) and the compound (7.0 g) obtained through Step 2 of Example 1, as in Step 1 of Example 43 gave the designated compound (9.5 g).

<Step 2> Synthesis of N-methyl-N-(4-isopropoxyphenyl)-2-(1-tert-butoxycarbonyl-4-methoxypiperidin-4-yl)acetamide To a solution in anhydrous dimethylformamide (80 mL) of the compound (8.50 g) obtained through Step 1 above was added under ice-water cooling sodium hydride (60% dispersion in an oil, 1.26 g), and the mixture was stirred for 1 hour. Then, the mixture received the addition of methyl iodide (1.96 mL), and was stirred for 15 minutes, and then stirred at room temperature for further 5 hours. The reaction mixture received the addition of water and was extracted with ethyl acetate. The organic layer was washed with water and saturated aqueous solution of salt, dried with anhydrous sodium sulfate, and had its solvent eliminated through evaporation under a reduced pressure. The residue thus obtained was submitted to silica gel column chromatography (eluent; methylene chloride:ethyl acetate 1:1) for purification to give the designated compound (5.22 g).

<Step 3> Synthesis of 4-methoxy-4-[2-[N-methyl-N-(4-isopropoxyphenyl)amino]ethyl]piperidine Processing the compound (4.7 g) obtained through Step 2 above, as in Step 4 of Example 1 gave the designated compound (2.52 g).

<Step 4> Synthesis of 1-[2-(4-cyanophenyl)ethyl]-4-methoxy-4-[2-[N-methyl-N-(4-isopropoxyphenyl)amino]ethyl]piperidine Processing the compound (0.50 g) obtained through Step 3 above and 4-cyanophenylacetaldehyde (0.47 g), as in Step 6 of Example 1 gave the designated compound (0.66 g).

Example 48

Synthesis of 1-[2-(4-cyanophenyl)ethyl]-4-[N-methyl-N-(4-isopropoxyphenyl)aminomethyl]piperidin-4-ol <Step 1> Synthesis of 1-benzyl-4-[N-methyl-N-(4-isopropoxyphenyl)aminomethyl]piperidin-4-ol To a solution in diethyl ether (70 mL) of 1-benzylpiperidin-4-spiro-2'-oxirane (3.45 g) and N-methyl-4-isopropoxyaniline (3.37 g) was added activated neutral aluminum oxide 90 (35 g) (activity I, Merck), and the mixture was stirred at room temperature overnight. The reaction mixture received the addition of methanol (140 mL), and was stirred at room temperature for 3.5 hours. The reaction mixture was filtered and the filtrate was condensed to dryness under a reduced pressure. The residue thus obtained was submitted to silica gel column chromatography (eluent; ethyl acetate) for purification, to give the designated compound (2.43 g).

<Step 2> Synthesis of 4-[N-methyl-N-(4-isopropoxyphenyl)-aminomethyl]piperidin-4-ol Processing the compound (2.40 g) obtained through Step 1 above, as in Step 3 of Example 42 gave the designated compound (1.81 g).

<Step 3> Synthesis of 1-[2-(4-cyanophenyl)ethyl]-4-[N-methyl-N-(4-isopropoxyphenyl)aminomethyl]piperidin-4-ol Processing the compound (0.50 g) obtained through Step 2 above and 4-cyanophenylacetaldehyde (0.52 g), as in Step 6 of Example 1 gave the designated compound (0.62 g).

Example 49

Synthesis of 1-[2-(4-cyanophenyl)ethyl]-4-[2-[N-methyl-N-(4-isopropoxyphenyl)amino]ethyl]piperidin-4-ol <Step 1> Synthesis of N-methyl-N-(4-isopropoxyphenyl)-2-[1-[2-(4-cyanophenyl)ethyl]-4-hydroxypiperidin-4-yl]acetamide Processing the compound obtained through Step 2 of Example 1 and 1-[2-(4-cyanophenyl)ethyl]-piperidin-4-one, as in Step 1 of Example 43 gave the designated compound.

<Step 2> Synthesis of 1-[2-(4-cyanophenyl)ethyl]-4-[2-[N-methyl-N-(4-isopropoxyphenyl)amino]ethyl]piperidin-4-ol To a solution in anhydrous tetrahydrofuran of the compound obtained through Step 1 above was added under ice-water cooling borane-methyl sulfide complex, and the mixture was stirred at the same temperature for 4 hours. The mixture received the addition of methanol and 10% hydrogen chloride in methanol, and was heated under reflux for 30 minutes. After cooling, the solvent was evaporated under a reduced pressure; saturated aqueous solution of sodium hydrogencarbonate was added to make the mixture alkaline; and the mixture was extracted with ethyl acetate. The organic layer was dried with anhydrous sodium sulfate, and had its solvent eliminated through evaporation under a reduced pressure. The residue thus obtained was submitted to silica gel column chromatography (Chromatorex NH™) (eluent; ethyl acetate:hexane=1:2 to 1:1) for purification to give the designated compound.

Example 50

Preparation of 4-[2-[N-methyl-N-(4-isopropoxyphenyl)-amino]ethyl]-1-(2-phenylethyl)piperidin-4-ol dihydrochloride To a solution in 2-propanol of the compound (4.5 g) obtained through Step 6 of Example 1 was added 10% hydrogen chloride in methanol (40 mL), and the mixture had its solvent eliminated through evaporation under a reduced pressure. The residue thus obtained was crystallized through the addition of 2-propanol plus diethyl ether, and recrystallized from 2-propanol, to give the designated compound (2.97 g).

The following hydrochlorides were obtained in the same manner as in Example 50.

Example 51

1-[2-(4-cyanophenyl)ethyl]-4-[2-[N-methyl-N-(4-isopropoxyphenyl)amino]ethyl]piperidin-4-ol dihydrochloride

Example 52

1-[2-[4-(methoxycarbonyl)phenyl]ethyl]-4-[2-[N-methyl-N-(4-isopropoxyphenyl)amino]ethyl]piperidin-4-ol dihydrochloride

Example 53

1-[2-[4-(ethoxycarbonyl)phenyl]ethyl]-4-[2-[N-methyl-N-(4-isopropoxyphenyl)amino]ethyl]piperidin-4-ol dihydrochloride

Example 54

4-[2-[N-methyl-N-(4-isopropoxyphenyl)amino]ethyl]-1-[2-(4-methylsulfinylphenyl)ethyl]piperidin-4-ol dihydrochloride

Example 55

1-[2-(4-fluorophenyl)ethyl]-4-[2-[N-methyl-N-(4-isopropoxyphenyl)amino]ethyl]piperidin-4-ol dihydrochloride

Example 56

4-[2-[N-methyl-N-(4-isopropoxyphenyl)amino]ethyl]-1-[2-(4-nitrophenyl)ethyl]piperidin-4-ol dihydrochloride

Example 57

1-[2-(3-cyanophenyl)ethyl]-4-[2-[N-methyl-N-(4-isopropoxyphenyl)amino]ethyl]piperidin-4-ol dihydrochloride

Example 58

1-[2-(3-fluorophenyl)ethyl]-4-[2-[N-methyl-N-(4-isopropoxyphenyl)amino]ethyl]piperidin-4-ol dihydrochloride

Example 59

1-[2-(2-fluorophenyl)ethyl]-4-[2-[N-methyl-N-(4-isopropoxyphenyl)amino]ethyl]piperidin-4-ol dihydrochloride

Example 60

1-[2-(4-chlorophenyl)ethyl]-4-[2-[N-methyl-N-(4-isopropoxyphenyl)amino]ethyl]piperidin-4-ol dihydrochloride

Example 61

1-[2-(3-chlorophenyl)ethyl]-4-[2-[N-methyl-N-(4-isopropoxyphenyl)amino]ethyl]piperidin-4-ol dihydrochloride

Example 62

1-[2-(2-chlorophenyl)ethyl]-4-[2-[N-methyl-N-(4-isopropoxyphenyl)amino]ethyl]piperidin-4-ol dihydrochloride

Example 63

4-[2-[N-methyl-N-(4-isopropoxyphenyl)amino]ethyl]-1-[2-[4-(trifluoromethyl)phenyl]ethyl]piperidin-4-ol dihydrochloride

Example 64

4-[2-[N-methyl-N-(4-isopropoxyphenyl)amino]ethyl]-1-[2-[3-(trifluoromethyl)phenyl]ethyl]piperidin-4-ol dihydrochloride

Example 65

4-[2-[N-methyl-N-(4-isopropoxyphenyl)amino]ethyl]-1-[2-[2-(trifluoromethyl)phenyl]ethyl]piperidin-4-ol dihydrochloride

Example 66

4-[2-[N-methyl-N-(4-isopropoxyphenyl)amino]ethyl]-1-[2-(3-nitorophenyl)ethyl]piperidin-4-ol dihydrochloride

Example 67

4-[2-[N-methyl-N-(4-isopropoxyphenyl)amino]ethyl]-1-[2-(2-nitorophenyl)ethyl]piperidin-4-ol dihydrochloride

Example 68

4-[2-[N-methyl-N-(4-isopropoxyphenyl)amino]ethyl]-1-[2-(4-methylphenyl)ethyl]piperidin-4-ol dihydrochloride

Example 69

4-[2-[N-methyl-N-(4-isopropoxyphenyl)amino]ethyl]-1-[2-(3-methylphenyl)ethyl]piperidin-4-ol dihydrochloride

Example 70

4-[2-[N-methyl-N-(4-isopropoxyphenyl)amino]ethyl]-1-[2-(2-methylphenyl)ethyl]piperidin-4-ol dihydrochloride

Example 71

1-[2-(4-bromophenyl)ethyl]-4-[2-[N-methyl-N-(4-isopropoxyphenyl)amino]ethyl]piperidin-4-ol dihydrochloride

Example 72

1-[2-(3-bromophenyl)ethyl]-4-[2-[N-methyl-N-(4-isopropoxyphenyl)amino]ethyl]piperidin-4-ol dihydrochloride

Example 73

1-[2-(2-bromophenyl)ethyl]-4-[2-[N-methyl-N-(4-isopropoxyphenyl)amino]ethyl]piperidin-4-ol dihydrochloride

Example 74

4-[2-[N-methyl-N-(4-isopropoxyphenyl)amino]ethyl]-1-[2-(4-trifluoromethoxyphenyl)ethyl]piperidin-4-ol dihydrochloride

Example 75

4-[2-[N-methyl-N-(4-isopropoxyphenyl)amino]ethyl]-1-[2-[4-(methylthio)phenyl]ethyl]piperidin-4-ol dihydrochloride

Example 76

4-[2-[N-methyl-N-(4-isopropoxyphenyl)amino]ethyl]-1-[2-(4-methylsulfonylphenyl)ethyl]piperidin-4-ol dihydrochloride

Example 77

4-[2-[N-methyl-N-(4-isopropoxyphenyl)amino]ethyl]-1-[2-(4-sulfamoylphenyl)ethyl]piperidin-4-ol dihydrochloride

Example 78

1-[2-(2-cyanophenyl)ethyl]-4-[2-[N-methyl-N-(4-isopropoxyphenyl)amino]ethyl]piperidin-4-ol dihydrochloride

Example 79

1-[2-(4-carboxyphenyl)ethyl]-4-[2-[N-methyl-N-(4-isopropoxyphenyl)amino]ethyl]piperidin-4-ol dihydrochloride

Example 80

1-[2-(4-carbamoylphenyl)ethyl]-4-[2-[N-methyl-N-(4-isopropoxyphenyl)amino]ethyl]piperidin-4-ol dihydrochloride

Example 81

1-[2-(4-dimethylcarbamoylphenyl)ethyl]-4-[2-[N-methyl-N-(4-isopropoxyphenyl)amino]ethyl]piperidin-4-ol dihydrochloride

Example 82

1-[2-(4-acetylphenyl)ethyl]-4-[2-[N-methyl-N-(4-isopropoxyphenyl)amino]ethyl]piperidin-4-ol dihydrochloride

Example 83

1-[2-(4-fluorophenyl)-2-hydroxyethyl]-4-[2-[N-methyl-N-(4-isopropoxyphenyl)amino]ethyl]piperidin-4-ol dihydrochloride

Example 84

1-[2-(3-furyl)ethyl]-4-[2-[N-methyl-N-(4-isopropoxyphenyl)amino]ethyl]piperidin-4-ol dihydrochloride

Example 85

1-[2-(2-furyl)ethyl]-4-[2-[N-methyl-N-(4-isopropoxyphenyl)amino]ethyl]piperidin-4-ol dihydrochloride

Example 86

4-[2-[N-methyl-N-(4-isopropoxyphenyl)amino]ethyl]-1-[2-(2-thienyl)ethyl]piperidin-4-ol dihydrochloride

Example 87

4-[2-[N-methyl-N-(4-isopropoxyphenyl)amino]ethyl]-1-[2-(3-thienyl)ethyl]piperidin-4-ol dihydrochloride

Example 88

1-[2-(4-(methoxyphenyl)ethyl]-4-[2-[N-methyl-N-(4-isopropoxyphenyl)amino]ethyl]piperidin-4-ol dihydrochloride

Example 89

1-[2-[4-dimethylamino)phenyl]ethyl]-4-[2-[N-methyl-N-(4-isopropoxyphenyl)amino]ethyl]piperidin-4-ol trihydrochloride

Example 90

1-[2-(4-cyanophenyl)ethyl]-4-[2-[N-(4-ethoxyphenyl)-N-methylamino]ethyl]piperidin-4-ol dihydrochloride

Example 91

1-[2-(4-cyanophenyl)ethyl]-4-[2-[N-methyl-N-(3-isopropoxyphenyl)amino]ethyl]piperidin-4-ol dihydrochloride

Example 92

1-[2-(4-cyanophenyl)ethyl]-4-[2-[N-methyl-N-(2-isopropoxyphenyl)amino]ethyl]piperidin-4-ol dihydrochloride

Example 93

1-[2-(4-cyanophenyl)ethyl]-4-[2-[N-(4-isopropoxyphenyl)amino]ethyl]piperidin-4-ol dihydrochloride

Example 94

1-[2-(4-cyanophenyl)ethyl]-4-[2-[N-methyl-N-(4-isopropoxyphenyl)amino]-1-hydroxyethyl]piperidin-4-ol dihydrochloride

Example 95

1-[2-(4-cyanophenyl)ethyl]-4-methoxy-4-[2-[N-methyl-N-(4-isopropoxyphenyl)amino]ethyl]piperidine dihydrochloride

Example 96

1-[2-(4-cyanophenyl)ethyl]-4-[N-methyl-N-(4-isopropoxyphenyl)aminomethyl]piperidin-4-ol dihydrochloride

Example 97

Preparation of 1-[2-(4-cyanophenyl)ethyl]-4-[2-[N-methyl-N-(4-isopropoxyphenyl)amino]ethyl]piperidin-4-ol dihydrobromide To a solution in methanol (362 mL) of the compound (18.1 g) obtained in Example 2 was added 48% hydrobromic acid (9.71 mL), and the solvent was evaporated under a reduced pressure. The residue thus obtained was crystallized through the addition of ethanol plus diethyl ether, and recrystallized from ethanol, to give the designated compound (21.7 g).

Example 98

Preparation of 1-[2-(4-cyanophenyl)ethyl]-4-[2-[N-methyl-N-(4-isopropoxyphenyl)amino]ethyl]piperidin-4-ol dimaleate To a solution in methanol of the compound (16.1 g) obtained in Example 2 was added maleic acid (8.87 g), and the solvent was evaporated under reduced pressure. The residue thus obtained was crystallized through the addition of diethyl ether, and recrystallized twice from 2-propanol, to give the designated compound (18.4 g).

Example 99

Preparation of 1-[2-(4-cyanophenyl)ethyl]-4-[2-[N-methyl-N-(4-isopropoxyphenyl)amino]ethyl]piperidin-4-ol dibenzenesulfonate To a solution in methanol of the compound (14.3 g) obtained in Example 2 was added benzenesulfonic acid monohydrate (12.0 g), and the solvent was evaporated under a reduced pressure. The residue thus obtained was crystallized through the addition of diethyl ether, and recrystallized twice from 2-propanol, to give the designated compound (21.0 g).

The characteristics data of the compounds of Examples 1–51, 55, 84, 86, 90, 93, and 96–99 are listed in Table 5. In the table, for example, Example No. 1-1 refers to Step 1 of Example 1. It should be noted here that in the table, for example, with regard to an example comprising two steps (Steps 1 and 2), the product obtained by Step 1 is not included in the compound of Formula (I), because it serves as an intermediate for the production of the compound of Step 2.

TABLE 5

| Example No. | IR (cm$^{-1}$) | NMR (ppm) (no mark: 300 MHz, *: 270 MHz) | melting point (° C.) |
|---|---|---|---|
| 1-1 | — | CDCl$_3$: 7.36(2H, d, J=9Hz), 7.15(1H, br.s), 6.84(2H, d, J=9Hz), 4.57–4.31(1H, m), 2.15(3H, s), 1.32(6H, d, J=6Hz) | — |
| 1-2 | — | CDCl$_3$: 7.07(2H, d, J=9Hz), 6.89(2H, d, J=9Hz), 4.62–4.47(1H, m), 3.23(3H, s), 1.86(3H, s), 1.36(6H, d, J=6Hz) | — |
| 1-3 | — | CDCl$_3$: 7.37–7.20(5H, m), 7.01(2H, d, J=9Hz), 6.88(2H, d, J=9Hz), 5.26(1H, s), 4.62–4.49(1H, m), 3.47(2H, s), 3.23(3H, s), 2.58–2.49(2H, m), 2.39(2H, ddd, J=11, 11, 2Hz), 2.17(2H, s), 1.71–1.61(2H, m), 1.45–1.31(2H, m), 1.37(6H, d, J=6Hz) | — |
| 1-4 | — | CDCl$_3$: 7.38–7.22(5H, m), 6.86(2H, d, J=9Hz), 6.82(2H, d, J=9Hz), 4.50–4.34(1H, m), 3.54(2H, s), 3.29(2H, t, J=7Hz), 2.78(3H, s), 2.67–2.59(2H, m), 2.46–2.34(2H, m), 1.73–1.62(6H, m), 1.30(6H, d, J=6Hz) | — |
| 1-5 | — | CDCl$_3$*: 6.88(2H, d, J=9Hz), 6.83(2H, d, J=9Hz), 4.50–4.36(1H, m), 3.30(2H, t, J=7Hz), 3.00(2H, ddd, J=12, 12, 3Hz), 2.84(2H, ddd, J=12, 4, 4Hz), 2.78(3H, s), 1.75–1.48(6H, m), 1.31(6H, d, J=6Hz) | — |
| 1-6 | liquid film: 2974, 1510, 1238, 1115 | CDCl$_3$: 7.32–7.16(5H, m), 6.89(2H, d, J=9Hz), 6.84(2H, d, J=9Hz), 4.50–4.37(1H, m), 4.01(1H, br.s), 3.30(2H, t, J=7Hz), 2.88–2.69(4H, m), 2.79(3H, s), 2.67–2.58(2H, m), 1.60(6H, m), 1.31(6H, d, J=6Hz) | oil |
| 2 | KBr: 2979, 2937, 2227, 1512, 1238, 1124, 1093 | CDCl$_3$*: 7.57(2H, d, J=8Hz), 7.31(2H, d, J=8Hz), 6.89(2H, d, J=9Hz), 6.84(2H, d, J=9Hz), 4.50–4.36(1H, m), 3.30(2H, t, J=6Hz), 2.92–2.80(2H, m), 2.78(3H, s), 2.76–2.56(4H, m), 2.45(2H, ddd, J=11, 11, 3Hz), 1.78–1.50(6H, m), 1.31(6H, d, J=6Hz) | 80.4–81.2 |

TABLE 5-continued

| Example No. | IR (cm$^{-1}$) | NMR (ppm) (no mark: 300 MHz, *: 270 MHz) | melting point (° C.) |
|---|---|---|---|
| 3 | KBr: 1718, 1514, 1277, 1242, 1111 | CDCl$_3$: 7.96(2H, d, J=8Hz), 7.28(2H, d, J=8Hz), 6.90(2H, d, J=9Hz), 6.83(2H, d, J=9Hz), 4.50–4.38(1H, m), 3.90(3H, s), 3.30(2H, t, J=7Hz), 2.93–2.40(8H, m), 2.78(3H, s), 1.80–1.60(6H, m), 1.31(6H, d, J=6Hz) | 85.8–87.4 |
| 4 | KBr: 1711, 1514, 1279, 1240, 1109 | CDCl$_3$: 7.96(2H, d, J=8Hz), 7.27(2H, d, J=8Hz), 6.89(2H, d, J=9Hz), 6.84(2H, d, J=9Hz), 4.50–4.35(1H, m), 4.36(2H, q, J=7Hz), 3.30(2H, t, J=7Hz), 2.92–2.60(6H, m), 2.79(3H, s), 2.46(2H, ddd, J=11, 11, 3Hz), 1.78–1.58(6H, m), 1.39(3H, t, J=7Hz), 1.31(6H, d, J=6Hz) | 54.4–56.0 |
| 5 | liquid film: 2937, 1512, 1371, 1238, 1114, 1088 | CDCl$_3$*: 7.56(2H, d, J=7Hz), 7.37(2H, d, J=7Hz), 6.89(2H, d, J=9Hz), 6.83(2H, d, J=9Hz), 4.50–4.36(1H, m), 3.30(2H, t, J=6Hz), 2.92–2.82(1H, m), 2.78(3H, s), 2.76–2.56(4H, m), 2.71(3H, s), 2.53–2.39(2H, m), 1.80–1.52(6H, m), 1.31(6H, d, J=6Hz) | oil |
| 6 | KBr: 1512, 1238, 1215, 1117, 1093 | CDCl$_3$: 7.15(2H, dd, J=9, 5Hz), 6.96(2H, dd, J=9, 9Hz), 6.89(2H, d, J=9Hz), 6.83(2H, d, J=9Hz), 4.50–4.37(1H, m), 4.03(1H, s), 3.30(2H, t, J=7Hz), 2.83–2.67(4H, m), 2.78(3H, s), 2.63–2.55(2H, m), 2.44(2H, ddd, J=11, 11, 3Hz), 1.78–1.59(6H, m), 1.31(6H, d, J=6Hz) | 84.7–85.2 |
| 7 | liquid film: 2937, 1514, 1344, 1238, 1111 | CDCl$_3$*: 8.14(2H, d, J=9Hz), 7.36(2H, d, J=9Hz), 6.89(2H, d, J=9Hz), 6.84(2H, d, J=9Hz), 4.50–4.36(1H, m), 3.30(2H, t, J=7Hz), 2.96–2.86(2H, m), 2.78(3H, s), 2.75–2.60(4H, m), 2.47(2H, ddd, J=11, 11, 3Hz), 1.80–1.50(6H, m), 1.31(6H, d, J=6Hz) | oil |
| 8 | liquid film: 2937, 2224, 1510, 1238, 1115 | CDCl$_3$: 7.52–7.35(4H, m), 6.90(2H, d, J=9Hz), 6.84(2H, d, J=9Hz), 4.50–4.37(1H, m), 3.30(2H, t, J=7Hz), 2.90–2.56(6H, m), 2.79(3H, s), 2.45(2H, ddd, J=11, 11, 3Hz), 1.78–1.56(6H, m), 1.31(6H, d, J=6Hz) | oil |
| 9-1 | — | CDCl$_3$: 7.32–7.23(1H, m), 7.05–6.90(5H, m), 6.84(2H, d, J=9Hz), 4.52–4.34(2H, m), 3.73(2H, s), 3.65–3.55(1H, m), 3.49–3.37(1H, m), 3.23(2H, t, J=6Hz), 3.09(1H, ddd, J=13, 13, 3Hz), 2.76(3H, s), 1.75–1.55(4H, m), 1.44(1H, ddd, J=13, 13, 5Hz), 1.31(6H, d, J=6Hz), 1.21(1H, ddd, J=13, 13, 5Hz) | — |
| 9-2 | liquid film: 2937, 1510, 1240, 1115 | CDCl$_3$*: 7.28–7.18(1H, m), 7.01–6.78(7H, m), 4.50–4.37(1H, m), 4.05(1H, br.s), 3.30(2H, t, J=7Hz), 2.87–2.58(6H, m), 2.78(3H, s), 2.46(2H, ddd, J=11, 11, 3Hz), 1.80–1.53(6H, m), 1.31(6H, d, J=6Hz) | oil |
| 10-1 | — | CDCl$_3$*: 7.34–7.18(2H, m), 7.13–7.00(2H, m), 6.92(2H, d, J=9Hz), 6.84(2H, d, J=9Hz), 4.50–4.33(2H, m), 3.82–3.60(3H, m), 3.53–3.40(1H, m), 3.24(2H, t, J=6Hz), 3.10(1H, ddd, J=13, 13, 3Hz), 2.76(3H, s), 1.75–1.22(6H, m), 1.31(6H, d, J=6Hz) | — |

TABLE 5-continued

| Example No. | IR (cm⁻¹) | NMR (ppm) (no mark: 300 MHz, *: 270 MHz) | melting point (° C.) |
|---|---|---|---|
| 10-2 | liquid film: 2937, 1510, 1493, 1238, 1115 | CDCl$_3$*: 7.25–7.13(2H, m), 7.09–6.97(2H, m), 6.88(2H, d, J=9Hz), 6.84(2H, d, J=9Hz), 4.50–4.36(1H, m), 3.94(1H, br.s), 3.30(2H, t, J=7Hz), 2.91–2.68(4H, m), 2.79(3H, s), 2.67–2.57(2H, m), 2.48(2H, ddd, J=11, 11, 3Hz), 1.78–1.58(6H, m), 1.31(6H, d, J=6Hz) | oil |
| 11-1 | — | CDCl$_3$*: 7.28(2H, d, J=8Hz), 7.19(2H, d, J=8Hz), 6.92(2H, d, J=9Hz), 6.83(2H, d, J=9Hz), 4.89(1H, br.s), 4.52–4.30(2H, m), 3.69(2H, s), 3.65–3.54(1H, m), 3.43(1H, ddd, J=13, 13, 3Hz), 3.23(2H, t, J=6Hz), 3.08(1H, ddd, J=13, 13, 3Hz), 2.75(3H, s), 1.75–1.50(4H, m), 1.42(1H, ddd, J=13, 13, 5Hz), 1.31(6H, d, J=6Hz), 1.21(1H, ddd, J=13, 13, 4Hz) | — |
| 11-2 | KBr: 2937, 1512, 1236, 1119, 1093 | CDCl$_3$*: 7.25(2H, d, J=8Hz), 7.13(2H, d, J=8Hz), 6.89(2H, d, J=9Hz), 6.83(2H, d, J=9Hz), 4.50–4.36(1H, m), 4.02(1H, br.s), 3.30(2H, t, J=7Hz), 2.85–2.64(4H, m), 2.78(3H, s), 2.63–2.53(2H, m), 2.44(2H, ddd, J=11, 11, 3Hz), 1.79–1.52(6H, m), 1.31(6H, d, J=6Hz) | 92.1–94.0 |
| 12-1 | — | CDCl$_3$: 7.28–7.11(4H, m), 6.92(2H, d, J=9Hz), 6.83(2H, d, J=9Hz), 4.89(1H, br.s), 4.52–4.35(2H, m, 3.71(2H, s), 3.65–3.54(1H, m), 3.44(1H, ddd, J=13, 13, 3Hz), 3.26–3.20(2H, m), 3.09(1H, ddd, J=13, 13, 3Hz), 2.75(3H, s), 1.75–1.57(4H, m), 1.44(1H, ddd, J=13, 13, 5Hz), 1.31(6H, d, J=6Hz), 1.28–1.17(1H, m) | — |
| 12-2 | liquid film: 2937, 1510, 1238, 1115 | CDCl$_3$: 7.24–7.14(3H, m), 7.11–7.06(1H, m), 6.89(2H, d, J=9Hz), 6.84(2H, d, J=9Hz), 4.50–4.37(1H, m), 3.30(2H, t, J=7Hz), 2.85–2.55(6H, m), 2.78(3H, s), 2.46(2H, ddd, J=11, 11, 3Hz), 1.77–1.53(6H, m), 1.31(6H, d, J=6Hz) | oil |
| 13-1 | — | CDCl$_3$: 7.40–7.16(4H, m), 6.92(2H, d, J=9Hz), 6.84(2H, d, J=9Hz), 4.84(1H, br.s), 4.51–4.36(2H, m), 3.85(1H, d, J=16Hz), 3.80(1H, d, J=16Hz), 3.65–3.55(1H, m), 3.46(1H, ddd, J=13, 13, 3Hz), 3.29–3.21(2H, m), 3.12(1H, ddd, J=13, 13, 3Hz), 2.76(3H, s), 1.76–1.58(4H, m), 1.47(1H, ddd, J=13, 13, 5Hz), 1.35–1.24(1H, m), 1.31(6H, d, J=6Hz) | — |
| 13-2 | liquid film: 2937, 1510, 1238, 1113 | CDCl$_3$: 7.33(1H, dd, J=7, 3Hz), 7.26–7.10(3H, m), 6.89(2H, d, J=9Hz), 6.84(2H, d, J=9Hz), 4.50–4.37(1H, m), 3.31(2H, t, J=7Hz), 3.00–2.92(2H, m), 2.82–2.71(2H, m), 2.79(3H, s), 2.66–2.58(2H, m), 2.50(2H, ddd, J=11, 11, 4Hz), 1.80–1.60(6H, m), 1.31(6H, d, J=6Hz) | oil |
| 14-1 | — | CDCl$_3$: 7.57(2H, d, J=8Hz), 7.37(2H, d, J=8Hz), 6.92(2H, d, J=9Hz), 6.83(2H, d, J=9Hz), 4.97(1H, br.s), 4.50–4.35(2H, m), 3.78(2H, s), 3.65–3.55(1H, m), 3.45(1H, ddd, J=13, 13, 2Hz), 3.23(2H, t, J=6Hz), 3.09(1H, ddd, J=13, 13, 3Hz), 2.75(3H, s), 1.77–1.55(4H, m), 1.43(1H, ddd, J=13, 13, 5Hz), 1.31(6H, d, J=6Hz), 1.24(1H, ddd, J=13, 13, 5Hz) | — |
| 14-2 | KBr: 1510, 1327, 1236, 1159, 1120 | CDCl$_3$*: 7.53(2H, d, J=8Hz), 7.32(2H, d, d=8Hz), 6.89(2H, d, J=9Hz), 6.84(2H, d, J=9Hz), 4.50–4.37(1H, m), 4.08(1H, br.s), 3.30(2H, t, J=7Hz), 2.92–2.58(6H, m), 2.78(3H, s), 2.46(2H, ddd, J=11, 11, 3Hz), 1.80–1.52(6H, m), 1.31(6H, d, J=6Hz) | 80.2–81.4 |
| 15-1 | — | CDCl$_3$: 7.54–7.42(4H, m), 6.92(2H, d, J=9Hz), 6.83(2H, d, J=9Hz), 4.51–4.36(2H, m), 3.79(2H, s), 3.66–3.57(1H, m), 3.46(1H, ddd, J=13, 13, 3Hz), 3.26–3.20(1H, m), 2.75(3H, s), 1.76–1.57(4H, m), 1.44(1H, ddd, J=13, 13, 5Hz), 1.31(6H, d, J=6Hz), 1.22(1H, ddd, J=13, 13, 5Hz) | — |
| 15-2 | liquid film: 2939, 1510, 1333, 1122 | CDCl$_3$: 7.48–7.38(4H, m), 6.89(2H, d, J=9Hz), 6.84(2H, d, J=9Hz), 4.50–4.38(1H, m), 3.30(2H, t, J=7Hz), 2.92–2.41(8H, m), 2.79(3H, s), 1.78–1.55(6H, m), 1.31(6H, d, J=6Hz) | oil |
| 16-1 | — | CDCl$_3$: 7.65(1H, d, J=8Hz), 7.50(1H, dd, J=7, 7Hz), 7.39–7.32(2H, m), 6.93(2H, d, J=9Hz), 6.84(2H, d, J=9Hz), 4.90(1H, br.s), 4.51–4.37(2H, m), 3.92(1H, d, J=16Hz), 3,85(1H, d, J=16Hz), 3.62–3.40(2H, m), 3.25(2H, t, J=6Hz), 3.19–3.07(1H, m), 2.76(3H, s), 1.78–1.32(6H, m), 1.31(6H, d, J=6Hz) | — |
| 16-2 | liquid film: 1510, 1315, 1240, 1115 | CDCl$_3$: 7.61(1H, d, J=8Hz), 7.47(1H, dd, J=8, 8Hz), 7.37–7.28(2H, m), 6.89(2H, d, J=9Hz), 6.84(2H, d, J=9Hz), 4.50–4.38(1H, m), 3.31(2H, t, J=7Hz), 3.04–2.97(2H, m), 2.79(3H, s), 2.78–2.45(6H, m), 1.80–1.55(6H, m), 1.31(6H, d, J=6Hz) | oil |
| 17-1 | — | CDCl$_3$: 8.15–8.07(2H, m), 7.64–7.45(2H, m), 6.93(2H, d, J=9Hz), 6.84(2H, d, J=9Hz), 5.03(1H, br.s), 4.52–4.34(2H, m), 3.82(2H, s), 3.70–3.60(1H, m), 3.51(1H, ddd, J=13, 13, 3Hz), 3.25(2H, t, J=6Hz), 3.11(1H, ddd, J=13, 13, 2Hz), 2.76(3H, s), 1.80–1.20(6H, m), 1.32(6H, d, J=6Hz) | — |
| 17-2 | liquid film: 2937, 1527, 1510, 1350, 1238, 1115 | CDCl$_3$*: 8.12–8.03(2H, m), 7.54(1H, d, J=8Hz), 7.44(1H, dd, J=8, 8Hz), 6.89(2H, d, J=9Hz), 6.84(2H, d, J=9Hz), 4.50–4.36(1H, m), 3.30(2H, t, J=6Hz), 2.96–2.86(2H, m), 2.79(3H, s), 2.76–2.61(4H, m), 2.47(2H, ddd, J=11, 11, 3Hz), 1.80–1.55(6H, m), 1.31(6H, d, J=6Hz) | oil |

TABLE 5-continued

| Example No. | IR (cm$^{-1}$) | NMR (ppm) (no mark: 300 MHz, *: 270 MHz) | melting point (° C.) |
|---|---|---|---|
| 18-1 | — | CDCl$_3$*: 8.10(1H, dd, J=8, 1Hz), 7.54(1H, ddd, J=7, 7, 1Hz), 7.47–7.39(1H, m), 7.36–7.30(1H, m), 6.94(2H, d, J=9Hz), 6.85(2H, d, J=9Hz), 4.89(1H, br.s), 4.52–4.30(2H, m), 4.23(1H, d, J=16Hz), 3.91(1H, d, J=16Hz), 3.78–3.67(1H, m), 3.58(1H, ddd, 13, 13, 3Hz), 3.29(2H, t, J=6Hz), 3.11(1H, ddd, J=13, 13, 2Hz), 2.78(3H, s), 1.83–1.45(6H, m), 1.32(6H, d, J=6Hz) | — |
| 18-2 | liquid film: 2937, 1525, 1510, 1350, 1238, 1115 | CDCl$_3$: 7.89(1H, dd, J=8, 1Hz), 7.52(1H, ddd, J=8, 8, 1Hz), 7.39–7.32(2H, m), 6.88(2H, d, J=9Hz), 6.83(2H, d, J=9Hz), 4.50–4.36(1H, m), 3.89(1H, br.s), 3.30(2H, t, J=7Hz), 3.15–3.05(2H, m), 2.79(3H, s), 2.74–2.62(4H, m), 2.51(2H, ddd, J=11, 11, 3Hz), 1.76–1.56(6H, m), 1.31(6H, d, J=6Hz) | oil |
| 19-1 | — | CDCl$_3$*: 7.16–7.08(4H, m), 6.90(2H, d, J=9Hz), 6.83(2H, d, J=9Hz), 4.73(1H, br.s), 4.52–4.32(2H, m), 3.70(2H, s), 3.68–3.57(1H, m), 3.40(1H, ddd, J=13, 13, 2Hz), 3.22(2H, t, J=6Hz), 3.08(1H, ddd, J=13, 13, 3Hz), 2.74(3H, s), 2.32(3H, s), 1.75–1.50(4H, m), 1.43(1H, ddd, J=13, 13, 5Hz), 1.31(6H, d, J=6Hz), 1.18(1H, ddd, J=13, 13, 5Hz) | — |
| 19-2 | liquid film: 2974, 1512, 1240, 1115 | CDCl$_3$*: 7.13–7.05(4H, m), 6.88(2H, d, J=9Hz), 6.83(2H, d, J=9Hz), 4.50–4.36(1H, m), 3.96(1H, br.s), 3.30(2H, t, J=7Hz), 2.83–2.67(4H, m), 2.78(3H, s), 2.67–2.56(2H, m), 2.45(2H, ddd, J=11, 11, 4Hz), 2.31(3H, s), 1.81–1.60(6H, m), 1.31(6H, d, J=6Hz) | oil |
| 20-1 | — | CDCl$_3$: 7.19(1H, d, J=8Hz), 7.09–7.01(3H, m), 6.90(2H, d, J=9Hz), 6.83(2H, d, J=9Hz), 4.51–4.34(2H, m), 3.70(2H, s), 3.67–3.58(1H, m), 3.40(1H, ddd, J=13, 13, 3Hz), 3.22(2H, t, J=6Hz), 3.09(1H, ddd, J=13, 13, 3Hz), 2.75(3H, s), 2.32(3H, s), 1.74–1.50(4H, m), 1.43(1H, ddd, J=13, 13, 5Hz), 1.31(6H, d, J=6Hz), 1.18(1H, ddd, J=13, 13, 5Hz) | — |
| 20-2 | liquid film: 2937, 1510, 1238, 1115 | CDCl$_3$: 7.21–7.14(1H, m), 7.04–6.98(2H, m), 6.89(2H, d, J=9Hz), 6.84(2H, d, J=9Hz), 4.49–4.37(1H, m), 3.30(2H, t, J=7Hz), 2.83–2.63(4H, m), 2.79(3H, s), 2.65–2.58(2H, m), 2.46(2H, ddd, J=11, 11, 4Hz), 2.33(3H, s), 1.78–1.60(6H, m), 1.31(6H, d, J=6Hz) | oil |
| 21-1 | — | CDCl$_3$: 7.18–7.10(4H, m), 6.91(2H, d, J=9Hz), 6.83(2H, d, J=9Hz), 4.49–4.37(2H, m), 3.68(2H, s), 3.57–3.47(1H, m), 3.43(1H, ddd, J=13, 13, 3Hz), 3.24(2H, t, J=6Hz), 3.13(1H, ddd, J=13, 13, 3Hz), 2.75(3H, s), 2.49(3H, s), 1.78–1.20(6H, m), 1.31(6H, d, J=6Hz) | — |
| 21-2 | liquid film: 2937, 1510, 1238, 1113 | CDCl$_3$: 7.17–7.09(4H, m), 6.89(2H, d, J=9Hz), 6.83(2H, d, J=9Hz), 4.45–4.38(1H, m), 3.31(2H, t, J=7Hz), 2.87–2.72(4H, m), 2.79(3H, s), 2.60–2.52(2H, m), 2.48(2H, ddd, J=11, 11, 3Hz), 2.33(3H, s), 1.80–1.50(6H, m), 1.31(6H, d, J=6Hz) | oil |
| 22-1 | — | CDCl$_3$: 7.43(2H, d, J=8Hz), 7.13(2H, d, J=8Hz), 6.92(2H, d, J=9Hz), 6.84(2H, d, J=9Hz), 4.91(1H, br.s), 4.50–4.33(2H, m), 3.68(2H, s), 3.65–3.55(1H, m), 3.43(1H, ddd, J=13, 13, 3Hz), 3.23(2H, t, J=6Hz), 3.08(1H, ddd, J=13, 13, 3Hz), 2.75(3H, s), 1.75–1.55(4H, m), 1.42(1H, ddd, J=13, 13, 5Hz), 1.31(6H, d, J=6Hz), 1.21(1H, ddd, J=13, 13, 5Hz) | — |
| 22-2 | KBr: 2937, 1510, 1236, 1119, 1093 | CDCl$_3$: 7.39(2H, d, J=8Hz), 7.08(2H, d, J=8Hz), 6.89(2H, d, J=9Hz), 6.83(2H, d, J=9Hz), 4.50–4.35(1H, m), 4.03(1H, br.s), 3.30(2H, t, J=6Hz), 2.85–2.53(6H, m), 2.78(3H, s), 2.44(2H, ddd, J=11, 11, 3Hz), 1.77–1.50(6H, m), 1.31(6H, d, J=6Hz) | 91.7–92.5 |
| 23-1 | — | CDCl$_3$*: 7.42–7.32(2H, m), 7.27–7.15(2H, m), 6.91(2H, d, J=8Hz), 6.83(2H, d, J=8Hz), 4.50–4.33(2H, m), 3.70(2H, s), 3.65–3.02(5H, m), 2.75(3H, s), 1.75–1.15(6H, m), 1.31(6H, d, J=6Hz) | — |
| 23-2 | liquid film: 2974, 1510, 1238, 1113 | CDCl$_3$: 7.37–7.30(2H, m), 7.17–7.12(2H, m), 6.89(2H, d, J=9Hz), 6.84(2H, d, J=9Hz), 4.50–4.37(1H, m), 3.30(2H, t, J=7Hz), 2.83–2.66(4H, m), 2.78(3H, s), 2.64–2.56(2H, m), 2.45(2H, ddd, J=11, 11, 3Hz), 1.78–1.58(6H, m), 1.31(6H, d, J=6Hz) | oil |
| 24-1 | — | CDCl$_3$: 7.58–7.53(1H, m), 7.32–7.25(2H, m), 7.15–7.06(1H, m), 6.92(2H, d, J=9Hz), 6.84(2H, d, J=9Hz), 4.87(1H, br.s), 4.50–4.35(2H, m), 3.87(1H, d, J=16Hz), 3.80(1H, d, J=16Hz), 3.64–3.55(1H, m), 3.46(1H, ddd, J=13, 13, 3Hz), 3.25(2H, t, J=6Hz), 3.12(1H, ddd, 13, 13, 3Hz), 2.76(3H, s), 1.77–1.30(6H, m), 1.31(6H, d, J=6Hz) | — |
| 24-2 | liquid film: 2972, 1510, 1238, 1113 | CDCl$_3$*: 7.52(1H, d, J=8Hz), 7.27–2.18(2H, m), 7.11–7.00(1H, m), 6.88(2H, d, J=9Hz), 6.84(2H, d, J=9Hz), 4.50–4.36(1H, m), 3.31(2H, t, J=7Hz), 3.01–2.91(2H, m), 2.81–2.71(2H, m), 2.79(3H, s), 2.67–2.56(2H, m), 2.51(2H, ddd, J=11, 11, 3Hz), 1.78–1.60(6H, m), 1.31(6H, d, J=6Hz) | oil |
| 25-1 | — | CDCl$_3$: 7.27(2H, d, J=8Hz), 7.16(2H, d, J=8Hz), 6.92(2H, d, J=9Hz), 6.83(2H, d, J=9Hz), 4.93(1H, br.s), 4.51–4.34(2H, m), 3.73(2H, s), 3.66–3.56(1H, m), 3.45(1H, ddd, J=13, 13, 3Hz), 3.28–3.18(2H, m), 3.09(1H, ddd, J=13, 13, 3Hz), 2.75(3H, s), 1.76–1.58(4H, m), 1.43(1H, ddd, J=13, 13, 5Hz), 1.31(6H, d, J=6Hz), 1.21(1H, ddd, J=13, 13, 5Hz) | — |
| 25-2 | liquid film: 2939, 1510, 1263, 1198, 1163, 1117 | CDCl$_3$: 7.22(2H, d, J=9Hz), 7.13(2H, d, J=9Hz), 6.90(2H, d, J=9Hz), 6.84(2H, d, J=9Hz), 4.50–4.37(1H, m), 3.30(2H, t, J=7Hz), 2.87–2.56(6H, m), 2.78(3H, s), 2.45(2H, ddd, J=11, 11, 3Hz), 1.78–1.58(6H, m), 1.31(6H, d, J=6Hz) | oil |

TABLE 5-continued

| Example No. | IR (cm⁻¹) | NMR (ppm) (no mark: 300 MHz, *: 270 MHz) | melting point (° C.) |
|---|---|---|---|
| 26-1 | — | CDCl$_3$*: 7.20(2H, d, J=7Hz), 7.17(2H, d, J=7Hz), 6.91(2H, d, J=9Hz), 6.83(2H, d, J=9Hz), 4.52–4.32(2H, m), 3.69(2H, s), 3.68–3.54(1H, m), 3.48–3.33(1H, m), 3.22(2H, t, J=6Hz), 3.15–3.01(1H, m), 2.75(3H, s), 2.47(3H, s), 1.75–1.50(4H, m), 1.50–1.13(2H, m), 1.31(6H, d, J=6Hz) | — |
| 26-2 | KBr: 2935, 1510, 1496, 1244, 1117, 818 | CDCl$_3$*: 7.19(2H, d, J=8Hz), 7.14(2H, d, J=8Hz), 6.89(2H, d, J=9Hz), 6.83(2H, d, J=9Hz), 4.50–4.36(1H, m), 3.30(2H, t, J=6Hz), 2.85–2.65(4H, m), 2.78(3H, s), 2.65–2.55(2H, m), 2.55–2.37(2H, m), 2.46(3H, s), 1.80–1.60(6H, m), 1.31(6H, d, J=6Hz) | 67.6–68.8 |
| 27-1 | — | CDCl$_3$*: 7.89(2H, d, J=9Hz), 7.46(2H, d, J=9Hz), 6.93(2H, d, J=9Hz), 6.84(2H, d, J=9Hz), 5.02(1H, br.s), 4.52–4.33(2H, m), 3.81(2H, s), 3.70–3.40(2H, m), 3.24(2H, t, J=6Hz), 3.18–3.03(1H, m), 3.05(3H, s), 2.76(3H, s), 1.82–1.52(4H, m), 1.50–1.20(2H, m), 1.31(6H, d, J=6Hz) | — |
| 27-2 | KBr: 2939, 1514, 1304, 1242, 1146, 1115 | CDCl$_3$*: 7.85(2H, d, J=8Hz), 7.41(2H, d, J=8Hz), 6.89(2H, d, J=9Hz), 6.83(2H, d, J=9Hz), 4.50–4.36(1H, m), 3.30(2H, t, J=6Hz), 3.04(3H, s), 2.98–2.85(2H, m), 2.80–2.56(4H, m), 2.78(3H, s), 2.55–2.40(2H, m), 1.78–1.55(6H, m), 1.31(6H, d, J=6Hz) | 89.1–83.1 |
| 28-1 | — | CDCl$_3$: 7.86(2H, d, J=8Hz), 7.39(2H, d, J=8Hz), 6.93(2H, d, J=9Hz), 6.83(2H, d, J=9Hz), 4.92(2H, br.s), 4.52–4.32(2H, m), 3.79(2H, s), 3.67–3.56(1H, m), 3.48(1H, ddd, J=13, 13, 3Hz), 3.24(2H, t, J=6Hz), 3.09(1H, ddd, J=13, 13, 3Hz), 2.75(3H, s), 1.78–1.60(4H, m), 1.44(1H, ddd, J=13, 13, 5Hz), 1.36–1.24(1H, m), 1.31(6H, d, J=6Hz) | — |
| 28-2 | KBr: 2935, 1510, 1240, 1160 | CDCl$_3$: 7.84(2H, d, J=8Hz), 7.35(2H, d, J=8Hz), 6.90(2H, d, J=9Hz), 6.83(2H, d, J=9Hz), 4.81(2H, br.s), 4.50–4.38(1H, m), 3.30(2H, t, J=6Hz), 2.95–2.58(6H, m), 2.78(3H, s), 2.46(2H, ddd, J=11, 11, 3Hz), 1.83–1.45(6H, m), 1.31(6H, d, J=6Hz) | amorphous |
| 29 | KBr: 2979, 2937, 2227, 1512, 1238, 1124, 1093 | CDCl$_3$*: 7.57(2H, d, J=8Hz), 7.31(2H, d, J=8Hz), 6.89(2H, d, J=9Hz), 6.84(2H, d, J=9Hz), 4.50–4.36(1H, m), 3.30(2H, t, J=6Hz), 2.92–2.80(2H, m), 2.78(3H, s), 2.16–2.56(4H, m), 2.45(2H, ddd, J=11, 11, 3Hz), 1.78–1.50(6H, m), 1.31(6H, d, J=6Hz) | 80.4–81.2 |
| 30 | liquid film: 2937, 2229, 1510, 1238, 1115 | CDCl$_3$: 7.61(1H, d, J=8Hz), 7.55–7.48(1H, m), 7.38–7.26(2H, m), 6.88(2H, d, J=9Hz), 6.84(2H, d, J=9Hz), 4.50–4.37(1H, m), 3.30(2H, t, J=7Hz), 3.10–3.00(2H, m), 2.79(3H, s), 2.78–2.64(4H, m), 2.53(2H, ddd, J=11, 11, 3Hz), 1.87–1.57(6H, m), 1.31(6H, d, J=6Hz) | oil |
| 31 | KBr: 2974, 1510, 1383, 1240 | CD$_3$OD: 7.93(2H, d, J=8Hz), 7.32(2H, d, J=8Hz), 7.85–7.75(4H, m), 4.48–4.35(1H, m), 3.47–3.20(8H, m), 3.14–3.05(2H, m), 2.81(3H, s), 1.92–1.82(4H, m), 1.76–1.66(2H, m), 1.25(6H, d, J=6Hz) | amorphous |
| 32 | KBr: 2976, 1649, 1514, 1383, 1244, 1115 | CDCl$_3$: 7.74(2H, d, J=8Hz), 7.29(2H, d, J=8Hz), 6.90(2H, d, J=9Hz), 6.83(2H, d, J=9Hz), 6.02(1H, br.s), 5.53(1H, br.s), 4.50–4.37(1H, m), 4.08(1H, br.s), 3.30(2H, t, J=7Hz), 2.92–2.83(2H, m), 2.97(3H, s), 2.76–2.59(4H, m), 2.46(2H, ddd, J=11, 11, 3Hz), 1.77–1.54(6H, m), 1.31(6H, d, J=6Hz) | 124.1–126.4 |
| 33 | KBr: 3394, 2931, 1608, 1514, 1242, 1117 | CDCl$_3$: 7.34(2H, d, J=8Hz), 7.23(2H, d, J=8Hz), 6.90(2H, d, J=9Hz), 6.83(2H, d, J=9Hz), 4.50–4.37(1H, m), 4.04(1H, br.s), 3.30(2H, t, J=7Hz), 3.10(3H, s), 2.99(3H, s), 2.88–2.57(6H, m), 2.79(3H, s), 2.45(2H, ddd, J=11, 11, 3Hz), 1.79–1.55(6H, m), 1.31(6H, d, J=6Hz) | 103.2–104.5 |
| 34 | KBr: 2952, 1678, 1512, 1271, 1240 | CDCl$_3$: 7.89(2H, d, J=8Hz), 7.30(2H, d, J=8Hz), 6.90(2H, d, J=9Hz), 6.83(2H, d, J=9Hz), 4.50–4.37(1H, m), 3.30(2H, t, J=7Hz), 2.97–2.40(8H, m), 2.78(3H, s), 2.59(3H, s), 1.81–1.50(6H, m), 1.31(6H, d, J=6Hz) | 93.7–95.9 |
| 35-1 | — | CDCl$_3$: 8.06(2H, dd, J=9, 5Hz), 7.12(2H, dd, J=9, 9Hz), 6.89(2H, d, J=9Hz), 6.83(2H, d, J=9Hz), 4.50–4.36(1H, m), 3.80(2H, s), 3.29(2H, t, J=7Hz), 2.82–2.70(2H, m), 2.78(3H, s), 2.53(2H, ddd, J=10, 10, 5Hz), 1.80–1.65(6H, m), 1.31(6H, d, J=6Hz) | — |
| 35-2 | KBr: 2916, 1510, 1242, 1225, 1115, 835, 825 | CDCl$_3$*: 7.34(2H, dd, J=9, 6Hz), 7.02(2H, dd, J=9, 9Hz), 6.90(2H, d, J=9Hz), 6.84(2H, d, J=9Hz), 4.70(1H, dd, J=11, 4Hz), 4.50–4.36(1H, m), 4.23(1H, br.s), 3.30(2H, t, J=7Hz), 2.94–2.68(2H, m), 2.78(3H, s), 2.60–2.35(4H, m), 1.80–1.50(6H, m), 1.31(6H, d, J=6Hz) | 84.8–85.7 |
| 36 | liquid film: 2937, 1510, 1238, 1115 | CDCl$_3$: 7.35(1H, dd, J=2, 2Hz), 7.28–7.25(1H, m), 6.89(2H, d, J=9Hz), 6.84(2H, d, J=9Hz), 6.31–6.28(1H, m), 4.50–4.37(1H, m), 3.99(1H, br.s), 3.30(2H, t, J=7Hz), 2.79(3H, s), 2.75–2.54(6H, m), 2.43(2H, ddd, J=11, 11, 3Hz), 1.76–1.60(6H, m), 1.31(6H, d, J=6Hz) | oil |
| 37-1 | — | CDCl$_3$: 7.34(1H, dd, J=2, 1Hz), 6.93(2H, d, J=9Hz), 6.84(2H, d, J=9Hz), 6.32(1H, dd, J=3, 2Hz), 6.18(1H, dd, J=3, 1Hz), 4.86(1H, br.s), 4.52–4.32(2H, m), 3.79(1H, d, J=16Hz), 3.81–3.66(2H, m), 3.50(1H, ddd, J=13, 13, 3Hz), 3.25(2H, t, J=6Hz), 3.10(1H, ddd, J=13, 13, 3Hz), 2.76(3H, s), 1.76–1.63(4H, m), 1.52–1.33(2H, m), 1.32(6H, d, J=6Hz) | — |

TABLE 5-continued

| Example No. | IR (cm⁻¹) | NMR (ppm) (no mark: 300 MHz, *: 270 MHz) | melting point (° C.) |
|---|---|---|---|
| 37-2 | liquid film: 2937, 1510, 1238, 1115 | CDCl$_3$: 7.30(1H, dd, J=2, 1Hz), 6.88(2H, d, J=9Hz), 6.83(2H, d, J=9Hz), 6.28(1H, dd, J=3, 2Hz), 6.03(1H, dd, J=3, 1Hz), 4.50–4.37(1H, m), 4.01(1H, br.s), 3.30(2H, t, J=7Hz), 2.91–2.81(2H, m), 2.78(3H, s), 2.75–2.62(4H, m), 2.45(2H, ddd, J=11, 11, 3Hz), 1.76–1.58(6H, m), 1.31(6H, d, J=6Hz) | oil |
| 38-1 | — | CDCl$_3$*: 7.19(1H, dd, J=5, 1Hz), 6.96–6.77(6H, m), 4.80(1H, br.s), 4.55–4.28(2H, m), 3.94(1H, d, J=16Hz), 3.88(1H, d, J=16Hz), 3.75–3.62(1H, m), 3.49(1H, ddd, J=13, 13, 3Hz), 3.24(2H, t, J=6Hz), 3.09(1H, ddd, J=13, 13, 3Hz), 2.75(3H, s), 1.76–1.57(4H, m), 1.45(1H, ddd, J=13, 13, 5Hz), 1.35–1.21(1H, m), 1.31(6H, d, J=6Hz) | — |
| 38-2 | liquid film: 2935, 1510, 1238, 1113 | CDCl$_3$*: 7.12(1H, dd, J=5, 1Hz), 6.95–6.78(6H, m), 4.50–4.33(1H, m), 3.30(2H, t, J=7Hz), 3.04(2H, t, J=8Hz), 2.79(3H, s), 2.76–2.63(4H, m), 2.47(2H, ddd, J=11, 11, 4Hz), 1.78–1.58(6H, m), 1.31(6H, d, J=6Hz) | oil |
| 39-1 | — | CDCl$_3$*: 7.28(1H, dd, J=5, 3Hz), 7.06(1H, dd, J=3, 1Hz), 7.01(1H, dd, J=5, 1Hz), 6.90(2H, d, J=9Hz), 6.83(2H, d, J=9Hz), 4.74(1H, br.s), 4.52–4.25(2H, m), 3.77(1H, d, J=16Hz), 3.70(1H, d, J=16Hz), 3.69–3.54(1H, m), 3.43(1H, ddd, J=13, 13, 3Hz), 3.22(2H, t, J=6Hz), 3.08(1H, ddd, J=13, 13, 3Hz), 2.75(3H, s), 1.75–1.53(4H, m), 1.43(1H, ddd, J=13, 13, 5Hz), 1.31(6H, d, J=6Hz), 1.19(1H, ddd, J=13, 13, 5Hz) | — |
| 39-2 | liquid film: 2935, 1510, 1238, 1115 | CDCl$_3$*: 7.25(1H, dd, J=5, 3Hz), 7.02–6.93(2H, m), 6.89(2H, d, J=9Hz), 6.83(2H, d, J=9Hz), 4.51–4.34(1H, m), 3.30(2H, t, J=7Hz), 2.91–2.81(2H, m), 2.79(3H, s), 2.76–2.58(4H, m), 2.45(2H, ddd, J=11, 11, 4Hz), 1.78–1.58(6H, m), 1.31(6H, d, J=6Hz) | oil |
| 40-1 | — | CDCl$_3$*: 7.16(2H, d, J=9Hz), 6.91(2H, d, J=9Hz), 6.85(2H, d, J=9Hz), 6.82(2H, d, J=9Hz), 4.52–4.31(1H, m), 3.79(3H, s), 3.70–3.57(1H, m), 3.67(2H, s), 3.47–3.29(1H, m), 3.22(2H, t, J=6Hz), 3.08(1H, ddd, J=13, 13, 3Hz), 2.75(3H, s), 1.73–1.10(6H, m), 1.31(6H, d, J=6Hz) | — |
| 40-2 | liquid film: 1512, 1244, 1115 | CDCl$_3$*: 7.12(2H, d, J=9Hz), 6.92–6.78(6H, m), 4.50–4.36(1H, m), 3.78(3H, s), 3.30(2H, t, J=7Hz), 2.83–2.68(4H, m), 2.78(3H, s), 2.66–2.56(2H, m), 2.48(2H, ddd, J=10, 10, 4Hz), 1.77–1.62(6H, m), 1.31(6H, d, J=6Hz) | oil |
| 41-1 | — | CDCl$_3$*: 7.11(2H, d, J=9Hz), 6.90(2H, d, J=9Hz), 6.82(2H, d, J=9Hz), 6.69(2H, d, J=9Hz), 4.52–4.30(2H, m), 3.70–3.58(1H, m), 3.64(2H, s), 3.39(1H, ddd, J=13, 13, 2Hz), 3.22(2H, t, J=6Hz), 3.08(1H, ddd, J=13, 13, 3Hz), 2.92(6H, s), 2.74(3H, s), 1.72–1.13(6H, m), 1.31(6H, d, J=6Hz) | — |
| 41-2 | KBr: 2937, 1514, 1246, 1113, 816 | CDCl$_3$: 7.09(2H, d, J=9Hz), 6.89(2H, d, J=9Hz), 6.83(2H, d, J=9Hz), 6.70(2H, d, J=9Hz), 4.49–4.37(1H, m), 3.30(2H, t, J=7Hz), 2.91(6H, s), 2.82–2.70(4H, m), 2.79(3H, s), 2.64–2.55(2H, m), 2.46(2H, ddd, J=11, 11, 4Hz), 1.76–1.62(6H, m), 1.31(6H, d, J=6Hz) | 63.9–65.5 |
| 42-1 | — | CDCl$_3$: 7.35–7.20(5H, m), 7.02(2H, d, J=9Hz), 6.89(2H, d, J=9Hz), 5.24(1H, s), 4.05(2H, q, J=7Hz), 3.47(2H, s), 3.23(3H, s), 2.59–2.49(2H, m), 2.39(2H, ddd, J=12, 12, 2Hz), 2.16(2H, s), 1.71–1.61(2H, m), 1.46–1.32(2H, m), 1.45(3H, t, J=7Hz) | — |
| 42-2 | — | CDCl$_3$: 7.38–7.22(5H, m), 6.89(2H, d, J=9Hz), 6.82(2H, d, J=9Hz), 3.98(2H, q, J=7Hz), 3.54(2H, s), 3.28(2H, t, J=7Hz), 2.77(3H, s), 2.70–2.58(2H, m), 2.48–2.34(2H, m), 1.76–1.62(6H, m), 1.39(3H, t, J=7Hz) | — |
| 42-3 | — | CDCl$_3$: 6.91(2H, d, J=9Hz), 6.84(2H, d, J=9Hz), 3.99(2H, q, J=7Hz), 3.29(2H, t, J=7Hz), 3.01(2H, ddd, J=12, 12, 3Hz), 2.85(2H, ddd, J=12, 4, 4Hz), 2.78(3H, s), 1.74–1.48(6H, m), 1.39(3H, t, J=7Hz) | — |
| 42-4 | liquid film: 2939, 2227, 1512, 1242, 1119, 1049, 824 | CDCl$_3$*: 7.57(2H, d, J=8Hz), 7.31(2H, d, J=8Hz), 6.92(2H, d, J=9Hz), 6.84(2H, d, J=9Hz), 3.99(2H, q, J=7Hz), 3.29(2H, t, J=6Hz), 2.92–2.81(2H, m), 2.78(3H, s), 2.74–2.56(4H, m), 2.45(2H, ddd, J=11, 11, 3Hz), 1.78–1.55(6H, m), 1.39(3H, t, J=7Hz) | oil |
| 43-1 | — | CDCl$_3$*: 7.35–7.18(6H, m), 6.90–6.83(1H, m), 6.70–6.60(2H, m), 5.20(1H, s), 4.61–4.48(1H, m), 3.47(2H, s), 3.25(3H, s), 2.60–2.32(4H, m), 2.21(2H, s), 1.71–1.30(4H, m), 1.36(6H, d, J=5Hz) | — |
| 43-2 | — | CDCl$_3$: 7.35–7.21(5H, m), 7.11(1H, dd, J=9, 9Hz), 6.40–6.35(1H, m), 6.33–6.28(2H, m), 4.59–4.47(1H, m), 3.52(2H, s), 3.47–3.39(2H, m), 2.87(3H, s), 2.67–2.58(2H, m), 2.35(1H, ddd, J=11, 11, 4Hz), 1.75–1.59(6H, m), 1.33(6H, d, J=6Hz) | — |
| 43-3 | — | CDCl$_3$: 7.13(1H, dd, J=8, 8Hz), 6.42–6.38(1H, m), 6.34–6.29(2H, m), 4.59–4.47(1H, m), 3.49–3.40(2H, m), 3.02–2.80(4H, m), 2.88(3H, s), 1.76–1.53(6H, m), 1.33(6H, d, J=6Hz) | — |
| 43-4 | KBr: 2935, 2225, 1608, 1570, 1502, 1238, 1095 | CDCl$_3$*: 7.57(2H, d, J=8Hz), 7.31(2H, d, J=(Hz), 7.13(1H, dd, J=8, 8Hz), 6.43–6.29(3H, m), 4.60–4.46(1H, m), 3.44(2H, t, J=7Hz), 2.91–2.82(2H, m), 2.88(3H, m), 2.75–2.62(4H, m), 2.48–2.35(2H, m), 1.78–1.58(6H, m), 1.33(6H, d, J=6Hz) | 114.3–116.1 |

TABLE 5-continued

| Example No. | IR (cm⁻¹) | NMR (ppm) (no mark: 300 MHz, *: 270 MHz) | melting point (° C.) |
|---|---|---|---|
| 44-1 | — | CDCl₃*: 7.34–7.18(6H, m), 7.11–7.04(1H, m), 6.97–6.88(2H, m), 5.34(1H, s), 4.65–4.51(1H, m), 3.47(2H, s), 3.47(2H, s), 3.16(3H, s), 2.58–2.45(2H, m), 2.39(2H, ddd, J=11, 11, 3Hz), 2.16(1H, d, J=16Hz), 2.07(1H, d, J=16Hz), 1.73–1.25(4H, m), 1.32(3H, d, J=6Hz), 1.30(3H, d, J=6Hz) | — |
| 44-2 | — | CDCl₃: 7.34–7.19(5H, m), 7.08–7.00(2H, m), 6.90–6.83(2H, m), 4.66–4.54(1H, m), 3.51(2H, s), 3.19(2H, t, J=6Hz), 2.67(3H, s), 2.60–2.51(2H, m), 2.41(2H, ddd, J=11, 11, 3Hz), 1.72–1.48(6H, m), 1.36(6H, d, J=6Hz) | — |
| 44-3 | — | CDCl₃*: 7.09–7.00(2H, m), 6.92–6.83(2H, m), 4.68–4.53(1H, m), 3.20(2H, t, J=6Hz), 3.04(2H, ddd, J=12, 12, 3Hz), 2.85–2.76(2H, m), 2.68(3H, s), 1.74–1.40(6H, m), 1.36(6H, d, J=6Hz) | — |
| 44-4 | liquid film: 2974, 2227, 1497, 1232, 1119 | CDCl₃: 7.56(2H, d, J=8Hz), 7.31(2H, d, J=8Hz), 7.09–7.02(2H, m), 6.91–6.85(2H, m), 4.67–4.55(1H, m), 3.21(2H, t, J=6Hz), 2.90–2.83(2H, m), 2.68(3H, s), 2.68–2.57(2H, m), 2.47(2H, ddd, J=11, 11, 3Hz), 1.73–1.48(6H, m), 1.36(6H, d, J=6Hz) | oil |
| 45-1 | — | CDCl₃*: 7.72(1H, br.s), 7.38–7.21(7H, m), 6.84(1H, d, J=9Hz), 4.55–4.42(1H, m), 3.93(1H, br.s), 3.53(2H, s), 2.63–2.40(4H, s), 2.47(2H, s), 1.82–1.60(4H, m), 1.31(6H, d, J=6Hz) | — |
| 45-2 | — | CDCl₃: 7.35–7.22(5H, m), 6.78(2H, d, J=9Hz), 6.63(2H, d, J=9Hz), 4.45–4.32(1H, m), 3.52(2H, s), 3.27(2H, t, J=6Hz), 2.68–2.58(2H, m), 2.42–2.30(2H, m), 1.78(2H, t, J=6Hz), 1.74–1.60(4H, m), 1.29(6H, d, J=6Hz) | — |
| 45-3 | — | CDCl₃: 6.79(2H, d, J=9Hz), 6.63(2H, d, J=9Hz), 4.45–4.32(1H, m), 3.47(1H, s), 3.28(2H, t, J=6Hz), 2.97(2H, ddd, J=12, 12, 3Hz), 2.84(2H, ddd, J=12, 4, 4Hz), 1.79(2H, t, J=6Hz), 1.70–1.48(4H, m), 1.29(6H, d, J=6Hz), | — |
| 45-4 | KBr: 2225, 1510, 1246, 1134, 1109, 823 | CDCl₃: 7.58(2H, d, J=8Hz), 7.31(2H, d, J=8Hz), 6.79(2H, d, J=9Hz), 6.65(2H, d, J=9Hz), 4.45–4.32(1H, m), 3.30(2H, t, J=6Hz), 2.92–2.84(2H, m), 2.76–2.58(4H, m), 2.43(2H, ddd, J=11, 11, 4Hz), 1.83–1.50(4H, m), 1.80(2H, t, J=6Hz), 1.29(6H, d, J=6Hz) | 111.5–112.5 |
| 46-1 | — | CDCl₃: 7.45–7.15(10H, m), 6.94(2H, d, J=8Hz), 6.80(2H, d, J=8Hz), 4.66(1H, d, J=12Hz), 4.58–4.46(1H, m), 4.38(1H, d, J=12Hz), 4.28(1H, s), 3.81(1H, s), 3.48(2H, s), 3.28(3H, s), 2.68–2.58(2H, m), 2.46–2.27(2H, m), 1.96–1.87(1H, m), 1.57–1.23(9H, m) | — |
| 46-2 | — | CDCl₃: 7.12(2H, d, J=9Hz), 6.90(2H, d, J=9Hz), 4.62–4.47(1H, m), 3.77(1H, s), 3.27(3H, s), 3.00(1H, ddd, J=12, 12, 3Hz), 2.89(1H, ddd, J=12, 12, 3Hz), 2.82–2.72(2H, m), 1.82–1.73(1H, m), 1.50–1.15(3H, m), 1.36(6H, d, J=6Hz) | — |
| 46-3 | — | CDCl₃: 6.87(2H, d, J=9Hz), 6.82(2H, d, J=9Hz), 4.49–4.36(1H, m), 3.60(1H, dd, J=10, 4Hz), 3.31(1H, dd, J=14, 10Hz), 3.11(1H, dd, J=14, 4Hz), 3.05–2.80(4H, m), 2.81(3H, m), 1.85–1.76(1H, m), 1.66–1.40(3H, m), 1.30(6H, d, J=6Hz) | — |
| 46-4 | liquid film: 2227, 1510, 1371, 1238, 1115 | CDCl₃: 7.58(2H, d, J=8Hz), 7.32(2H, d, J=8Hz), 6.88(2H, d, J=9Hz), 6.82(2H, d, J=9Hz), 4.50–4.37(1H, m), 3.60(1H, dd, J=11, 4Hz), 3.32(1H, dd, J=13, 11Hz), 3.09(1H, dd, J=13, 4Hz), 2.93–2.73(4H, m), 2.81(3H, m), 2.67–2.59(2H, m), 2.50–2.37(2H, m), 1.94–1.85(1H, m), 1.72(1H, ddd, J=13, 13, 4Hz), 1.66–1.55(2H, m), 1.31(6H, d, J=6Hz) | oil |
| 47-1 | — | CDCl₃: 7.03(2H, d, J=9Hz), 6.90(2H, d, J=9Hz), 4.62–4.50(1H, m), 3.90–3.65(2H, m), 3.24(3H, s), 3.25–3.10(2H, m), 2.16(2H, s), 1.68–1.58(2H, m), 1.43(9H, s), 1.37(6H, d, J=6Hz), 1.35–1.18(2H, m) | — |
| 47-2 | — | CDCl₃: 7.05(2H, d, J=9Hz), 6.89(2H, d, J=9Hz), 4.61–4.49(1H, m), 3.90–3.65(2H, m), 3.22(3H, s), 3.10–2.87(2H, m), 3.04(3H, s), 2.35(2H, s), 1.80–1.64(4H, m), 1.44(9H, s), 1.36(6H, d, J=6Hz). | — |
| 47-3 | — | CDCl₃: 6.83(2H, d, J=9Hz), 6.69(2H, d, J=9Hz), 4.45–4.32(1H, m), 3.38–3.27(2H, m), 3.19(3H, s), 2.96–2.72(4H, m), 2.84(3H, s), 1.82–1.62(4H, m), 1.59–1.38(2H, m), 1.30(6H, d, J=6Hz). | — |
| 47-4 | liquid film: 2939, 2227, 1608, 1238, 1113, 1078 | CDCl₃: 7.57(2H, d, J=8Hz), 7.31(2H, d, J=8Hz), 6.82(2H, d, J=9Hz), 6.69(2H, d, J=9Hz), 4.45–4.32(1H, m), 3.37–3.27(2H, m), 3.18(3H, s), 2.86(2H, t, J=8Hz), 2.84(3H, s), 2.72–2.55(4H, m), 2.41–2.28(2H, m), 1.90–1.78(2H, m), 1.72–1.48(4H, m), 1.30(6H, d, J=6Hz) | oil |
| 48-1 | liquid film: 1510, 1369, 1240, 1113 | CDCl₃: 7.37–7.21(5H, m), 6.84(2H, d, J=9Hz), 6.80(2H, d, J=9Hz), 4.45–4.32(1H, m), 3.53(2H, s), 3.17(2H, s), 2.92(3H, s), 2.74–2.65(2H, m), 2.36(2H, ddd, J=11, 11, 4Hz), 1.98(1H, s), 1.78–1.60(4H, m), 1.29(6H, d, J=6Hz) | oil |
| 48-2 | — | CDCl₃: 6.86(2H, d, J=9Hz), 6.81(2H, d, J=9Hz), 4.46–4.32(1H, m), 3.17(2H, s), 3.06–2.85(4H, m), 2.94(3H, s), 1.70–1.52(4H, m), 1.29(6H, d, J=6Hz) | — |
| 48-3 | liquid film: 2937, 2227, 1510, 1371, 1240, 1115 | CDCl₃: 7.58(2H, d, J=8Hz), 7.32(2H, d, J=8Hz), 6.86(2H, d, J=9Hz), 6.81(2H, d, J=9Hz), 4.47–4.32(1H, m), 3.18(2H, s), 2.94(3H, s), 2.92–2.58(6H, m), 2.51–2.35(2H, m), 1.78–1.65(4H, m), 1.30(6H, d, J=6Hz) | oil |
| 49 | KBr: 2979, 2937, 2227, 1512, 1238, 1124, 1093 | CDCl₃*: 7.57(2H, d, J=8Hz), 7.31(2H, d, J=8Hz), 6.89(2H, d, J=9Hz), 6.84(2H, d, J=9Hz), 4.50–4.36(1H, m), 3.30(2H, t, J=6Hz), 2.92–2.80(2H, m), 2.78(3H, m), 2.76–2.56(4H, m), 2.45(2H, ddd, J=11, 11, 3Hz), 1.78–1.50(6H, m), 1.31(6H, d, J=6Hz) | 80.4–81.2 |

TABLE 5-continued

| Example No. | IR (cm⁻¹) | NMR (ppm) (no mark: 300 MHz, *: 270 MHz) | melting point (° C.) |
|---|---|---|---|
| 50 | KBr: 1512, 1470, 1255, 1109, 951 | CD₃OD: 7.57(2H, d, J=9Hz), 7.37–7.22(5H, m), 7.09(2H, d, J=9Hz), 4.73–4.59(1H, m), 3.74(2H, t, J=8Hz), 3.55–3.20(6H, m), 3.28(3H, s), 3.13–3.00(2H, m), 2.10–1.50(6H, m), 1.33(6H, d, J=6Hz) | 189.7–192.6 |
| 51 | KBr: 2229, 1510, 1470, 1257, 1109, 953, 835 | CD₃OD*: 7.71(2H, d, J=8Hz), 7.57(2H, d, J=9Hz), 7.51(2H, d, J=8Hz), 7.10(2H, d, J=9Hz), 4.75–4.58(1H, m), 3.75(2H, t, J=8Hz), 3.55–3.10(8H, m), 3.28(3H, s), 2.10–1.50(6H, m), 1.33(6H, d, J=6Hz) | 201.8–203.0 |
| 55 | KBr: 1512, 1470, 1257, 1109, 955, 835 | CD₃OD: 7.58(2H, d, J=9Hz), 7.32(2H, dd, J=9, 4Hz), 7.10(2H, d, J=9Hz), 7.06(2H, dd, J=9, 9Hz), 4.75–4.60(1H, m), 3.75(2H, t, J=7Hz), 3.55–3.20(6H, m), 3.28(3H, s), 3.13–3.00(2H, m), 2.10–1.50(6H, m), 1.33(6H, d, J=6Hz) | 252 dec |
| 84 | KBr: 1510, 1255, 1109, 953 | CD₃OD: 7.61–7.43(4H, m), 7.10(2H, d, J=9Hz), 6.44–6.41(1H, m), 4.74–4.60(1H, m), 3.74(2H, t, J=8Hz), 3.55–3.30(4H, m), 3.28(3H, s), 2.93(2H, t, J=8Hz), 2.05–1.50(6H, m), 1.33(6H, d, J=6Hz) | 202.6–203.9 |
| 86 | KBr: 1510, 1468, 1255, 1109, 953 | CD₃OD: 7.57(2H, d, J=9Hz), 7.30(1H, dd, J=5, 1Hz), 7.09(2H, d, J=9Hz), 7.03–6.93(2H, m), 4.73–4.60(1H, m), 3.74(2H, t, J=8Hz), 3.55–3.20(8H, m), 3.28(3H, s), 2.05–1.50(6H, m), 1.33(6H, d, J=6Hz) | 203.0–204.5 |
| 90 | KBr: 2229, 1514, 1475, 1257, 1180, 1043 | CD₃OD: 7.71(2H, d, J=8Hz), 7.57(2H, d, J=9Hz), 7.51(2H, d, J=8Hz), 7.12(2H, d, J=9Hz), 4.09(2H, q, J=7Hz), 3.75(2H, t, J=8Hz), 3.55–3.10(8H, m), 3.29(3H, s), 2.05–1.50(6H, m), 1.41(3H, t, J=7Hz) | 214.0–215.2 |
| 93 | KBr: 2229, 1604, 1512, 1253, 829 | CD₃OD: 7.72(2H, d, J=8Hz), 7.51(2H, d, J=8Hz), 7.27(2H, d, J=9Hz), 7.01(2H, d, J=9Hz), 4.66–4.54(1H, m), 3.60–3.10(10H, m), 2.10–1.80(6H, m), 1.31(6H, d, J=6Hz) | 197.3 dec |
| 96 | KBr: 2229, 1510, 1458, 1255, 1109, 951 | CD₃OD: 7.71(2H, d, J=8Hz), 7.60(2H, d, J=9Hz), 7.48(2H, d, J=8Hz), 7.09(2H, d, J=9Hz), 4.73–4.60(1H, m), 3.87–3.70(2H, m), 3.57–3.05(8H, m), 3.33(3H, s), 2.05–1.45(4H, m), 1.32(6H, d, J=6Hz) | 202.8–203.4 |
| 97 | KBr: 2561, 2227, 1512, 1468, 1259 | CD₃OD: 7.71(2H, d, J=8Hz), 7.58(2H, d, J=9Hz), 7.52(2H, d, J=8ZHz), 7.10(2H, d, J=9Hz), 4.74–4.61(1H, m), 3.77(2H, t, J=8Hz), 3.60–3.47(2H, m), 3.44–3.13(6H, m), 3.30(3H, s), 2.10–1.52(6H, m), 1.33(6H, d, J=6Hz) | 216.7 dec |
| 98 | KBr: 2229, 1583, 1510, 1385, 1354 | CD₃OD: 7.70(2H, d, J=8Hz), 7.49(2H, d, J=8Hz), 7.32(2H, d, J=9Hz), 7.01(2H, d, J=9Hz), 6.27(4H, s), 4.66–4.53(1H, m), 3.70–3.60(2H, m), 3.56–3.24(6H, m), 3.21–3.10(2H, m), 3.15(3H, s), 1.96–1.82(4H, m), 1.78–1.66(2H, m), 1.31(6H, d, J=6Hz) | 143.5–145.4 |
| 99 | KBr: 2229, 1510, 1238, 1171, 1122, 1016, 729 | CD₃OD: 7.87–7.79(4H, m), 7.68(2H, d, J=8Hz), 7.53(2H, d, J=9Hz), 7.49–7.39(8H, m), 7.08(2H, d, J=9Hz), 4.72–4.59(1H, m), 3.75(2H, t, J=8Hz), 3.59–3.44(2H, m), 3.40–3.22(4H, m), 3.28(3H, s), 3.18–3.06(2H, m), 2.08–1.48(6H, m), 1.32(6H, d, 6Hz) | 190.4–193.0 |

The structure of the compounds of Example 1 to Example 99 are shown in Table 6. In the abbreviations of the substituents used in the structures in Table 6, Me— means CH₃— and Et— means C₂H₅—.

TABLE 6

| Example No. | R— |
|---|---|
| 1 | phenyl-CH₂CH₂— |
| 2 | 4-NC-C₆H₄-CH₂CH₂— |
| 3 | 4-MeOOC-C₆H₄-CH₂CH₂— |
| 4 | 4-EtOOC-C₆H₄-CH₂CH₂— |
| 5 | 4-(Me-S(=O))-C₆H₄-CH₂CH₂— |
| 6 | 4-F-C₆H₄-CH₂CH₂— |
| 7 | 4-O₂N-C₆H₄-CH₂CH₂— |

TABLE 6-continued

![Structure: 4-hydroxy-4-[2-(N-methyl-N-(4-isopropoxyphenyl)amino)ethyl]-1-R-piperidine]

| Example No. | R— |
|---|---|
| 8 | 3-cyanophenylpropyl (3-CN-C6H4-CH2CH2CH2-) |
| 9 | 3-fluorophenylpropyl |
| 10 | 2-fluorophenylpropyl |
| 11 | 4-chlorophenylpropyl |
| 12 | 3-chlorophenylpropyl |
| 13 | 2-chlorophenylpropyl |
| 14 | 4-(trifluoromethyl)phenylpropyl |
| 15 | 3-(trifluoromethyl)phenylpropyl |
| 16 | 2-(trifluoromethyl)phenylpropyl |
| 17 | 3-nitrophenylpropyl |
| 18 | 2-nitrophenylpropyl |
| 19 | 4-methylphenylpropyl |
| 20 | 3-methylphenylpropyl |
| 21 | 2-methylphenylpropyl |
| 22 | 4-bromophenylpropyl |
| 23 | 3-bromophenylpropyl |
| 24 | 2-bromophenylpropyl |
| 25 | 4-(trifluoromethoxy)phenylpropyl |

TABLE 6-continued

[Structure: 4-hydroxy-4-[2-(N-methyl-N-(4-isopropoxyphenyl)amino)ethyl]piperidine with N-R substituent]

| Example No. | R— |
|---|---|
| 26 | 4-(MeS)-C6H4-CH2CH2CH2- |
| 27 | 4-(MeSO2)-C6H4-CH2CH2CH2- |
| 28 | 4-(H2NSO2)-C6H4-CH2CH2CH2- |
| 29 | 4-(NC)-C6H4-CH2CH2CH2- |
| 30 | 2-(CN)-C6H4-CH2CH2CH2- |
| 31 | 4-(HOOC)-C6H4-CH2CH2CH2- |
| 32 | 4-(H2NCO)-C6H4-CH2CH2CH2- |
| 33 | 4-(Me2NCO)-C6H4-CH2CH2CH2- |
| 34 | 4-(MeCO)-C6H4-CH2CH2CH2- |
| 35 | 1-(4-fluorophenyl)-1-hydroxypropyl-... (CH(OH)CH2CH3 attached to 4-F-phenyl) |
| 36 | 3-propylfuran-3-yl group (furan-3-yl-CH2CH2CH2-) |
| 37 | furan-2-yl-CH2CH2CH2- |
| 38 | thien-2-yl-CH2CH2CH2- |
| 39 | thien-3-yl-CH2CH2CH2- |
| 40 | 4-(MeO)-C6H4-CH2CH2CH2- |
| 41 | 4-(Me2N)-C6H4-CH2CH2CH2- |

Example 42

[Structure: 4-hydroxy-4-[2-(N-methyl-N-(4-ethoxyphenyl)amino)ethyl]-1-[2-(4-cyanophenyl)ethyl]piperidine]

Example 43

[Structure: 4-hydroxy-4-[2-(N-methyl-N-(3-isopropoxyphenyl)amino)ethyl]-1-[2-(4-cyanophenyl)ethyl]piperidine]

-continued

Example 44
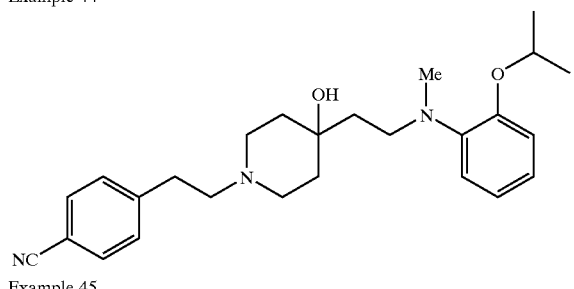

Example 45
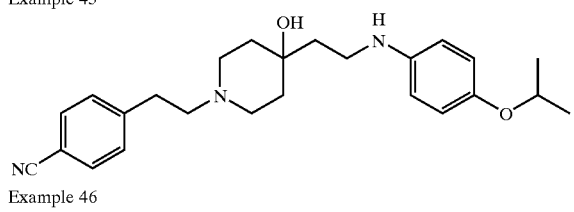

Example 46
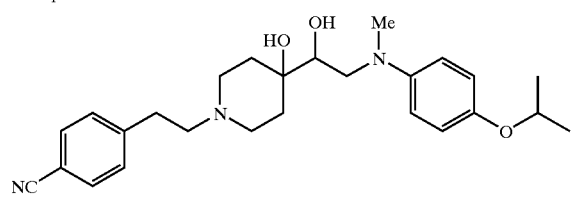

Example 47
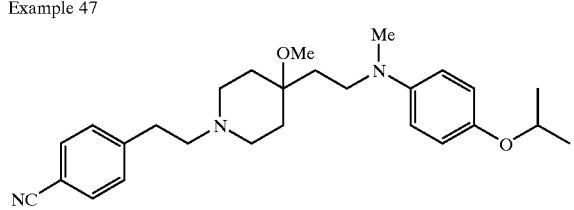

Example 48
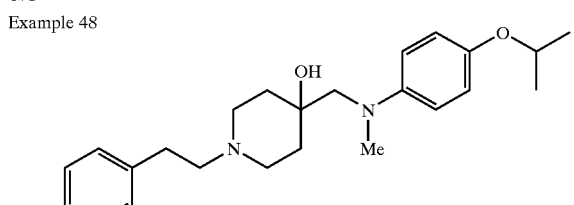

Example 49
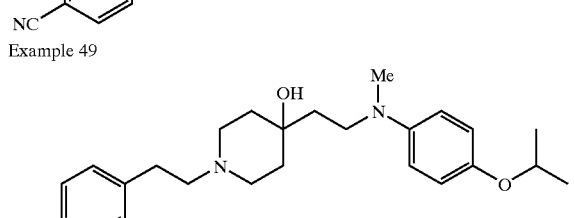

Example 50 dihydrochloride of compound of Example No. 1
Example 51 dihydrochloride of compound of Example No. 2
Example 52 dihydrochloride of compound of Example No. 3
Example 53 dihydrochloride of compound of Example No. 4
Example 54 dihydrochloride of compound of Example No. 5
Example 55 dihydrochloride of compound of Example No. 6
Example 56 dihydrochloride of compound of Example No. 7
Example 57 dihydrochloride of compound of Example No. 8
Example 58 dihydrochloride of compound of Example No. 9
Example 59 dihydrochloride of compound of Example No. 10
Example 60 dihydrochloride of compound of Example No. 11
Example 61 dihydrochloride of compound of Example No. 12
Example 62 dihydrochloride of compound of Example No. 13
Example 63 dihydrochloride of compound of Example No. 14
Example 64 dihydrochloride of compound of Example No. 15
Example 65 dihydrochloride of compound of Example No. 16
Example 66 dihydrochloride of compound of Example No. 17
Example 67 dihydrochloride of compound of Example No. 18
Example 68 dihydrochloride of compound of Example No. 19
Example 69 dihydrochloride of compound of Example No. 20
Example 70 dihydrochloride of compound of Example No. 21
Example 71 dihydrochloride of compound of Example No. 22
Example 72 dihydrochloride of compound of Example No. 23
Example 73 dihydrochloride of compound of Example No. 24
Example 74 dihydrochloride of compound of Example No. 25
Example 75 dihydrochloride of compound of Example No. 26
Example 76 dihydrochloride of compound of Example No. 27
Example 77 dihydrochloride of compound of Example No. 28
Example 78 dihydrochloride of compound of Example No. 30
Example 79 dihydrochloride of compound of Example No. 31
Example 80 dihydrochloride of compound of Example No. 32
Example 81 dihydrochloride of compound of Example No. 33
Example 82 dihydrochloride of compound of Example No. 34
Example 83 dihydrochloride of compound of Example No. 35
Example 84 dihydrochloride of compound of Example No. 36
Example 85 dihydrochloride of compound of Example No. 37
Example 86 dihydrochloride of compound of Example No. 38
Example 87 dihydrochloride of compound of Example No. 39
Example 88 dihydrochloride of compound of Example No. 40
Example 89 trihydrochloride of compound of Example No. 41
Example 90 dihydrochloride of compound of Example No. 42

Example 91 dihydrochloride of compound of Example No. 43
Example 92 dihydrochloride of compound of Example No. 44
Example 93 dihydrochloride of compound of Example No. 45
Example 94 dihydrochloride of compound of Example No. 46
Example 95 dihydrochloride of compound of Example No. 47
Example 96 dihydrochloride of compound of Example No. 48
Example 97 dihydrobromide of compound of Example No. 2
Example 98 dimaleate of compound of Example No. 2
Example 99 dibenzenesulfonate of compound of Example No. 2

The structures of the compounds manufactured in Step 1 of Examples 9 to 28, Example 35 and Examples 37 to 41 are shown in Table 7. In the abbreviations of the substituents used in the structures in Table 7, Me— means $CH_3$— and Et— means $C_2H_5$—. Example No. in the Table, e.g., Example No. 9-1 means Step 1 of Example 9, and the compounds in the Table 7 are intermediates of the compounds of the corresponding Example No.

TABLE 7

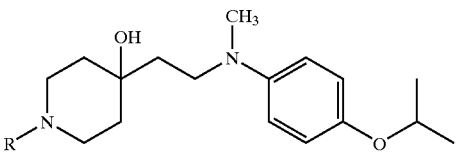

| Example No. | R— |
|---|---|
| 9-1 | 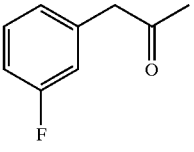 |
| 10-1 | 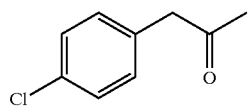 |
| 11-1 | 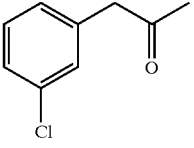 |
| 12-1 | 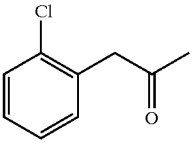 |
| 13-1 | 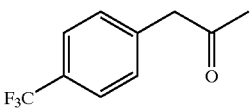 |

TABLE 7-continued

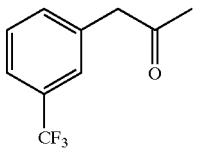

| Example No. | R— |
|---|---|
| 14-1 | 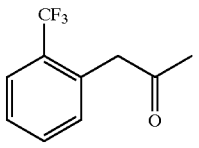 |
| 15-1 | 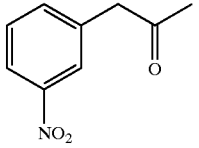 |
| 16-1 | 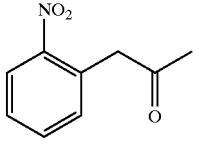 |
| 17-1 | 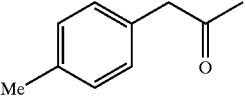 |
| 18-1 | 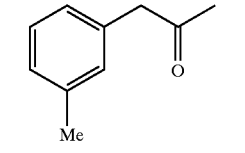 |
| 19-1 | 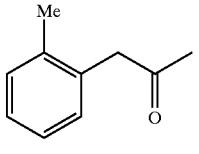 |
| 20-1 | (see structure) |
| 21-1 | (see structure) |
| 22-1 | 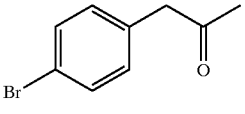 |

TABLE 7-continued common structure: 1-R-4-hydroxy-4-[2-(N-methyl-N-(4-isopropoxyphenyl)amino)ethyl]piperidine

| Example No. | R— |
|---|---|
| 23-1 | 3-bromophenyl-CH₂-C(=O)-CH₂- (acetonyl with 3-Br phenyl) |
| 24-1 | 2-bromophenyl acetonyl |
| 25-1 | 4-(F₃CO)phenyl acetonyl |
| 26-1 | 4-(MeS)phenyl acetonyl |
| 27-1 | 4-(MeS(O)₂)phenyl acetonyl |
| 28-1 | 4-(H₂NS(O)₂)phenyl acetonyl |
| 35-1 | 4-fluorophenyl propanoyl |
| 37-1 | 2-furyl acetonyl |
| 38-1 | 2-thienyl acetonyl |
| 39-1 | 3-thienyl acetonyl |
| 40-1 | 4-(MeO)phenyl acetonyl |
| 41-1 | 4-(Me₂N)phenyl acetonyl |

Example of Formulation

Examples of formulations containing the compounds according to the present invention are shown below. However, the present invention is by no means restricted to these examples.

Formulation Example 1: Tablet

| | |
|---|---|
| The compound in the Example 50 | 100 g |
| Lactose | 350 g |
| Potato starch | 120 g |
| Polyvinyl alcohol | 15 g |
| Magnesium stearate | 15 g |

After weighing each component above, the compound in the Example 50, lactose and potato starch are homogeneously mixed. An aqueous solution of polyvinyl alcohol is added to this mixture, and granules are prepared by a wet granulation method. The granules are dried, mixed with magnesium stearate, and formed into tablets each weighing 300 mg by press-molding.

Formulation Example 2: Capsules

| | |
|---|---|
| The compound in the Example 50 | 50 g |
| Lactose | 435 g |
| Magnesium stearate | 15 g |

The components above are homogeneously mixed after weighing. Three hundred milligram each of the mixture is filled in an appropriate hard capsule each weighing 300 mg by using a capsule-encapulating machine to prepare a capsule drug.

Formulation Example 3: Injections

| | |
|---|---|
| The compound in the Example 51 | 2 g |
| Propylene glycol | 200 g |
| Distilled water for injection | proper volume |

The compound in the Example 51 is dissolved in propylene glycol after weighing each component. Aseptic water for injection is added to make a total volume of 1000 mL, and 5 mL each of the aqueous solution is dispensed in a 10 mL ampoule after aseptic filtration, followed by fusing the ampoule to prepare an injection.

Formulation Example 4: Suppository

| The compound in the Example 51 | 100 g |
| Polyethylene glycol 1500 | 180 g |
| Polyethylene glycol 4000 | 720 g |

After grinding the compound in the Example 51 in a mortar into fine powder, suppositories each weighing 1 g are prepared by hot-melting.

Formulation Example 5: Powder

| The compound in the Example 55 | 200 g |
| Lactose | 790 g |
| Magnesium stearate | 10 g |

A powder containing 20% of the effective ingredient is prepared by mixing each component after weighing.

Industrial Applicability

The compound of this invention was successful in treating pain when orally applied to the animal pain model or to the neuropathy pain model without practically affecting the threshold of a normal nerve fiber to a nociceptive stimulus. Thus, the compound of this invention gives a prospect of providing a new orally applicable agent for treating neuropathic pain presenting with few side-effects in contrast with the conventional analgesics. The agent prepared from the compound will be also effective for preventing or retarding the further aggravation of the chronic diseases responsible for neuropathic pain. The agent of this invention which selectively blocks the persistent sodium current will become an excellent therapeutic agent for treating neuropathic pain while presenting with few side-effects.

What is claimed is:

1. A compound as shown in the following formula (I)

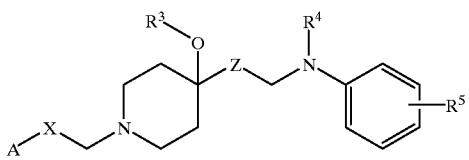

(I)

(wherein A represents a phenyl group or a monocyclic aromatic heterocyclic ring each optionally substituted by $R^1$ and/or $R^2$; $R^1$ and $R^2$ represent, independently of each other, a group selected from the group consisting of halogen atom, trifluoromethyl group, trifluoromethoxy group, nitro group, cyano group, lower alkoxycarbonyl group, amino group unsubstituted or mono- or di-substituted by lower alkyl-groups, carbamoyl group unsubstituted or mono- or di-substituted by lower alkyl groups, sulfamoyl group unsubstituted or mono- or di-substituted by lower alkyl groups, unprotected or protected hydroxyl group, unprotected or protected carboxyl group, lower alkoxy group, lower alkyl group, lower alkylthio group, lower alkylsulfinyl group, lower alkylsulfonyl group and lower alkanoyl group; $R^3$ represents hydrogen atom or lower alkyl group; $R^4$ represents hydrogen atom or a lower alkyl group; $R^5$ represents ethoxy group or isopropoxy group; X represents CH(OH)— or methylene group; and Z represents a single bond or methylene group unsubstituted or substituted by unprotected or protected hydroxyl group, or pharmaceutically acceptable salt thereof.

2. A compound or salt thereof as claimed in claim 1, wherein A represents phenyl group, furyl group or thienyl group each optionally substituted by $R^1$, $R^1$ represents halogen atom, trifluoromethyl group, trifluoromethoxy group, nitro group, cyano group, lower alkoxycarbonyl group, lower alkoxy group, lower alkyl group, lower alkylthio group or lower alkanoyl group.

3. Pharmaceutical composition characterized by containing, as an active ingredient, the compound or the pharmaceutically acceptable salt thereof as shown in Formula (I) as claimed is claim 1.

4. Pharmaceutical composition as claimed in claim 3, wherein the composition is an agent for treating neuropathic pain or an allodynia treating agent.

5. An agent for treating neuropathic pain or an allodynia treating agent as claimed is claim 4, wherein the agent can be orally administered to mammals.

* * * * *